United States Patent
Huang

(10) Patent No.: US 11,801,232 B2
(45) Date of Patent: Oct. 31, 2023

(54) TARGETING OF ARID1A-DEFICIENT CANCERS BY INHIBITING DE NOVO PYRIMIDINE SYNTHESIS PATHWAY

(71) Applicant: YALE UNIVERSITY, New Haven, CT (US)

(72) Inventor: Gloria Huang, Greenwich, CT (US)

(73) Assignee: YALE UNIVERSITY, New Haven, CT (US)

( * ) Notice: Subject to any disclaimer, the term of this patent is extended or adjusted under 35 U.S.C. 154(b) by 163 days.

(21) Appl. No.: 17/102,992

(22) Filed: Nov. 24, 2020

(65) Prior Publication Data
US 2021/0154165 A1    May 27, 2021

Related U.S. Application Data

(60) Provisional application No. 62/941,037, filed on Nov. 27, 2019.

(51) Int. Cl.
| | |
|---|---|
| A61K 31/277 | (2006.01) |
| A61K 31/42 | (2006.01) |
| A61P 35/00 | (2006.01) |
| A61K 31/5377 | (2006.01) |
| A61K 31/497 | (2006.01) |
| A61K 31/506 | (2006.01) |

(52) U.S. Cl.
CPC ............ *A61K 31/277* (2013.01); *A61K 31/42* (2013.01); *A61K 31/497* (2013.01); *A61K 31/506* (2013.01); *A61K 31/5377* (2013.01); *A61P 35/00* (2018.01)

(58) Field of Classification Search
CPC .. A61K 31/198; A61K 31/351; A61K 31/277; A61P 35/00
See application file for complete search history.

(56) References Cited

U.S. PATENT DOCUMENTS

| | | | | |
|---|---|---|---|---|
| 6,610,718 B2 * | 8/2003 | Avrutov | ................ | C07D 261/18 514/378 |
| 2018/0117029 A1 * | 5/2018 | Toker | .................... | A61K 31/198 |

FOREIGN PATENT DOCUMENTS

WO    2018038886 A1    3/2018

OTHER PUBLICATIONS

Stubbs (Molecular and Cellular Endocrinology vol. 461 pp. 226-235 published 2018). (Year: 2018).*
Williamson (Nature Communications vol. 7:13837 pp. 1-13, published Dec. 13, 2016). (Year: 2016).*
Caumanns (Clinical Cancer Research vol. 24 pp. 3928-3940 published 2018). (Year: 2018).*
Berns, K. et al., "Loss of ARID1A Activates ANXA1, Which Serves as a Predictive Biomarket for Trastuzumab Resistance" Clinical Cancer Research (2016) vol. 22, No. 21, pp. 5238-5248.
Brown, K.K. et al., "Adaptive Reprogramming of De Novo Pyrimidine Synthesis is a Metabolic Vulnerability in Triple-Negative Breast Cancer" Cancer Discovery (2017) vol. 7, No. 4, pp. 391-399.
Brown, K.K. et al., "Correction: Adaptive Reprogramming of De Novo Pyurimidine Synthesis is a Metabolic Vulnerability in Triple-Negative Breast Cancer" Cancer Discovery (2017) vol. 7, No. 4, p. 782.
Guan, B. et al., "Functional Analysis on In-Frame Indel ARID1A Mutations Reveals New Regulatory Mechanisms of its Tumor Suppressor Functions" NeoPlasia (2012) vol. 14, No. 10, pp. 986-993.
He, T. et al., "Inhibition of the Mitochondrial Pyrimidine Biosynthesis Enzyme Dihydroorotate Dehydrogenase by Doxorubicin and Brequinar Sensitizes Cancer Cells to TRAIL-Induced Apoptosis" Oncogene (2014) vol. 33, pp. 3538-3549.
Hu, H-M. et al., "A Quantitative Chemotherapy Genetic Interaction Map Reveals Factors Associated with PARP Inhibitor Resistance" Cell Rep. (2018) vol. 23, No. 3, pp. 918-929.
Huang, G., "Beyond Chromatin Remodeling: Novel Functions of the Tumor Suppressor ARID1A in Cell Metabolism and Migration" (2019) 30 pages total.
Katagiri, A. et al., "Loss of ARID1A Expression is Related to Shorter Progression-Free Survival and Chemoresistance in Ovarian Clear Cell Carcinoma" Modern Pathology (2012) vol. 25, pp. 282-288.
Li, Z. et al., "Vulnerability of ARID1A Deficient Cancer Cells to Pyrimidine Synthesis Blockade" (2020) 24 pages total.
Luo, Q. et al., "ARID1A Ablation Leads to Multiple Drug Resistance in Ovarian Cancer via Transcriptional Activation of MRP2" Cancer Letters (2018) 28 pages total.
Lyu, C. et al., "ARID1A Gene Silencing Reduces the Sensitivity of Ovarian Clear Cell Carcinoma to Cisplatin" Experimental and Therapeutic Medicine (2016) vol. 12, pp. 4067-4071.
Mathur, D. et al., "PTEN Regulates Glutamine Flux to Pyrimidine Synthesis and Sensitivitiy to Dihydroorotate Dehydrogenase Inhibition" Cancer Discovery (2017) vol. 7, No. 4, pp. 380-390.

(Continued)

*Primary Examiner* — Theodore R. Howell
*Assistant Examiner* — George W Kosturko
(74) *Attorney, Agent, or Firm* — Troutman Pepper Hamilton Sanders LLP

(57) ABSTRACT

This application relates to methods and kits for treating ARID1A-mutant tumors, cancers, or aberrantly proliferating cells and subjects harboring the tumors, cancers, or aberrantly proliferating cells. In particular, the methods provided include administering to the subject or cell an effective amount of a pyrimidine synthesis inhibitor and administering to the subject or cell an effective amount of a DNA repair inhibitor. The kits include a) a composition comprising a pyrimidine synthesis inhibitor and b) a composition comprising a DNA repair inhibitor.

19 Claims, 14 Drawing Sheets
(12 of 14 Drawing Sheet(s) Filed in Color)
Specification includes a Sequence Listing.

(56) References Cited

OTHER PUBLICATIONS

MI, S et al., "Identification and Characterization of a Novel ARID1A Interaction with CAD (Carbamoyl-phosphate Synthetase 2, aspartate transcarbamylase, and dihydroorotase)" Albert Einstein College of Medicine, Montefiore Medical Center, An EACR-AACR-SIC Special Conference (2015) 1 page total.
Vyas, V.K. et al., "Design, Synthesis and Pharmacological Evaluation of Novel Substituted Quinoline-2-Carboxamide Derivatives as Human Dihydroorotate Dehydrogenase (hDHODH) Inhibitors and Anticancer Agents" European Journal of Medicinal Chemistry (2014) vol. 82, pp. 385-393.
Xie, C. et al., "Decreased ARID1A expression facilitates cell proliferation and inhibits 5-fluorouracil-induced apoptosis in colorectal carcinoma" Tumor Biol. (2014) vol. 35, pp. 7921-7927.
Yokoyama, Y. et al., "Decreased ARID1A Expression is Correlated with Chemoresistance in Epithelial Ovarian Cancer" Journal of Gynecologic Oncology (2014) vol. 25, No. 1, pp. 58-63.
Zhang, Y. et al., ""ARID1A is downregulated in non-small cell lung cancer and regulates cell proliferation and apoptosis"" Tumor Biol. (2014) vol. 35, Abstract., pp. 5701-5707.
Jean L. Grem, et al., "Biochemistry and Clinical Activity of N-(Phosphonacetyl)-l-aspartate: A Review", Cancer Research 1988; 48:4441-4454.
J. Mateo, et al., "A decade of clinical development of PARP inhibitors in perspective", Annals of Oncology 2019; 30(9): 1437-1447, doi:10.1093/annonc/mdz192.
Silvia Domcke, et al., "Evaluating cell lines as tumour models by comparison of genomic profiles", Nature Communications 2013; 4:2126, doi: 10.1038/ncomms3126.

\* cited by examiner

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctctcttat acacagcaga t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccgttgatga actcattggt t                                              21

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctaaggtta agtcgccctc gctcgagcga gggcgactta accttagg                 48

<210> SEQ ID NO 4
<211> LENGTH: 6920
<212> TYPE: DNA
<213> ORGANISM: Homo sapiens

<400> SEQUENCE: 4
gaattcatgt acccatacga tgttccagat tacgctgcta gcctcgagcc accatggccg    60
cgcaggtcgc ccccgccgcc gccagcagcc tgggcaaccc gccgccgccg ccgccctcgg    120
agctgaagaa agccgagcag cagcagcggg aggaggcggg gggcgaggcg gcggcggcgg    180
cagcggccga gcgcggggaa atgaaggcag ccgccgggca ggaaagcgag ggccccgccg    240
tggggccgcc gcagccgctg ggaaaggagc tgcaggacgg ggccgagagc aatggggggtg    300 gcggcggcgg cggagccggc agcggcgcg ggcccgcgc ggagccggac ctgaagaact    360
cgaacgggaa cgcgggccct aggcccgccc tgaacaataa cctcacggag ccgccggcg    420 gcggcggtgg cggcagcagc gatggggtgg gggcgcctcc tcactcagcc gcggccgcct    480
tgccgccccc agcctacggc ttcgggcaac cctacggccg gagcccgtct gccgtcgccg    540
ccgccgcggc cgccgtcttc caccaacaac atggcggaca caaagccct ggcctggcag    600 cgctgcagag cggcggcggc gggggcctgg agccctacgc ggggcccag cagaactctc    660 acgaccacgg cttccccaac caccagtaca actcctacta ccccaaccgc agcgcctacc    720
ccccgcccgc cccggcctac gcgctgagct ccccgagagg tggcactccg ggctccggcg    780 cggcggcgg tgccggctcc aagccgcctc cctcctccag cgcctccgcc tcctcgtcgt    840
cttcgtcctt cgctcagcag cgcttcgggg ccatgggggg aggcggcccc tccgcggccg    900

```
gcggggaac tccccagccc accgccaccc ccaccctcaa ccaactgctc acgtcgccca    960
gctcggcccg gggctaccag ggctaccccg ggggcgacta cagtggcggg ccccaggacg   1020
ggggcgccgg caagggcccg gcggacatgg cctcgcagtg ttggggggct gcggcggcgg   1080
cagctgcggc ggcggccgcc tcgggagggg cccaacaaag gagccaccac gcgcccatga   1140
gccccgggag cagcggcggc ggggggcagc cgctcgcccg gacccctcag ccatccagtc   1200
caatggatca gatgggcaag atgagacctc agccatatgg cgggactaac ccatactcgc   1260
agcaacaggg acctccgtca ggaccgcagc aaggacatgg gtacccaggg cagccatacg   1320
ggtcccagac cccgcagcgg tacccgatga ccatgcaggg ccgggcgcag agtgccatgg   1380
gcggcctctc ttatacacag cagattcctc cttatggaca acaaggcccc agcgggtatg   1440
gtcaacaggg ccagactcca tattacaacc agcaaagtcc tcaccctcag cagcagcagc   1500
caccctactc ccagcaacca ccgtcccaga cccctcatgc ccaaccttcg tatcagcagc   1560
agccacagtc tcaaccacca cagctccagt cctctcagcc tccatactcc cagcagccat   1620
cccagcctcc acatcagcag tccccggctc atacccctc ccagcagtcg acgacacagc   1680 agcacccca gagccagccc ccctactcac agccacaggc tcagtctcct taccagcagc   1740
agcaacctca gcagccagca ccctcgacgc tctcccagca ggctgcgtat cctcagcccc   1800
agtctcagca gtcccagcaa actgccatt cccagcagcg cttccctcca ccgcaggagc   1860
tatctcaaga ttcatttggg tctcaggcat cctcagcccc ctcaatgacc tccagtaagg   1920
gagggcaaga agatatgaac ctgagccttc agtcaagacc ctccagcttg cctgatctat   1980
ctggttcaat agatgacctc cccatgggga cagaaggagc tctgagtcct ggagtgagca   2040
catcagggat ttccagcagc caaggagagc agagtaatcc agctcagtct cctttctctc   2100
ctcatacctc ccctcacctg cctggcatcc gaggcccttc cccgtcccct gttggctctc   2160
ccgccagtgt tgctcagtct cgctcaggac cactctcgcc tgctgcagtg ccaggcaacc   2220
agatgccacc tcgccaccc agtggccagt cggacagcat catgcatcct tccatgaacc   2280
aatcaagcat tgcccaagat cgaggttata tgcagaggaa ccccagatg ccccagtaca   2340 gttcccccca gccggctca gccttatctc cgcgtcagcc ttccggagga cagatacaca   2400
caggcatggg ctcctaccag cagaactcca tggggagcta tggtccccag gggggtcagt   2460
atggcccaca aggtggctac cccaggcagc caaactataa tgccttgccc aatgccaact   2520
accccagtgc aggcatggct ggaggcataa acccatgggg tgccggaggt caaatgcatg   2580
gacagcctgg catcccacct tatgcacac tccctccagg gaggatgagt cacgcctcca   2640
tgggcaaccg gccttatggc cctaacatgg ccaatatgcc acctcaggtt gggtcaggga   2700
tgtgtccccc accagggggc atgaaccgga aacccaaga aactgctgtc gccatgcatg   2760
ttgctgccaa ctctatccaa aacaggccgc caggctaccc caatatgaat caagggggca   2820
tgatgggaac tggacctcct tatgacaag ggattaatag tatggctggc atgatcaacc   2880
ctcagggacc cccatattcc atgggtggaa ccatggccaa caattctgca gggatggcag   2940
ccagcccaga gatgatgggc cttggggatg taaagttaac tccagccacc aaaatgaaca   3000
acaaggcaga tgggacaccc aagacagaat ccaaatccaa gaaatccagt tcttctacta   3060
caaccaatga gaagatcacc aagttgtatg agctgggtgg tgagcctgag aggaagatgt   3120
gggtggaccg ttatctggcc ttcactgagg agaaggccat gggcatgaca aatctgcctg   3180
ctgtgggtag gaaacctctg gacctctatc gcctctatgt gtctgtgaag gagattggtg   3240
gattgactca ggtcaacaag aacaaaaaat ggcgggaact tgcaaccaac ctcaatgtgg   3300
```

```
gcacatcaag cagtgctgcc agctccttga aaaagcagta tatccagtgt ctctatgcct    3360
ttgaatgcaa gattgaacgg ggagaagacc ctcccccaga catctttgca gctgctgatt    3420
ccaagaagtc ccagcccaag atccagcctc cctctcctgc gggatcagga tctatgcagg    3480
ggccccagac tccccagtca accagcagtt ccatggcaga aggaggagac ttaaagccac    3540
caactccagc atccacacca cacagtcaga tcccccatt gccaggcatg agcaggagca    3600
attcagttgg gatccaggat gcctttaatg atggaagtga ctccacattc cagaagcgga    3660
attccatgac tccaaaccct gggtatcagc ccagtatgaa tacctctgac atgatggggc    3720
gcatgtccta tgagccaaat aaggatcctt atggcagcat gaggaaagct ccagggagtg    3780
atcccttcat gtcctcaggg cagggcccca acggcgggat gggtgacccc tacagtcgtg    3840
ctgccggccc tgggctagga aatgtgggcga tgggaccacg acagcactat ccctatggag    3900
gtccttatga cagagtgagg acggagcctg aatagggcc tgagggaaac atgagcactg    3960 ggccccaca gccgaatctc atgccttcca acccagactc ggggatgtat tctcctagcc    4020
gctacccccc gcagcagcag cagcagcagc agcaacgaca tgattcctat ggcaatcagt    4080
tctccaccca aggcacccct tctggcagcc ccttccccag ccagcagact acaatgtatc    4140
aacagcaaca gcagaattac aagcggccaa tggatggcac atatggccct cctgccaagc    4200
ggcacgaagg ggagatgtac agcgtgccat acagcactgg gcaggggcag cctcagcagc    4260
agcagttgcc cccagcccag ccccagcctg ccagccagca acaagctgcc cagccttccc    4320
ctcagcaaga tgtatacaac cagtatggca tgcctatcc tgccactgcc acagctgcta    4380
ctgagcgccg accagcaggc ggcccccaga accaatttcc attccagttt ggccgagacc    4440
gtgtctctgc acccctggc accaatgccc agcaaaacat gccaccacaa atgatgggcg    4500
gccccataca ggcatcagct gaggttgctc agcaaggcac catgtggcag gggcgtaatg    4560
acatgaccta taattatgcc aacaggcaga gcacgggctc tgccccccag ggccccgcct    4620
atcatggcgt gaaccgaaca gatgaaatgc tgcacacaga tcagagggcc aaccacgaag    4680
gctcgtggcc ttcccatggc acacgccagc ccccatatgg tccctctgcc cctgtgcccc    4740
ccatgacaag gccccctcca tctaactacc agccccacc aagcatgcag aatcacattc    4800
ctcaggtatc cagccctgct cccctgcccc ggccaatgga gaaccgcacc tctcctagca    4860
agtctccatt cctgcactct gggatgaaaa tgcagaaggc aggtccccca gtacctgcct    4920
cgcacatagc acctgcccct gtgcagcccc ccatgattcg gcgggatatc accttcccac    4980
ctggctctgt tgaagccaca cagcctgtgt tgaagcagag gaggcggctc acaatgaaag    5040
acattggaac cccggaggca tggcgggtaa tgatgtccct caagtctggt ctcctggcag    5100
agagcacatg ggcattagat accatcaaca tcctgctgta tgatgacaac agcatcatga    5160
ccttcaacct cagtcagctc ccaggggttgc tagagctcct tgtagaatat tccgacgat    5220 gcctgattga gatctttggc attttaaagg agtatgaggt gggtgaccca ggacagaaa    5280 cgctactgga tcctgggagg ttcagcaagg tgtctagtcc agctcccatg gagggtgggg    5340
aagaagaaga agaacttcta ggtcctaaac tagaagagga agaagaagag gaagtagttg    5400
aaaatgatga ggagatagcc ttttcaggca aggacaagcc agcttcagag aatagtgagg    5460
agaagctgat cagtaagttt gacaagcttc cagtaaagat cgtacagaag aatgatccat    5520
ttgtggtgga ctgctcagat aagcttgggc gtgtgcagga gtttgacagt ggcctgctgc    5580
actggcggat tggtgggggg gacaccactg agcatatcca gacccacttc gagagcaaga    5640
```

-continued

```
cagagctgct gccttcccgg cctcacgcac cctgcccacc agcccctcgg aagcatgtga      5700
caacagcaga gggtacacca gggacaacag accaggaggg gcccccacct gatggacctc      5760
cagaaaaacg gatcacagcc actatggatg acatgttgtc tactcggtct agcaccttga      5820
ccgaggatgg agctaagagt tcagaggcca tcaaggagag cagcaagttt ccatttggca      5880
ttagcccagc acagagccac cggaacatca agatcctaga ggacgaaccc cacagtaagg      5940
atgagacccc actgtgtacc cttctggact ggcaggattc tcttgccaag cgctgcgtct      6000
gtgtgtccaa taccattcga agcctgtcat ttgtgccagg caatgacttt gagatgtcca      6060
aacacccagg gctgctgctc atcctgggca agctgatcct gctgcaccac aagcacccag      6120
aacggaagca ggcaccacta acttatgaaa aggaggagga acaggaccaa ggggtgagct      6180
gcaacaaagt ggagtggtgg tgggactgct tggagatgct ccgggaaaac accttggtta      6240
cactcgccaa catctcgggg cagttggacc tatctccata ccccgagagc atttgcctgc      6300
ctgtcctgga cggactccta cactgggcag tttgcccttc agctgaagcc caggacccct      6360
tttccaccct gggccccaat gccgtccttt ccccgcagag actggtcttg gaaaccctca      6420
gcaaactcag catccaggac aacaatgtgg acctgattct ggccacaccc cccttcagcc      6480
gcctggagaa gttgtatagc actatggtgc gcttcctcag tgaccgaaag aacccggtgt      6540
gccgggagat ggctgtggta ctgctggcca acctggctca ggggacagcc tggcagctc       6600 gtgccattgc agtgcagaag ggcagtatcg caacctcct gggcttccta aggacagcc        6660 ttgccgccac acagttccag cagagccagg ccagcctcct ccacatgcag aacccaccct      6720
ttgagccaac tagtgtggac atgatgcggc gggctgcccg cgcgctgctt gccttggcca      6780
aggtggacga gaaccactca gagtttactc tgtacgaatc acggctgttg gacatctcgg      6840
tatcaccgtt gatgaactca ttggtttcac aagtcatttg tgatgtactg tttttgattg      6900
gccagtcctc gtgaggatcc                                                  6920
```

<210> SEQ ID NO 5
<211> LENGTH: 6702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gctagaattc gtatggcggc cctagtgttg gaggacgggt cggtcctgcg gggccagccc       60
tttggggccg ccgtgtcgac tgccggggaa gtggtgtttc aaaccggcat ggtcggctac      120
cccgaggccc tcactgatcc ctcctacaag gcacagatct tagtgctcac ctatcctctg      180
atcggcaact atggcatccc ccagatgaa atggatgagt cggtctctg caagtggttt       240 gaatcctcgg gcatccacgt agcagcactg gtagtgggag agtgctgtcc tactcccagc      300
cactggagtg ccaccgcac cctgcatgag tggctgcagc agcatggcat ccctggcttg       360
caaggagtag acactcggga gctgaccaag aagttgcggg aacagggtc tctgctgggg       420 aagctggtcc agaatggaac agaaccttca tccctgccat tcttggaccc caatgcccgc      480
cccctggtac cagaggtctc cattaagact ccacgggtat tcaatacagg gggtgcccct      540
cggatccttg ctttggactg tggcctcaag tataatcaga tccgatgcct ctgccagcgt      600
ggggctgagg tcactgtggt accctgggac catgcactag acagccaaga gtatgagggt      660
ctcttcttaa gtaatgggcc tggtgaccct gcctcctatc ccagtgtcgt atccacactg      720
```

| | |
|---|---|
| agccgtgttt tatctgagcc taatccccga cctgtctttg ggatctgcct gggacaccag | 780 |
| ctattggcct tagccattgg ggccaagact tacaagatga gatatgggaa ccgaggccat | 840 |
| aaccagccct gcttgttggt gggctctggg cgctgctttc tgacatccca gaaccatggg | 900 |
| tttgctgtgg agacagactc actgccagca gactgggctc ctctcttcac caacgccaat | 960 |
| gatggttcca atgaaggcat tgtgcacaac agcttgcctt tcttcagtgt ccagtttcac | 1020 |
| ccagagcacc aagctggccc ttcagatatg gaactgcttt cgatatcttt ctgaaaact | 1080 |
| gtgaaagagg ccacagctgg gaaccctggg ggccagacag ttagagagcg gctgactgag | 1140 |
| cgcctctgtc cccctgggat tcccactccc ggctctggac ttccaccacc acgaaaggtt | 1200 |
| ctgatcctgg gctcaggggg cctctccatt ggccaagctg gagaatttga ctactcgggc | 1260 |
| tctcaggcaa ttaaggccct gaaggaggaa acatccaga cgttgctgat caaccccaat | 1320 |
| attgccacag tgcagacctc ccaggggctg gccgacaagg tctattttct tcccataaca | 1380 |
| cctcattatg taacccaggt gatacgtaat gaacgccccg atggtgtgtt actgactttt | 1440 |
| gggggccaga ctgctctgaa ctgtggtgtg gagctgacca aggccgggt gctggctcgg | 1500 |
| tatggggtcc gggtcctggg cacaccagtg gagaccattg agctgaccga ggatcgacgg | 1560 |
| gcctttgctg ccagaatggc agagatcgga gagcatgtgg ccccgagcga ggcagcaaat | 1620 |
| tctcttgaac aggcccaggc agccgctgaa cggctggggt accctgtgct agtgcgtgca | 1680 |
| gcctttgccc tgggtggcct gggctctggc tttgcctcta caggagga gctctctgct | 1740 |
| ctcgtggccc cagcttttgc ccataccagc caagtgctag tagacaagtc tctgaaggga | 1800 |
| tggaaggaga ttgagtacga ggtggtgaga gacgccatg gcaactgtgt cacggtgtgt | 1860 |
| aacatggaga acttggaccc actgggcatc cacactggtg agtccatagt ggtggcccct | 1920 |
| agccagacac tgaatgacag ggagtatcag ctcctgaggc agacagctat caaggtgacc | 1980 |
| cagcacctgg gaattgttgg ggagtgcaat gtgcagtatg ccttgaaccc tgagtctgag | 2040 |
| cagtattaca tcattgaagt gaatgccagg ctctctcgca gctctgccct ggccagtaag | 2100 |
| gccacaggtt atccactggc ttatgtggca gccaagctag cattgggcat ccctttgcct | 2160 |
| gagctcagga actctgtgac aggggtaca gcagcctttg aacccagcgt ggattattgt | 2220 |
| gtggtgaaga ttcctcgatg ggaccttagc aagttcctgc gagtcagcac aaagattggg | 2280 |
| agctgcatga gagcgttgg tgaagtcatg gcattgggc gttcatttga ggaggccttc | 2340 |
| cagaaggccc tgcgcatggt ggatgagaac tgtgtgggct ttgatcacac agtgaaacca | 2400 |
| gtcagcgata tggagttgga gactccaaca gataagcgga tttttgtggt ggcagctgct | 2460 |
| ttgtgggctg gttattcagt ggaccgcctg tatgagctca cacgcatcga ccgctggttc | 2520 |
| ctgcaccgaa tgaagcgtat catcgcacat gcccagctgc tagaacaaca ccgtggacag | 2580 |
| cctttgccgc cagacctgct gcaacaggcc aagtgtcttg gcttctcaga caaacagatt | 2640 |
| gcccttgcag ttctgagcac agagctggct gttcgcaagc tgcgtcagga actgggatc | 2700 |
| tgtccagcag tgaaacagat tgacacagtt gcagctgagt ggccagccca gacaaattac | 2760 |
| ctatacctaa cgtattgggg caccaccat gacctcacct ttcgaacacc tcatgtccta | 2820 |
| gtccttggct ctggcgtcta ccgtattggc tctagcgttg aatttgactg gtgtgctgta | 2880 |
| ggctgcatcc agcagctccg aaagatggga tataagacca tcatggtgaa ctataaccca | 2940 |
| gagacagtca gcaccgacta tgacatgtgt gatcgactct actttgatga gatctctttt | 3000 |
| gaggtggtga tggacatcta tgagctcgag aaccctgaag tgtgatcct atccatgggt | 3060 |
| ggacagctgc ccaacaacat ggccatggcg ttgcatcggc agcagtgccg ggtgctgggc | 3120 |

```
acctcccctg aagccattga ctcggctgag aaccgtttca agttttcccg gctccttgac    3180
accattggta tcagccagcc tcagtggagg gagctcagtg acctcgagtc tgctcgccaa    3240
ttctgccaga ccgtggggta cccctgtgtg gtgcgcccct cctatgtgct gagcggtgct    3300
gctatgaatg tggcctacac ggatggagac ctggagcgct tcctgagcag cgcagcagcc    3360
gtctccaaag agcatcccgt ggtcatctcc aagttcatcc aggaggctaa ggagattgac    3420
gtggatgccg tggcctctga tggtgtggtg gcagccatcg ccatctctga gcatgtggag    3480
aatgcaggtg tgcattcagg tgatgcgacg ctggtgaccc ccccacaaga tatcactgcc    3540
aaaaccctgg agcggatcaa agccattgtg catgctgtgg gccaggagct acaggtcaca    3600
ggacccttca atctgcagct cattgccaag gatgaccagc tgaaagttat tgaatgcaac    3660
gtacgtgtct ctcgctcctt ccccttcgtt tccaagacac tgggtgtgga cctagtagcc    3720
ttggccacgc gggtcatcat gggggaagaa gtggaacctg tggggctaat gactggttct    3780
ggagtcgtgg gagtaaaggt gcctcagttc tccttctccc gcttggcggg tgctgacgtg    3840
gtgttgggtg tggaaatgac cagtactggg gaggtggccg gctttgggga gagccgctgt    3900
gaggcatacc tcaaggccat gctaagcact ggctttaaga tccccaagaa gaatatcctg    3960
ctgaccattg gcagctataa gaacaaaagc gagctgctcc caactgtgcg gctactggag    4020
agcctgggct acagcctcta tgccagtctc ggcacagctg acttctacac tgagcatggc    4080
gtcaaggtaa cagctgtgga ctggcacttt gaggaggctg tggatggtga gtgcccacca    4140
cagcggagca tcctggagca gctagctgag aaaaactttg agctggtgat taacctgtca    4200
atgcgtggag ctgggggccg gcgtctctct tcctttgtca ccaagggcta ccgcacccga    4260
cgcttggccg ctgacttctc cgtgccccta atcatcgata tcaagtgcac caaactcttt    4320
gtggaggccc taggccagat cgggccagcc cctcctttga aggtgcatgt tgactgtatg    4380
acctcccaaa agcttgtgcg actgccggga ttgattgatg tccatgtgca cctgcgggaa    4440
ccaggtggga cacataagga ggactttgct tcaggcacag ccgctgccct ggctggggt    4500
atcaccatgg tgtgtgccat gcctaatacc cggccccca tcattgacgc ccctgctctg    4560
gccctggccc agaagctggc agaggctggc gcccggtgcg actttgcgct attccttggg    4620
gcctcgtctg aaaatgcagg aaccttgggc accgtggccg ggtctgcagc cgggctgaag    4680
ctttacctca atgagacctt ctctgagctg cggctggaca cgctggtcca gtggatggag    4740
catttcgaga catggccctc ccacctcccc attgtggctc acgcagagca gcaaaccgtg    4800
gctgctgtcc tcatggtggc tcagctcact cagcgctcag tgcacatatg tcacgtggca    4860
cggaaggagg agatcctgct aattaaagct gcaaaggcac ggggcttgcc agtgacctgc    4920
gaggtggctc cccaccacct gttcctaagc catgatgacc tggagcgcct ggggcctggg    4980
aagggggagg tccggcctga gcttggctcc cgccaggatg tggaagccct gtgggagaac    5040
atggctgtca tcgactgctt tgcctcagac catgctcccc ataccttgga ggagaagtgt    5100
gggtccaggc ccccacctgg gttcccaggg ttagagacca tgctgccact actcctgacg    5160
gctgtaagcg agggccggct cagcctggac gacctgctgc agcgattgca ccacaatcct    5220
cggcgcatct ttcacctgcc cccgcaggag gacacctatg tggaggtgga tctggagcat    5280
gagtggacaa ttcccagcca catgcccttc tccaaggccc actggacacc ttttgaaggg    5340
cagaaagtga agggcaccgt ccgccgtgtg gtcctgcgag gggaggttgc ctatatcgat    5400
gggcaggttc tggtaccccc gggctatgga caggatgtac ggaagtggcc acaggggggct    5460
```

```
gttcctcagc tcccaccctc agccctgcc actagtgaga tgaccacgac acctgaaaga      5520
ccccgccgtg catcccagg gcttcctgat ggccgcttcc atctgccgcc ccgaatccat      5580
cgagcctccg acccaggttt gccagctgag gagccaaagg agaagtcctc tcggaaggta    5640
gccgagccag agctgatggg aaccctgat ggcacctgct accctccacc accagtaccg     5700
agacaggcat ctccccagaa cctggggacc cctggcttgc tgcaccccca gacctcaccc    5760
ctgctgcact cattagtggg ccaacatatc ctgtccgtcc agcagttcac caaggatcag    5820
atgtctcacc tgttcaatgt ggcacacaca ctgcgtatga tggtgcagaa ggagcggagc    5880
ctcgacatcc tgaaggggaa ggtcatggcc tccatgttct atgaagtgag cacacggacc    5940
agcagctcct ttgcagcagc catggcccgg ctgggaggtg ctgtgctcag cttctcggaa    6000 gcccacatcgt ccgtccagaa gggcgaatcc ctggctgact ccgtcagac catgagctgc     6060 tatgccgacg tcgtcgtgct ccggcacccc cagcctggag cagtggagct ggccgccaag    6120
cactgccgga ggccagtgat caatgctggg gatggggtcg agagcaccc cacccaggcc     6180 ctgctggaca tcttcaccat ccgtgaggag ctgggaactg tcaatggcat gacgatcacg    6240
atggtgggtg acctgaagca cggacgcaca gtacattccc tggcctgcct gctcacccag    6300
tatcgtgtca gcctgcgcta cgtggcacct cccagcctgc gcatgccacc cactgtgcgg    6360
gccttcgtgg cctcccgcgg caccaagcag gaggaattcg agagcattga ggaggcgctg   6420
cctgacactg atgtgctcta catgactcga atccagaagg aacgatttgg ctctacccag    6480
gagtacgaag cttgctttgg tcagttcatc ctcactcccc acatcatgac ccgggccaag    6540
aagaagatgg tggtgatgca cccgatgccc cgtgtcaacg agataagcgt ggaagtggac    6600
tcggatcccc gcgcagccta cttccgccag gctgagaacg gcatgtacat ccgcatggct    6660
ctgttagcca ccgtgctggg ccgtttctag gcggccgcat cc                        6702

<210> SEQ ID NO 6
<211> LENGTH: 418
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gctagaattc gtatggcggc cctagtgttg gaggacgggt cggtcctgcg gggccagccc      60
tttggggccg ccgtgtcgac tgccggggaa gtggtgtttc aaaccggcat ggtcggctac    120
cccgaggccc tcactgatcc ctcctacaag gcacagatct tagtgctcac ctatcctctg    180
atcggcaact atggcatccc cccagatgaa atggatgagt tcggtctctg caagtggttt    240
gaatcctcgg gcatccacgt agcagcactg gtagtgggaa agtgctgtcc tactcccagc    300
cactggagtg ccacccgcac cctgcatgag tggctgcagc agcatggcat ccctggcttg    360
caaggagtag acactcggga gctgaccaag aagttgcggg aacagggcgg ccgcatcc      418

<210> SEQ ID NO 7
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gctagaattc gtggtctctg ctggggaagc tggtccagaa tggaacagaa ccttcatccc      60
```

```
tgccattctt ggaccccaat gcccgccccc tggtaccaga ggtctccatt aagactccac      120
gggtattcaa tacagggggt gcccctcgga tccttgcttt ggactgtggc ctcaagtata      180
atcagatccg atgcctctgc cagcgtgggg ctgaggtcac tgtggtaccc tgggaccatg      240
cactagacag ccaagagtat gagggtctct tcttaagtaa tgggcctggt gaccctgcct      300
cctatcccag tgtcgtatcc acactgagcc gtgttttatc tgagcctaat ccccgacctg      360
tctttgggat ctgcctggga caccagctat tggcctfagc cattgggcc aagacttaca       420 agatgagata tgggaaccga ggccataacc agccctgctt gttggtgggc tctggcgct       480 gctttctgac atcccagaac catgggtttg ctgtggagac agactcactg ccagcagact      540
gggctcctct cttccaac gccaatgatg gttccaatga aggcattgtg cacaacagct        600
tgcctttctt cagtgtccag tttcacccag agcaccaagc tggcccttca gatatggaac      660
tgcttttcga tatctttctg gaaactgtga agaggccac agctgggaac cctggggggcc      720 agacagttag agagcggctg actgagcgcc tctgtccccc tgggattccc actcccggct      780
ctggacttcc accaccacga aaggttctga tcctgggctc aggggggcctc tccattggcc     840 aagctggaga atttgactac tcgggctctc aggcaattaa ggccctgaag gaggaaaaca      900
tccagacgtt gctgatcaac cccaatattg ccacagtgca gacctcccag gggctggccg      960
acaaggtcta ttttcttccc ataacacctc attatgtaac ccaggtgata cgtaatgaac     1020
gccccgatgg tgtgttactg acttttgggg gccagactgc tctgaactgt ggtggcggcc     1080
gcatcc                                                                1086

<210> SEQ ID NO 8
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gctagaattc gttggagctg accaaggccg gggtgctggc tcggtatggg gtccgggtcc       60
tgggcacacc agtggagacc attgagctga ccgaggatcg acgggccttt gctgccagaa      120 tgcagagat cggagagcat gtggccccga gcgaggcagc aaattctctt gaacaggccc       180
aggcagccgc tgaacggctg gggtaccctg tgctagtgcg tgcagccttt gccctgggtg      240
gcctgggctc tggctttgcc tctaacaggg aggagctctc tgctctcgtg gccccagctt      300
ttgcccatac cagccaagtg ctagtagaca agtctctgaa gggatggaag gagattgagt      360
acgaggtggt gagagacggc ggccgcatcc                                       390

<210> SEQ ID NO 9
<211> LENGTH: 4874
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gctagaattc gtcctatggc aactgtgtca cggtgtgtaa catggagaac ttggacccac       60
tgggcatcca cactggtgag tccatagtgg tggcccctag ccagacactg aatgacaggg      120
agtatcagct cctgaggcag acagctatca aggtgaccca gcacctggga attgttgggg      180
```

```
agtgcaatgt gcagtatgcc ttgaaccctg agtctgagca gtattacatc attgaagtga    240
atgccaggct ctctcgcagc tctgccctgg ccagtaaggc cacaggttat ccactggctt    300
atgtggcagc caagctagca ttgggcatcc ctttgcctga gctcaggaac tctgtgacag    360
ggggtacagc agcctttgaa cccagcgtgg attattgtgt ggtgaagatt cctcgatggg    420
accttagcaa gttcctgcga gtcagcacaa agattgggag ctgcatgaag agcgttggtg    480
aagtcatggg cattgggcgt tcatttgagg aggccttcca gaaggccctg cgcatggtgg    540
atgagaactg tgtgggcttt gatcacacag tgaaaccagt cagcgatatg gagttggaga    600
ctccaacaga taagcggatt tttgtggtgg cagctgcttt gtgggctggt tattcagtgg    660
accgcctgta tgagctcaca cgcatcgacc gctggttcct gcaccgaatg aagcgtatca    720
tcgcacatgc ccagctgcta aacaacacc gtggacagcc tttgccgcca gacctgctgc    780
aacaggccaa gtgtcttggc ttctcagaca aacagattgc ccttgcagtt ctgagcacag    840
agctggctgt tcgcaagctg cgtcaggaac tggggatctg tccagcagtg aaacagattg    900
acacagttgc agctgagtgg ccagcccaga caaattacct ataccctaacg tattgggca    960 ccacccatga cctcaccttt cgaacacctc atgtcctagt ccttggctct ggcgtctacc   1020
gtattggctc tagcgttgaa tttgactggt gtgctgtagg ctgcatccag cagctccgaa   1080
agatgggata taagaccatc atggtgaact ataacccaga gacagtcagc accgactatg   1140
acatgtgtga tcgactctac tttgatgaga tctcttttga ggtggtgatg gacatctatg   1200
agctcgagaa ccctgaaggt gtgatcctat ccatgggtgg acagctgccc aacaacatgg   1260
ccatggcgtt gcatcggcag cagtgccggg tgctgggcac ctccctgaa gccattgact   1320 cggctgagaa ccgtttcaag ttttcccggc tccttgacac cattggtatc agccagcctc   1380
agtggaggga gctcagtgac ctcgagtctg ctcgccaatt ctgccagacc gtggggtacc   1440
cctgtgtggt gcgcccctcc tatgtgctga gcggtgctgc tatgaatgtg gcctacacgg   1500
atggagacct ggagcgcttc ctgagcagcg cagcagccgt ctccaaagag catcccgtgg   1560
tcatctccaa gttcatccag gaggctaagg agattgacgt ggatgccgtg gcctctgatg   1620
gtgtggtggc agccatcgcc atctctgagc atgtggagaa tgcaggtgtg cattcaggtg   1680
atgcgacgct ggtgaccccc ccacaagata tcactgccaa aaccctggag cggatcaaag   1740
ccattgtgca tgctgtgggc caggagctac aggtcacagg acccttcaat ctgcagctca   1800
ttgccaagga tgaccagctg aaagttattg aatgcaacgt acgtgtctct cgctccttcc   1860
ccttcgtttc caagacactg ggtgtggacc tagtagcctt ggccacgcgg gtcatcatgg   1920
gggaagaagt ggaacctgtg gggctaatga ctggttctgg agtcgtggga gtaaaggtgc   1980
ctcagttctc cttctcccgc ttggcggggtg ctgacgtggt gttgggtgtg gaaatgacca   2040
gtactgggga ggtggccggc tttggggaga gccgctgtga ggcataccct caaggccatgc   2100 taagcactgg ctttaagatc cccaagaaga atatcctgct gaccattggc agctataaga   2160
acaaaagcga gctgctccca actgtgcggc tactggagag cctgggctac agcctctatg   2220
ccagtctcgg cacagctgac ttctacactg agcatggcgt caaggtaaca gctgtggact   2280
ggcactttga ggaggctgtg gatggtgagt gccaccaca gcggagcatc ctggagcagc   2340
tagctgagaa aaactttgag ctggtgatta acctgtcaat gcgtggagct ggggggccggc   2400 gtctctcttc ctttgtcacc aagggctacc gcacccgacg cttggccgct gacttctccg   2460
tgcccctaat catcgatatc aagtgcacca aactctttgt ggaggcccta ggccagatcg   2520
ggccagcccc tcctttgaag gtgcatgttg actgtatgac ctcccaaaag cttgtgcgac   2580
```

```
tgccgggatt gattgatgtc catgtgcacc tgcgggaacc aggtgggaca cataaggagg    2640
actttgcttc aggcacagcc gctgccctgg ctgggggtat caccatggtg tgtgccatgc    2700
ctaatacccg gccccccatc attgacgccc ctgctctggc cctggcccag aagctggcag    2760
aggctggcgc ccggtgcgac tttgcgctat tccttggggc ctcgtctgaa aatgcaggaa    2820
ccttgggcac cgtggccggg tctgcagccg ggctgaagct ttacctcaat gagaccttct    2880
ctgagctgcg gctggacagc gtggtccagt ggatggagca tttcgagaca tggccctccc    2940
acctccccat tgtggctcac gcagagcagc aaaccgtggc tgctgtcctc atggtggctc    3000
agctcactca gcgctcagtg cacatatgtc acgtggcacg gaaggaggag atcctgctaa    3060
ttaaagctgc aaaggcacgg ggcttgccag tgacctgcga ggtggctccc caccacctgt    3120
tcctaagcca tgatgacctg gagcgcctgg ggcctgggaa gggggaggtc cggcctgagc    3180
ttggctcccg ccaggatgtg gaagccctgt gggagaacat ggctgtcatc gactgctttg    3240
cctcagacca tgctccccat accttggagg agaagtgtgg gtccaggccc ccacctgggt    3300
tcccagggtt agagaccatg ctgccactac tcctgacggc tgtaagcgag ggccggctca    3360
gcctggacga cctgctgcag cgattgcacc acaatcctcg gcgcatcttt cacctgcccc    3420
cgcaggagga cacctatgtg gaggtggatc tggagcatga gtggacaatt cccagccaca    3480
tgcccttctc caaggcccac tggacacctt ttgaagggca gaaagtgaag ggcaccgtcc    3540
gccgtgtggt cctgcgaggg gaggttgcct atatcgatgg gcaggttctg gtaccccgg    3600 gctatggaca ggatgtacgg aagtggccac aggggctgt tcctcagctc ccaccctcag    3660
cccctgccac tagtgagatg accacgacac ctgaaagacc ccgccgtggc atcccagggc    3720
ttcctgatgg ccgcttccat ctgccgcccc gaatccatcg agcctccgac ccaggtttgc    3780
cagctgagga gccaaaggag aagtcctctc ggaaggtagc cgagccagag ctgatgggaa    3840
cccctgatgg cacctgctac cctccaccac cagtaccgag acaggcatct ccccagaacc    3900
tggggacccc tggcttgctg cacccccaga cctcacccct gctgcactca ttagtgggcc    3960
aacatatcct gtccgtccag cagttcacca aggatcagat gtctcacctg ttcaatgtgg    4020
cacacacact gcgtatgatg gtgcagaagg agcggagcct cgacatcctg aaggggaagg    4080
tcatggcctc catgttctat gaagtgagca cacggaccag cagctccttt gcagcagcca    4140 tggccccggct gggaggtgct gtgctcagct tctcggaagc cacatcgtcc gtccagaagg    4200
gcgaatccct ggctgactcc gtgcagacca tgagctgcta tgccgacgtc gtcgtgctcc    4260
ggcaccccca gcctggagca gtggagctgg ccgccaagca ctgccggagg ccagtgatca    4320
atgctgggga tggggtcgga gagcacccca cccaggccct gctggacatc ttcaccatcc    4380
gtgaggagct gggaactgtc aatggcatga cgatcacgat ggtgggtgac ctgaagcacg    4440
gacgcacagt acattccctg gcctgcctgc tcacccagta tcgtgtcagc ctgcgctacg    4500
tggcacctcc cagcctgcgc atgccaccca ctgtgcgggc cttcgtgcc tcccgcggca    4560 ccaagcagga ggaattcgag agcattgagg aggcgctgcc tgacactgat gtgctctaca    4620
tgactcgaat ccagaaggaa cgatttggct ctacccagga gtacgaagct tgctttggtc    4680
agttcatcct cactccccac atcatgaccc gggccaagaa gaagatggtg gtgatgcacc    4740
cgatgccccg tgtcaacgag ataagcgtgg aagtggactc ggatccccgc gcagcctact    4800
tccgccaggc tgagaacggc atgtacatcc gcatggctct gttagccacc gtgctgggcc    4860
gtttctagca attg                                                     4874
```

```
<210> SEQ ID NO 10
<211> LENGTH: 11929
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| ctcgagccac | catggccgcg | caggtcgccc | ccgccgccgc | cagcagcctg | gcaacccgc | 960 |
| cgccgccgcc | gccctcggag | ctgaagaaag | ccgagcagca | gcagcgggag | gaggcggggg | 1020 |
| gcgaggcggc | ggcggcggca | gcggccgagc | gcggggaaat | gaaggcagcc | gccgggcagg | 1080 |
| aaagcgaggg | ccccgccgtg | gggccgccgc | agcgctgggg | aaaggagctg | caggacgggg | 1140 |
| ccgagagcaa | tgggggtggc | ggcggcggcg | gagccggcag | cggcggcggg | ccggcgcgg | 1200 |
| agccggacct | gaagaactcg | aacgggaacg | cgggccctag | gccgcccctg | aacaataacc | 1260 |
| tcacggagcc | gccccggcgg | ggcggtgcg | gcagcagcga | tgggggtggg | gcgcctcctc | 1320 |
| actcagccgc | ggccgccttg | ccgccccag | cctacggctt | cgggcaaccc | tacggccgga | 1380 |
| gcccgtctgc | cgtcgccgcc | gccgcggcg | ccgtcttcca | ccaacaacat | ggcggacaac | 1440 |
| aaagccctgg | cctggcagcg | ctgcagagcg | gcggcggcgg | gggcctggag | ccctacgcgg | 1500 |
| ggccccagca | gaactctcac | gaccacggct | tccccaacca | ccagtacaac | tcctactacc | 1560 |
| ccaaccgcag | cgcctacccc | ccgcccgccc | cggcctacgc | gctgagctcc | ccgagaggtg | 1620 |
| gcactccggg | ctccgcgcg | gcggcggctg | ccggctccaa | gccgcctccc | tcctccagcg | 1680 |
| cctccgcctc | ctcgtcgtct | tcgtccttcg | ctcagcagcg | cttcggggcc | atgggggag | 1740 |
| gcggcccctc | cgcggccggc | gggggaactc | cccagcccac | cgccaccccc | accctcaacc | 1800 |
| aactgctcac | gtcgcccagc | tcggcccggg | gctaccaggg | ctaccccggg | ggcgactaca | 1860 |
| gtggcgggcc | ccaggacggg | ggcgccggca | agggcccggc | ggacatggcc | tcgcagtgtt | 1920 |
| gggggggctgc | ggcggcggca | gctgcggcgg | cggccgcctc | gggagggcc | caacaaagga | 1980 |
| gccaccacgc | gcccatgagc | cccggagca | gcggcggcgcg | ggggcagccg | ctcgcccgga | 2040 |

-continued

```
cccctcagcc atccagtcca atggatcaga tgggcaagat gagacctcag ccatatggcg   2100
ggactaaccc atactcgcag caacagggac ctccgtcagg accgcagcaa ggacatgggt   2160
acccagggca gccatacggg tcccagaccc cgcagcggta cccgatgacc atgcagggcc   2220
gggcgcagag tgccatgggc ggcctctctt atacacagca gattcctcct tatggacaac   2280 aaggcccag cgggtatggt caacagggcc agactccata ttacaaccag caaagtcctc   2340
accctcagca gcagcagcca ccctactccc agcaaccacc gtcccagacc cctcatgccc   2400
aaccttcgta tcagcagcag ccacagtctc aaccaccaca gctccagtcc tctcagcctc   2460
catactccca gcagccatcc cagcctccac atcagcagtc cccggctcca tacccctccc   2520
agcagtcgac gacacagcag caccccagga gccagccccc ctactcacag ccacaggctc   2580
agtctcctta ccagcagcag caacctcagc agccagcacc ctcgacgctc tcccagcagg   2640
ctgcgtatcc tcagcccag tctcagcagt cccagcaaac tgcctattcc cagcagcgct   2700
tccctccacc gcaggagcta tctcaagatt catttgggtc tcaggcatcc tcagccccct   2760
caatgacctc cagtaaggga gggcaagaag atatgaacct gagccttcag tcaagaccct   2820
ccagcttgcc tgatctatct ggttcaatag atgacctccc catggggaca gaaggagctc   2880
tgagtcctgg agtgagcaca tcagggattt ccagcagcca aggagagcag agtaatccag   2940
ctcagtctcc tttctctcct catacctccc ctcacctgcc tggcatccga ggcccttccc   3000 cgtccctgt tggctctccc gccagtgttg ctcagtctcg ctcaggacca ctctcgcctg   3060
ctgcagtgcc aggcaaccag atgccacctc ggccacccag tggccagtcg acagcatca   3120 tgcatccttc catgaaccaa tcaagcattg cccaagatcg aggttatatg cagaggaacc   3180
cccagatgcc ccagtacagt tccccccagc ccggctcagc cttatctccg cgtcagcctt   3240
ccggaggaca gatacacaca ggcatgggct cctaccagca gaactccatg ggagctatg   3300 gtccccaggg gggtcagtat ggcccacaag gtggctaccc caggcagcca aactataatg   3360
ccttgcccaa tgccaactac cccagtgcag gcatggctgg aggcataaac cccatgggtg   3420
ccggaggtca aatgcatgga cagcctggca tcccaccttta tggcacactc cctccaggga   3480
ggatgagtca cgcctccatg ggcaaccggc cttatggccc taacatggcc aatatgccac   3540
ctcaggttgg gtcagggatg tgtccccac caggggggcat gaaccggaaa acccaagaaa   3600
ctgctgtcgc catgcatgtt gctgccaact ctatccaaaa caggccgcca ggctacccca   3660
atatgaatca agggggcatg atgggaactg gacctcctta tggacaaggg attaatagta   3720
tggctggcat gatcaaccct cagggacccc catattccat gggtggaacc atggccaaca   3780
attctgcagg gatggcagcc agcccagaga tgatgggcct tggggatgta aagttaactc   3840
cagccaccaa aatgaacaac aaggcagatg ggacacccaa gacagaatcc aaatccaaga   3900
aatccagttc ttctactaca accaatgaga agatcaccaa gttgtatgag ctgggtggtg   3960
agcctgagag gaagatgtgg gtggaccgtt atctggcctt cactgaggag aaggccatgg   4020
gcatgacaaa tctgcctgct gtgggtagga acctctgga cctctatcgc ctctatgtgt   4080
ctgtgaagga gattggtgga ttgactcagg tcaacaagaa caaaaaatgg cgggaacttg   4140
caaccaacct caatgtgggc acatcaagca gtgctgccag ctccttgaaa aagcagtata   4200
tccagtgtct ctatgccttt gaatgcaaga ttgaacgggg agaagaccct ccccagaca   4260 tctttgcagc tgctgattcc aagaagtccc agcccaagat ccagcctccc tctcctgcgg   4320
gatcaggatc tatgcagggg ccccagactc cccagtcaac cagcagttcc atggcagaag   4380
gaggagactt aaagccacca actccagcat ccacaccaca cagtcagatc cccccattgc   4440
```

```
caggcatgag caggagcaat tcagttggga tccaggatgc ctttaatgat ggaagtgact    4500
ccacattcca gaagcggaat tccatgactc caaaccctgg gtatcagccc agtatgaata    4560
cctctgacat gatgggcgc atgtcctatg agccaaataa ggatccttat ggcagcatga    4620
ggaaagctcc agggagtgat cccttcatgt cctcagggca gggccccaac ggcgggatgg    4680
gtgaccccta cagtcgtgct gccggccctg gctaggaaa tgtggcgatg ggaccacgac    4740
agcactatcc ctatggaggt ccttatgaca gagtgaggac ggagcctgga atagggcctg    4800
agggaaacat gagcactggg gccccacagc cgaatctcat gccttccaac ccagactcgg    4860
ggatgtattc tcctagccgc tacccccgc agcagcagca gcagcagcag caacgacatg    4920
attcctatgg caatcagttc tccacccaag gcacccttc tggcagcccc ttccccagcc    4980
agcagactac aatgtatcaa cagcaacagc agaattacaa gcggccaatg gatggcacat    5040
atggccctcc tgccaagcgg cacgaagggg agatgtacag cgtgccatac agcactgggc    5100
aggggcagcc tcagcagcag cagttgcccc cagcccagcc ccagcctgcc agccagcaac    5160
aagctgccca gccttcccct cagcaagatg tatacaacca gtatggcaat gcctatcctg    5220
ccactgccac agctgctact gagcgccgac cagcaggcgg cccccagaac caatttccat    5280
tccagtttgg ccgagaccgt gtctctgcac cccctggcac caatgcccag caaaacatgc    5340
caccacaaat gatgggcggc cccatacagg catcagctga ggttgctcag caaggcacca    5400
tgtggcaggg gcgtaatgac atgacctata attatgccaa caggcagagc acgggctctg    5460
ccccccaggg ccccgcctat catggcgtga accgaacaga tgaaatgctg cacacagatc    5520
agagggccaa ccacgaaggc tcgtggcctt cccatggcac acgccagccc ccatatggtc    5580
cctctgcccc tgtgcccccc atgacaaggc cccctccatc taactaccag cccccaccaa    5640
gcatgcagaa tcacattcct caggtatcca gccctgctcc cctgccccgg ccaatggaga    5700
accgcacctc tcctagcaag tctccattcc tgcactctgg gatgaaaatg cagaaggcag    5760
gtcccccagt acctgcctcg cacatagcac ctgcccctgt gcagccccc atgattcggc    5820 gggatatcac cttccacct ggctctgttg aagccacaca gctgtgttg aagcagagga    5880 ggcggctcac aatgaaagac attggaaccc cggaggcatg gcgggtaatg atgtccctca    5940
agtctggtct cctggcagag agcacatggg cattagatac catcaacatc ctgctgtatg    6000
atgacaacag catcatgacc ttcaacctca gtcagctccc agggttgcta gagctccttg    6060
tagaatattt ccgacgatgc ctgattgaga tctttggcat tttaaaggag tatgaggtgg    6120
gtgacccagg acagagaacg ctactggatc ctgggaggtt cagcaaggtg tctagtccag    6180
ctcccatgga gggtgggggaa gaagaagaag aacttctagg tcctaaacta gaagaggaag    6240
aagaaggaga agtagttgaa aatgatgagg agatagcctt tcaggcaag gacaagccag    6300 cttcagagaa tagtgaggag aagctgatca gtaagtttga caagcttcca gtaaagatcg    6360
tacagaagaa tgatccattt gtggtggact gctcagataa gcttgggcgt gtgcaggagt    6420
ttgacagtgg cctgctgcac tggcggattg gtgggggga caccactgag catatccaga    6480
cccacttcga gagcaagaca gagctgctgc cttcccggcc tcacgcaccc tgcccaccag    6540
cccctcggaa gcatgtgaca acagcagagg gtacaccagg acaacagac caggaggggc    6600 ccccacctga tggacctcca gaaaaacgga tcacagccac tatggatgac atgttgtcta    6660
ctcggtctag caccttgacc gaggatggag ctaagagttc agaggccatc aaggagagca    6720
gcaagtttcc atttggcatt agcccagcac agagccaccg gaacatcaag atcctagagg    6780
```

```
acgaacccca cagtaaggat gagaccccac tgtgtaccct tctggactgg caggattctc    6840
ttgccaagcg ctgcgtctgt gtgtccaata ccattcgaag cctgtcattt gtgccaggca    6900
atgactttga gatgtccaaa cacccagggc tgctgctcat cctgggcaag ctgatcctgc    6960
tgcaccacaa gcacccagaa cggaagcagg caccactaac ttatgaaaag gaggaggaac    7020
aggaccaagg ggtgagctgc aacaaagtgg agtggtggtg ggactgcttg gagatgctcc    7080
gggaaaacac cttggttaca ctcgccaaca tctcggggca gttggaccta tctccatacc    7140
ccgagagcat ttgcctgcct gtcctggacg gactcctaca ctgggcagtt tgcccttcag    7200
ctgaagccca ggacccctt tccaccctgg gccccaatgc cgtcctttcc ccgcagagac     7260
tggtcttgga aaccctcagc aaactcagca tccaggacaa caatgtggac ctgattctgg    7320
ccacaccccc cttcagccgc ctggagaagt tgtatagcac tatggtgcgc ttcctcagtg    7380
accgaaagaa cccggtgtgc cgggagatgg ctgtggtact gctggccaac ctggctcagg    7440
gggacagcct ggcagctcgt gccattgcag tgcagaaggg cagtatcggc aacctcctgg    7500
gcttcctaga ggacagcctt gccgccacac agttccagca gagccaggcc agcctcctcc    7560
acatgcagaa cccacccttt gagccaacta gtgtggacat gatgcggcgg gctgcccgcg    7620
cgctgcttgc cttggccaag gtggacgaga accactcaga gtttactctg tacgaatcac    7680
ggctgttgga catctcggta tcaccgttga tgaactcatt ggtttcacaa gtcatttgtg    7740
atgtactgtt tttgattggc cagtcctcga gtctagaggg cccgcggttc gaaggtaagc    7800
ctatccctaa ccctctcctc ggtctcgatt ctacgcgtac cggtcatcat caccatcacc    7860
attgagttta aacccgctga tcagcctcga ctgtgccttc tagttgccag ccatctgttg    7920
tttgcccctc cccgtgcctt ccttgaccc tggaaggtgc cactcccact gtcctttcct     7980
aataaaatga ggaaattgca tcgcattgtc tgagtaggtg tcattctatt ctggggggtg    8040
gggtggggca ggacagcaag ggggaggatt gggaagacaa tagcaggcat gctggggatg    8100
cggtgggctc tatggcttct gaggcggaaa gaaccagctg gggctctagg gggtatcccc    8160
acgcgccctg tagcggcgca ttaagcgcgg cgggtgtggt ggttacgcgc agcgtgaccg    8220
ctacacttgc cagcgcccta gcgcccgctc ctttcgcttt cttcccttcc tttctcgcca    8280
cgttcgccgg ctttccccgt caagctctaa atcgggggct ccctttaggg ttccgattta    8340
gtgctttacg gcacctcgac cccaaaaaac ttgattaggg tgatggttca cgtagtgggc    8400
catcgccctg atagacggtt tttcgccctt tgacgttgga gtccacgttc tttaatagtg    8460
gactcttgtt ccaaactgga acaacactca accctatctc ggtctattct tttgatttat    8520
aagggatttt gccgatttcg gcctattggt taaaaaatga gctgatttaa caaaaattta    8580
acgcgaatta ttctgtggaa atgtgtgtca gttagggtgt ggaaagtccc caggctcccc    8640
agcaggcaga agtatgcaaa gcatgcatct caattagtca gcaaccaggt gtggaaagtc    8700
cccaggctcc ccagcaggca gaagtatgca aagcatgcat ctcaattagt cagcaaccat    8760
agtcccgccc ctaactccgc ccatcccgcc cctaactccg cccagttccg cccattctcc    8820
gccccatggc tgactaattt tttttattta tgcagaggcc gaggccgcct ctgcctctga    8880
gctattccag aagtagtgag gaggcttttt tggaggccta ggcttttgca aaaagctccc    8940
gggagcttgt atatccattt tcggatctga tcagcacgtg ttgacaatta atcatcggca    9000
tagtatatcg gcatagtata atacgacaag gtgaggaact aaaccatggc caagcctttg    9060
tctcaagaag aatccaccct cattgaaaga gcaacggcta caatcaacag catccccatc    9120
tctgaagact acagcgtcgc cagcgcagct ctctctagcg acggccgcat cttcactggt    9180
```

```
gtcaatgtat atcattttac tgggggacct tgtgcagaac tcgtggtgct gggcactgct    9240
gctgctgcgg cagctggcaa cctgacttgt atcgtcgcga tcggaaatga aacaggggc     9300
atcttgagcc cctgcggacg gtgccgacag gtgcttctcg atctgcatcc tgggatcaaa    9360
gccatagtga aggacagtga tggacagccg acggcagttg ggattcgtga attgctgccc    9420
tctggttatg tgtgggaggg ctaagcactt cgtggccgag gagcaggact gacacgtgct    9480
acgagatttc gattccaccg ccgccttcta tgaaaggttg ggcttcggaa tcgtttccg     9540
ggacgccggc tggatgatcc tccagcgcgg ggatctcatg ctggagttct tcgcccaccc    9600
caacttgttt attgcagctt ataatggtta caaataaagc aatagcatca caaatttcac    9660
aaataaagca ttttttcac  tgcattctag ttgtggtttg tccaaactca tcaatgtatc    9720
ttatcatgtc tgtataccgt cgacctctag ctagagcttg gcgtaatcat ggtcatagct    9780
gtttcctgtg tgaaattgtt atccgctcac aattccacac aacatacgag ccggaagcat    9840
aaagtgtaaa gcctggggtg cctaatgagt gagctaactc acattaattg cgttgcgctc    9900
actgcccgct ttccagtcgg gaaacctgtc gtgccagctg cattaatgaa tcggccaacg    9960
cgcggggaga ggcggtttgc gtattgggcg ctcttccgct tcctcgctca ctgactcgct   10020
gcgctcggtc gttcggctgc ggcgagcggt atcagctcac tcaaaggcgg taatacggtt   10080
atccacagaa tcaggggata acgcaggaaa gaacatgtga gcaaaaggcc agcaaaaggc   10140
caggaaccgt aaaaaggccg cgttgctggc gtttttccat aggctccgcc cccctgacga   10200
gcatcacaaa aatcgacgct caagtcgag  gtggcgaaac ccgacaggac tataaagata   10260
ccaggcgttt ccccctggaa gctccctcgt gcgctctcct gttccgaccc tgccgcttac   10320
cggatacctg tccgcctttc tcccttcggg aagcgtggcg ctttctcata gctcacgctg   10380
taggtatctc agttcggtgt aggtcgttcg ctccaagctg ggctgtgtgc acgaaccccc   10440
cgttcagccc gaccgctgcg ccttatccgg taactatcgt cttgagtcca acccggtaag   10500
acacgactta tcgccactgg cagcagccac tggtaacagg attagcagag cgaggtatgt   10560
aggcggtgct acagagttct tgaagtggtg gcctaactac ggctacacta agaacagt    10620
atttggtatc tgcgctctgc tgaagccagt taccttcgga aaaagagttg gtagctcttg   10680
atccggcaaa caaccaccg  ctggtagcgg tggtttttt  gtttgcaagc agcagattac   10740
gcgcagaaaa aaaggatctc aagaagatcc tttgatcttt tctacggggt ctgacgctca   10800
gtggaacgaa aactcacgtt aagggatttt ggtcatgaga ttatcaaaaa ggatcttcac   10860
ctagatcctt ttaaattaaa aatgaagttt taaatcaatc taaagtatat atgagtaaac   10920
ttggtctgac agttaccaat gcttaatcag tgaggcacct atctcagcga tctgtctatt   10980
tcgttcatcc atagttgcct gactccccgt cgtgtagata actacgatac gggagggctt   11040
accatctggc cccagtgctg caatgatacc gcgagaccca cgctcaccgg ctccagattt   11100
atcagcaata accagccag  ccggaagggc cgagcgcaga agtggtcctg caactttatc   11160
cgcctccatc cagtctatta attgttgccg ggaagctaga gtaagtagtt cgccagttaa   11220
tagtttgcgc aacgttgttg ccattgctac aggcatcgtg gtgtcacgct cgtcgtttgg   11280
tatggcttca ttcagctccg gttcccaacg atcaaggcga gttacatgat cccccatgtt   11340
gtgcaaaaaa gcggttagct ccttcggtcc tccgatcgtt gtcagaagta agttggccgc   11400
agtgttatca ctcatggtta tggcagcact gcataattct cttactgtca tgccatccgt   11460
aagatgcttt tctgtgactg gtgagtactc aaccaagtca ttctgagaat agtgtatgcg   11520
```

```
gcgaccgagt tgctcttgcc cggcgtcaat acgggataat accgcgccac atagcagaac      11580
tttaaaagtg ctcatcattg gaaaacgttc ttcggggcga aaactctcaa ggatcttacc      11640
gctgttgaga tccagttcga tgtaacccac tcgtgcaccc aactgatctt cagcatcttt      11700
tactttcacc agcgtttctg ggtgagcaaa acaggaagg caaaatgccg caaaaaaggg       11760
aataagggcg acacggaaat gttgaatact catactcttc cttttcaat attattgaag       11820 catttatcag ggttattgtc tcatgagcgg atacatattt gaatgtattt agaaaaataa      11880
acaaataggg gttccgcgca catttccccg aaaagtgcca cctgacgtc                  11929
```

<210> SEQ ID NO 11
<211> LENGTH: 6829
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gacggatcgg agatctcccc gatcccctat ggtgcactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacgggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc       420
attgacgtca atgggtggag tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggactttcca aaatgtcgta acaactccgc cccattgacg caaatgggcg       780
gtaggcgtgt acggtgggag gtctatataa gcagagctct ctggctaact agagaaccca       840
ctgcttactg gcttatcgaa attaatacga ctcactatag ggagacccaa gctggctagc       900
ctcgagccac catggccgcg caggtcgccc ccgccgccgc cagcagcctg gcaacccgc        960 cgccgccgcc gccctcggag ctgaagaaag ccgagcagca gcagcgggag gaggcggggg      1020
gcgaggcggc ggcggcggca gcggccgagc gcggggaaat gaaggcagcc gccgggcagg      1080
aaagcgaggg ccccgccgtg gggccgccgc agcgctgggg aaaggagctg caggacgggg      1140
ccgagagcaa tgggggtggc ggcggcggcg gagccggcag cggcggcggg ccggcgcgg       1200 agccggaccct gaagaactcg aacgggaacg cgggccctag gccgcccctg aacaataacc      1260
tcacggagcc gccccggcgg cggcggtggcg gcagcagcga tggggtgggg gcgcctcctc     1320
actcagccgc ggccgccttg ccgccccag cctacggctt cggcaaccc tacggccgga       1380 gcccgtctgc cgtcgccgcc gccgcggccg ccgtcttcca ccaacaacat ggcggacaac     1440
aaagccctgg cctggcagcg ctgcagagcg gcggcggcgg gggcctggag ccctacgcgg     1500 ggcccccagca gaactctcac gaccacggct tccccaacca ccagtacaac tcctactacc     1560
ccaaccgcag cgcctacccc ccgccgccc cggcctacgc gctgagctcc ccgagaggtg     1620
```

```
gcactccggg ctccggcgcg gcggcggctg ccggctccaa gccgcctccc tcctccagcg    1680
cctccgcctc ctcgtcgtct tcgtccttcg ctcagcagcg cttcgggcc atggggggag     1740 gcggcccctc cgcggccggc gggggaactc cccagcccac cgccaccccc accctcaacc    1800
aactgctcac gtcgcccagc tcggcccggg gctaccaggg ctaccccggg ggcgactaca    1860
gtggcgggcc ccaggacggg ggcgccggca agggcccggc ggacatggcc tcgcagtgtt    1920 gggggggctgc ggcggcggca gctgcggcgg cggccgcctc gggaggggcc caacaaagga   1980
gccaccacgc gcccatgagc cccgggagca gcggcggcgg ggggcagccg ctcgcccgga    2040
cccctcagcc atccagtcca atggatcaga tgggcaagat gagacctcag ccatatggcg    2100
ggactaaccc atactcgcag caacagggac ctccgtcagg accgcagcaa ggacatgggt    2160
acccagggca gccatacggg tcccagaccc cgcagcggta cccgatgacc atgcagggcc    2220
gggcgcagag tgccatgggc ggcctctctt atacacagca gattcctcct tatggacaac    2280
aaggccccag cgggtatggt caacagggcc agactccata ttacaaccag caaagtcctc    2340
accctcagca gcagcagcca ccctactccc agcaaccacc gtcccagacc cctcatgccc    2400
aaccttcgta tcagcagcag ccacagtctc aaccaccaca gctccagtcc tctcagcctc    2460
catactccca gcagccatcc cagcctccac atcagcagtc cccggctcca taccctcccc    2520
agcagtcgac gacacagcag cacccccaga gccagccccc ctactcacag ccacaggctc    2580
agtctcctta ccagcagcag caacctcagc agccagcacc ctcgacgctc tcccagcagg    2640
ctgcgtatcc tcagccccag tctcagcaga gtctagaggg cccgcggttc gaaggtaagc    2700
ctatccctaa ccctctcctc ggtctcgatt ctacgcgtac cggtcatcat caccatcacc    2760
attgagttta aacccgctga tcagcctcga ctgtgccttc tagttgccag ccatctgttg    2820
tttgcccctc cccgtgcct tccttgaccc tggaaggtgc cactcccact gtcctttcct    2880
aataaaatga ggaaattgca tcgcattgtc tgagtaggtg tcattctatt ctggggggtg    2940
gggtggggca ggacagcaag ggggaggatt gggaagacaa tagcaggcat gctgggatg    3000 cggtgggctc tatggcttct gaggcggaaa gaaccagctg gggctctagg gggtatcccc    3060
acgcgccctg tagcggcgca ttaagcgcgg cgggtgtggt ggttacgcgc agcgtgaccg    3120
ctacacttgc cagcgcccta gcgcccgctc ctttcgcttt cttcccttcc tttctcgcca    3180
cgttcgccgg ctttccccgt caagctctaa atcgggggct cccctttaggg ttccgattta    3240 gtgctttacg gcacctcgac cccaaaaaac ttgattaggg tgatggttca cgtagtgggc    3300
catcgccctg atagacggtt tttcgccctt tgacgttgga gtccacgttc tttaatagtg    3360
gactcttgtt ccaaactgga acaacactca accctatctc ggtctattct tttgatttat    3420
aagggatttt gccgatttcg gcctattggt taaaaatga gctgatttaa caaaaattta    3480
acgcgaatta attctgtgga atgtgtgtca gttagggtgt ggaaagtccc caggctcccc    3540
agcaggcaga agtatgcaaa gcatgcatct caattagtca gcaaccaggt gtggaaagtc    3600
cccaggctcc ccagcaggca gaagtatgca aagcatgcat tcaattagt cagcaaccat    3660 agtcccgccc ctaactccgc ccatcccgcc cctaactccg cccagttccg cccattctcc    3720
gccccatggc tgactaattt tttttattta tgcagaggcc gaggccgcct ctgcctctga    3780
gctattccag aagtagtgag gaggcttttt tggaggccta ggcttttgca aaaagctccc    3840
gggagcttgt atatccattt tcggatctga tcagcacgtg ttgacaatta atcatcggca    3900
tagtatatcg gcatagtata atacgacaag gtgaggaact aaaccatggc caagcctttg    3960
tctcaagaag aatccaccct cattgaaaga gcaacggcta caatcaacag catccccatc    4020
```

```
tctgaagact acagcgtcgc cagcgcagct ctctctagcg acggccgcat cttcactggt   4080
gtcaatgtat atcattttac tgggggacct tgtgcagaac tcgtggtgct gggcactgct   4140
gctgctgcgg cagctggcaa cctgacttgt atcgtcgcga tcggaaatga aacaggggc    4200 atcttgagcc cctgcggacg gtgccgacag gtgcttctcg atctgcatcc tgggatcaaa   4260
gccatagtga aggacagtga tggacagccg acggcagttg ggattcgtga attgctgccc   4320
tctggttatg tgtgggaggg ctaagcactt cgtggccgag gagcaggact gacacgtgct   4380
acgagatttc gattccaccg ccgccttcta tgaaaggttg ggcttcggaa tcgttttccg   4440
ggacgccggc tggatgatcc tccagcgcgg ggatctcatg ctggagttct tcgcccaccc   4500
caacttgttt attgcagctt ataatggtta caaataaagc aatagcatca caaatttcac   4560
aaataaagca tttttttcac tgcattctag ttgtggtttg tccaaactca tcaatgtatc   4620
ttatcatgtc tgtataccgt cgacctctag ctagagcttg gcgtaatcat ggtcatagct   4680
gtttcctgtg tgaaattgtt atccgctcac aattccacac aacatacgag ccggaagcat   4740
aaagtgtaaa gcctggggtg cctaatgagt gagctaactc acattaattg cgttgcgctc   4800
actgcccgct ttccagtcgg gaaacctgtc gtgccagctg cattaatgaa tcggccaacg   4860
cgcggggaga ggcggtttgc gtattgggcg ctcttccgct tcctcgctca ctgactcgct   4920
gcgctcggtc gttcggctgc ggcgagcggt atcagctcac tcaaaggcgg taatacggtt   4980
atccacagaa tcaggggata acgcaggaaa gaacatgtga gcaaaaggcc agcaaaaggc   5040
caggaaccgt aaaaaggccg cgttgctggc gtttttccat aggctccgcc cccctgacga   5100
gcatcacaaa aatcgacgct caagtcagag gtggcgaaac ccgacaggac tataaagata   5160
ccaggcgttt ccccctggaa gctccctcgt gcgctctcct gttccgaccc tgccgcttac   5220
cggatacctg tccgcctttc tcccttcggg aagcgtggcg ctttctcata gctcacgctg   5280
taggtatctc agttcggtgt aggtcgttcg ctccaagctg ggctgtgtgc acgaaccccc   5340
cgttcagccc gaccgctgcg ccttatccgg taactatcgt cttgagtcca acccggtaag   5400
acacgactta tcgccactgg cagcagccac tggtaacagg attagcagag cgaggtatgt   5460
aggcggtgct acagagttct tgaagtggtg gcctaactac ggctacacta agaacagt    5520 atttggtatc tgcgctctgc tgaagccagt taccttcgga aaaagagttg gtagctcttg   5580
atccggcaaa caaccaccg ctggtagcgg tggtttttt gtttgcaagc agcagattac    5640
gcgcagaaaa aaaggatctc aagaagatcc tttgatcttt tctacggggt ctgacgctca   5700
gtggaacgaa aactcacgtt aagggatttt ggtcatgaga ttatcaaaaa ggatcttcac   5760
ctagatcctt ttaaattaaa aatgaagttt taaatcaatc taagtatat atgagtaaac    5820 ttggtctgac agttaccaat gcttaatcag tgaggcacct atctcagcga tctgtctatt   5880
tcgttcatcc atagttgcct gactccccgt cgtgtagata actacgatac gggagggctt   5940
accatctggc cccagtgctg caatgatacc gcgagaccca cgctcaccgg ctccagattt   6000
atcagcaata aaccagccag ccggaagggc cgagcgcaga agtggtcctg caactttatc   6060
cgcctccatc cagtctatta attgttgccg ggaagctaga gtaagtagtt cgccagttaa   6120 tagtttcgc aacgttgttg ccattgctac aggcatcgtg gtgtcacgct cgtcgtttgg    6180
tatggcttca ttcagctccg gttcccaacg atcaaggcga gttacatgat cccccatgtt   6240
gtgcaaaaaa gcggttagct ccttcggtcc tccgatcgtt gtcagaagta agttggccgc   6300
agtgttatca ctcatggtta tggcagcact gcataattct cttactgtca tgccatccgt   6360
```

```
aagatgctttt tctgtgactg gtgagtactc aaccaagtca ttctgagaat agtgtatgcg    6420
gcgaccgagt tgctcttgcc cggcgtcaat acgggataat accgcgccac atagcagaac    6480
tttaaaagtg ctcatcattg gaaaacgttc ttcggggcga aaactctcaa ggatcttacc    6540
gctgttgaga tccagttcga tgtaacccac tcgtgcaccc aactgatctt cagcatcttt    6600
tactttcacc agcgtttctg ggtgagcaaa aacaggaagg caaaatgccg caaaaaaggg    6660
aataagggcg acacggaaat gttgaatact catactcttc cttttttcaat attattgaag    6720 catttatcag ggttattgtc tcatgagcgg atacatattt gaatgtattt agaaaaataa    6780
acaaataggg gttccgcgca catttccccg aaaagtgcca cctgacgtc              6829

<210> SEQ ID NO 12
<211> LENGTH: 10174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
ctcgagccac catgtcccag caaactgcct attcccagca gcgcttccct ccaccgcagg     960
agctatctca agattcattt gggtctcagg catcctcagc cccctcaatg acctccagta    1020
agggagggca agaagatatg aacctgagcc ttcagtcaag accctccagc ttgcctgatc    1080
tatctggttc aatagatgac ctccccatgg ggacagaagg agctctgagt cctggagtga    1140
gcacatcagg gatttccagc agccaaggag agcagagtaa tccagctcag tctccttttct    1200 ctcctcatac ctcccctcac ctgcctggca tccgaggccc ttccccgtcc cctgttggct    1260
ctcccgccag tgttgctcag tctcgctcag gaccactctc gcctgctgca gtgccaggca    1320
accagatgcc acctcggcca cccagtggcc agtcggacac atcatgcat ccttccatga    1380 accaatcaag cattgcccaa gatcgaggtt atatgcagag gaaccccag atgcccagt     1440 acagttcccc ccagccggc tcagcctttat ctccgcgtca gccttccgga ggacagatac    1500
acacaggcat gggctcctac cagcagaact ccatggggag ctatggtccc cagggggtc    1560
```

```
agtatggccc acaaggtggc tacccccaggc agccaaacta taatgccttg cccaatgcca    1620
actaccccag tgcaggcatg gctggaggca taaaccccat gggtgccgga ggtcaaatgc    1680
atggacagcc tggcatccca ccttatggca cactccctcc agggaggatg agtcacgcct    1740
ccatgggcaa ccggccttat ggccctaaca tggccaatat gccacctcag gttgggtcag    1800
ggatgtgtcc cccaccaggg ggcatgaacc ggaaaaccca agaaactgct gtcgccatgc    1860
atgttgctgc caactctatc caaaacaggc cgccaggcta ccccaatatg aatcaagggg    1920
gcatgatggg aactggacct ccttatggac aagggattaa tagtatggct ggcatgatca    1980
accctcaggg accccatat tccatgggtg gaaccatggc caacaattct gcagggatgg    2040
cagccagccc agagatgatg ggccttgggg atgtaaagtt aactccagcc accaaaatga    2100
acaacaaggc agatgggaca cccaagacag aatccaaatc caagaaatcc agttcttcta    2160
ctacaaccaa tgagaagatc accaagttgt atgagctggg tggtgagcct gagaggaaga    2220
tgtgggtgga ccgttatctg gccttcactg aggagaaggc catgggcatg acaaatctgc    2280
ctgctgtggg taggaaacct ctggacctct atcgcctcta tgtgtctgtg aaggagattg    2340
gtggattgac tcaggtcaac aagaacaaaa aatggcggga acttgcaacc aacctcaatg    2400
tgggcacatc aagcagtgct gccagctcct tgaaaaagca gtatatccag tgtctctatg    2460
cctttgaatg caagattgaa cggggagaag accctccccc agacatcttt gcagctgctg    2520
attccaagaa gtcccagccc aagatccagc ctccctctcc tgcgggatca ggatctatgc    2580
aggggcccca gactcccccag tcaaccagca gttccatggc agaaggagga gacttaaagc    2640
caccaactcc agcatccaca ccacacagtc agatcccccc attgccaggc atgagcagga    2700
gcaattcagt tgggatccag gatgccttta atgatggaag tgactccaca ttccagaagc    2760
ggaattccat gactccaaac cctgggtatc agcccagtat gaatacctct gacatgatgg    2820
ggcgcatgtc ctatgagcca aataaggatc cttatggcag catgaggaaa gctccaggga    2880
gtgatccctt catgtcctca gggcagggcc caacggcgg gatgggtgac ccctacagtc    2940
gtgctgccgg ccctgggcta ggaaatgtgg cgatgggacc acgacagcac tatccctatg    3000 gaggtccctta tgacagagtg aggacggagc ctggaatagg gcctgaggga aacatgagca    3060
ctggggcccc acagccgaat ctcatgcctt ccaacccaga ctcggggatg tattctccta    3120
gccgctaccc ccgcagcag cagcagcagc agcagcaacg acatgattcc tatggcaatc    3180
agttctccac ccaaggcacc ccttctggca gccccttccc cagccagcag actacaatgt    3240
atcaacagca acagcagaat tacaagcggc caatggatgg cacatatggc cctcctgcca    3300
agcggcacga aggggagatg tacagcgtgc catacagcac tgggcagggg cagcctcagc    3360
agcagcagtt gccccagcc cagccccagc ctgccagcca gcaacaagct gcccagcctt    3420 ccctcagca agatgtatac aaccagtatg gcaatgccta tcctgccact gccacagctg    3480
ctactgagcg ccgaccagca ggcggccccc agaaccaatt ccattccag tttggccgag    3540 accgtgtctc tgcacccct ggcaccaatg cccagcaaaa catgccacca caaatgatgg    3600
gcggccccat acaggcatca gctgaggttg ctcagcaagg caccatgtgg cagggggcgta    3660 atgacatgac ctataattat gccaacaggc agagcacggg ctctgccccc cagggccccg    3720
cctatcatgg cgtgaaccga acagatgaaa tgctgcacac agatcagagg gccaaccacg    3780
aaggctcgtg gccttcccat ggcacacgcc agccccata tggtccctct gcccctgtgc    3840
cccccatgac aaggcccccct ccatctaact accagccccc accaagcatg cagaatcaca    3900
ttcctcaggt atccagccct gctcccctgc cccggccaat ggagaaccgc acctctccta    3960
```

```
gcaagtctcc attcctgcac tctgggatga aaatgcagaa ggcaggtccc ccagtacctg   4020
cctcgcacat agcacctgcc cctgtgcagc cccccatgat tcggcgggat atcaccttcc   4080
cacctggctc tgttgaagcc acacagcctg tgttgaagca gaggaggcgg ctcacaatga   4140
aagacattgg aaccccggag gcatggcggg taatgatgtc cctcaagtct ggtctcctgg   4200
cagagagcac atgggcatta gataccatca acatcctgct gtatgatgac aacagcatca   4260
tgaccttcaa cctcagtcag ctcccagggt tgctagagct ccttgtagaa tatttccgac   4320
gatgcctgat tgagatcttt ggcatttta a aggagtatga ggtgggtgac ccaggacaga   4380
gaacgctact ggatcctggg aggttcagca aggtgtctag tccagctccc atggaggggtg   4440 gggaagaaga agaagaactt ctaggtccta aactagaaga ggaagaagaa gaggaagtag   4500
ttgaaaatga tgaggagata gccttttcag gcaaggacaa gccagcttca gagaatagtg   4560
aggagaagct gatcagtaag tttgacaagc ttccagtaaa gatcgtacag aagaatgatc   4620
catttgtggt ggactgctca gataagcttg ggcgtgtgca ggagtttgac agtggcctgc   4680
tgcactggcg gattggtggg ggggacacca ctgagcatat ccagacccac ttcgagagca   4740
agacagagct gctgccttcc cggcctcacg caccctgccc accagcccct cggaagcatg   4800
tgacaacagc agagggtaca ccagggacaa cagaccagga ggggcccca cctgatggac    4860 ctccagaaaa acggatcaca gccactatgg atgacatgtt gtctactcgg tctagcacct   4920
tgaccgagga tggagctaag agttcagagg ccatcaagga gagcagcaag tttccatttg   4980
gcattagccc agcacagagc caccggaaca tcaagatcct agaggacgaa ccccacagta   5040
aggatgagac cccactgtgt acccttctgg actggcagga ttctcttgcc aagcgctgcg   5100
tctgtgtgtc caataccatt cgaagcctgt catttgtgcc aggcaatgac tttgagatgt   5160
ccaaacaccc agggctgctg ctcatcctgg gcaagctgat cctgctgcac acaagcacc    5220 cagaacggaa gcaggcacca ctaacttatg aaaaggagga ggaacaggac caaggggtga   5280
gctgcaacaa agtggagtgg tggtgggact gcttggagat gctccgggaa acaccttgg    5340 ttacactcgc caacatctcg gggcagttgg acctatctcc ataccccgag agcatttgcc   5400
tgcctgtcct ggacggactc ctacactggg cagtttgccc ttcagctgaa gcccaggacc   5460 cctttt ccac cctgggcccc aatgccgtcc tttccccgca gagactggtc ttggaaaccc   5520
tcagcaaact cagcatccag gacaacaatg tggacctgat tctggccaca cccccttca    5580 gccgcctgga gaagttgtat agcactatgg tgcgcttcct cagtgaccga agaacccgg    5640 tgtgccggga gatggctgtg gtactgctgg ccaacctggc tcaggggac agcctggcag    5700 ctcgtgccat tgcagtgcag aagggcagta tcggcaacct cctgggcttc ctagaggaca   5760
gccttgccgc cacacagttc cagcagagcc aggccagcct cctccacatg cagaacccac   5820
cctttgagcc aactagtgtg gacatgatgc ggcgggctgc ccgcgcgctg cttgccttgg   5880
ccaaggtgga cgagaaccac tcagagttta ctctgtacga atcacggctg ttggacatct   5940
cggtatcacc gttgatgaac tcattggttt cacaagtcat ttgtgatgta ctgtttttga   6000
ttggccagtc ctcgagtcta gagggcccgc ggttcgaagg taagcctatc cctaaccctc   6060
tcctcggtct cgattctacg cgtaccggtc atcatcacca tcaccattga gtttaaaccc   6120
gctgatcagc ctcgactgtg ccttctagtt gccagccatc tgttgtttgc cctcccccg    6180 tgccttcctt gaccctggaa ggtgccactc ccactgtcct ttcctaataa aatgaggaaa   6240
ttgcatcgca ttgtctgagt aggtgtcatt ctattctggg gggtggggtg gggcaggaca   6300
```

```
gcaaggggga ggattgggaa gacaatagca ggcatgctgg ggatgcggtg ggctctatgg    6360
cttctgaggc ggaaagaacc agctggggct ctagggggta tccccacgcg ccctgtagcg    6420
gcgcattaag cgcggcgggt gtggtggtta cgcgcagcgt gaccgctaca cttgccagcg    6480
ccctagcgcc cgctcctttc gctttcttcc cttcctttct cgccacgttc gccggctttc    6540
cccgtcaagc tctaaatcgg gggctccctt tagggttccg atttagtgct ttacggcacc    6600
tcgaccccaa aaaacttgat tagggtgatg gttcacgtag tgggccatcg ccctgataga    6660 cggttttttcg ccctttgacg ttggagtcca cgttctttaa tagtggactc ttgttccaaa    6720
ctggaacaac actcaaccct atctcggtct attcttttga tttataaggg attttgccga    6780
tttcggccta ttggttaaaa aatgagctga tttaacaaaa atttaacgcg aattaattct    6840
gtggaatgtg tgtcagttag ggtgtggaaa gtccccaggc tccccagcag gcagaagtat    6900
gcaaagcatg catctcaatt agtcagcaac caggtgtgga aagtccccag gctccccagc    6960
aggcagaagt atgcaaagca tgcatctcaa ttagtcagca accatagtcc cgcccctaac    7020
tccgcccatc ccgcccctaa ctccgcccag ttccgcccat tctccgcccc atggctgact    7080 aattttttt atttatgcag aggccgaggc cgcctctgcc tctgagctat tccagaagta    7140
gtgaggaggc ttttttggag gcctaggctt ttgcaaaaag ctcccgggag cttgtatatc    7200
cattttcgga tctgatcagc acgtgttgac aattaatcat cggcatagta tatcggcata    7260
gtataatacg acaaggtgag gaactaaacc atggccaagc ctttgtctca agaagaatcc    7320
accctcattg aaagagcaac ggctacaatc aacagcatcc ccatctctga agactacagc    7380
gtcgccagcg cagctctctc tagcgacggc cgcatcttca ctggtgtcaa tgtatatcat    7440
tttactgggg gaccttgtgc agaactcgtg gtgctgggca ctgctgctgc tgcggcagct    7500
ggcaacctga cttgtatcgt cgcgatcgga aatgagaaca gggcatcttt gagcccctgc    7560
ggacggtgcc gacaggtgct tctcgatctg catcctggga tcaaagccat agtgaaggac    7620
agtgatggac agccgacggc agttgggatt cgtgaattgc tgccctctgg ttatgtgtgg    7680
gagggctaag cacttcgtgg ccgaggagca ggactgacac gtgctacgag atttcgattc    7740
caccgccgcc ttctatgaaa ggttgggctt cggaatcgtt ttccgggacg ccggctggat    7800
gatcctccag cgcggggatc tcatgctgga gttcttcgcc cacccccaact tgtttattgc    7860 agcttataat ggttacaaat aaagcaatag catcacaaat ttcacaaata aagcattttt    7920
ttcactgcat tctagttgtg gtttgtccaa actcatcaat gtatcttatc atgtctgtat    7980
accgtcgacc tctagctaga gcttggcgta atcatggtca gctgtttc ctgtgtgaaa    8040 ttgttatccg ctcacaattc cacacaacat acgagccgga agcataaagt gtaaagcctg    8100
gggtgcctaa tgagtgagct aactcacatt aattgcgttg cgctcactgc ccgctttcca    8160
gtcgggaaac ctgtcgtgcc agctgcatta atgaatcggc caacgcgcgg ggagaggcgg    8220
tttgcgtatt gggcgctctt ccgcttcctc gctcactgac tcgctgcgct cggtcgttcg    8280
gctgcggcga gcggtatcag ctcactcaaa ggcggtaata cggttatcca cagaatcagg    8340
ggataacgca ggaaagaaca tgtgagcaaa aggccagcaa aaggccagga accgtaaaaa    8400
ggccgcgttg ctggcgtttt tccataggct ccgcccccct gacgagcatc acaaaaatcg    8460
acgctcaagt cagaggtggc gaaacccgac aggactataa agataccagg cgtttccccc    8520
tggaagctcc ctcgtgcgct ctcctgttcc gaccctgccg cttaccggat acctgtccgc    8580
ctttctccct tcgggaagcg tggcgctttc tcatagctca cgctgtaggt atctcagttc    8640
ggtgtaggtc gttcgctcca agctgggctg tgtgcacgaa ccccccgttc agcccgaccg    8700
```

```
ctgcgcctta tccggtaact atcgtcttga gtccaacccg gtaagacacg acttatcgcc   8760
actggcagca gccactggta acaggattag cagagcgagg tatgtaggcg gtgctacaga   8820
gttcttgaag tggtggccta actacggcta cactagaaga acagtatttg gtatctgcgc   8880
tctgctgaag ccagttacct tcggaaaaag agttggtagc tcttgatccg gcaaacaaac   8940
caccgctggt agcggtggtt ttttgtttg caagcagcag attacgcgca gaaaaaagg    9000
atctcaagaa gatcctttga tcttttctac ggggtctgac gctcagtgga acgaaaactc   9060
acgttaaggg attttggtca tgagattatc aaaaaggatc ttcacctaga tccttttaaa   9120
ttaaaaatga agttttaaat caatctaaag tatatatgag taaacttggt ctgacagtta   9180
ccaatgctta atcagtgagg cacctatctc agcgatctgt ctatttcgtt catccatagt   9240
tgcctgactc cccgtcgtgt agataactac gatacgggag ggcttaccat ctggccccag   9300
tgctgcaatg ataccgcgag acccacgctc accggctcca gatttatcag caataaacca   9360
gccagccgga agggccgagc gcagaagtgg tcctgcaact ttatccgcct ccatccagtc   9420
tattaattgt tgccgggaag ctagagtaag tagttcgcca gttaatagtt tgcgcaacgt   9480
tgttgccatt gctacaggca tcgtggtgtc acgctcgtcg tttggtatgg cttcattcag   9540
ctccggttcc caacgatcaa ggcgagttac atgatccccc atgttgtgca aaaaagcggt   9600
tagctccttc ggtcctccga tcgttgtcag aagtaagttg gccgcagtgt tatcactcat   9660
ggttatggca gcactgcata attctcttac tgtcatgcca tccgtaagat gcttttctgt   9720
gactggtgag tactcaacca agtcattctg agaatagtgt atgcggcgac cgagttgctc   9780
ttgcccggcg tcaatacggg ataataccgc gccacatagc agaactttaa aagtgctcat   9840
cattggaaaa cgttcttcgg ggcgaaaact ctcaaggatc ttaccgctgt tgagatccag   9900
ttcgatgtaa cccactcgtg cacccaactg atcttcagca tcttttactt tcaccagcgt   9960
ttctgggtga gcaaaaacag gaaggcaaaa tgccgcaaaa aagggaataa gggcgacacg  10020
gaaatgttga atactcatac tcttcctttt tcaatattat tgaagcattt atcagggtta  10080
ttgtctcatg agcggataca tatttgaatg tatttagaaa aataaacaaa tagggttcc   10140
gcgcacattt ccccgaaaag tgccacctga cgtc                              10174
```

<210> SEQ ID NO 13
<211> LENGTH: 13
<212> TYPE: PRT
<213> ORGANISM: Unknown
<220> FEATURE:
<223> OTHER INFORMATION: Description of Unknown:
      CAD peptide 1

<400> SEQUENCE: 13

Leu Leu Asp Thr Ile Gly Ile Ser Gln Pro Gln Trp Arg
1               5                   10

<210> SEQ ID NO 14
<211> LENGTH: 26
<212> TYPE: PRT
<213> ORGANISM: Unknown
<220> FEATURE:
<223> OTHER INFORMATION: Description of Unknown:
      CAD peptide 2

<400> SEQUENCE: 14

Met Ala Glu Ile Gly Glu His Val Ala Pro Ser Glu Ala Ala Asn Ser
1               5                   10                  15

```
Leu Glu Gln Ala Gln Ala Ala Ala Glu Arg
            20                  25

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5
```

TARGETING OF ARID1A-DEFICIENT CANCERS BY INHIBITING DE NOVO PYRIMIDINE SYNTHESIS PATHWAY

CROSS-REFERENCE TO RELATED APPLICATIONS

This application is a U.S. application which claims priority to U.S. Provisional Application No. 62/941,037, filed on Nov. 27, 2019, which is herein incorporated by reference in its entirety.

STATEMENT REGARDING FEDERALLY SPONSORED RESEARCH

This invention was made with government support under CA013330 awarded by National Institutes of Health and under W81XWH-16-1-0196 awarded by United States Army Medical Research and Material Command. The government has certain rights in the invention.

SEQUENCE LISTING

The instant application contains a Sequence Listing which has been submitted electronically in ASCII format and is hereby incorporated by reference in its entirety. Said ASCII copy, created on Oct. 30, 2020, is named 251609_000036_SL.txt and is 67,530 bytes in size.

FIELD OF THE INVENTION

The invention relates to methods, kits, and compositions for treating aberrantly proliferating cells harboring an ARID1A mutation.

BACKGROUND

ARID1A (also known as BAF250A) is a commonly mutated tumor suppressor in human cancer. ARID1A is a core subunit of the BAF (mammalian SWI/SNF) chromatin remodeling complex which modulates gene expression by binding to AT-rich DNA regions, mobilizing nucleosomes, and interacting with transcription factors, coactivators, and corepressors[1]. Among BAF subunits, ARID1A is the most commonly mutated in human cancer, and these mutations occur in a tissue-specific manner, with highest mutational frequency occurring in gynecologic cancers including clear cell ovarian cancer (46-57%), endometrioid ovarian cancer (30%), endometrial cancer (34%) and uterine carcinosarcoma (20-36%)[2-4].

There exists an ongoing need for improved methods, kits, and compositions for treatment of ARID1A-based cancers.

SUMMARY OF THE INVENTION

In one aspect, provided herein is a method for treating an ARID1A-mutant tumor or cancer in a subject in need thereof. The method includes (i) administering to the subject an effective amount of a pyrimidine synthesis inhibitor. The method further includes (ii) administering to the subject an effective amount of a DNA repair inhibitor.

In various embodiments of the above method, the pyrimidine synthesis inhibitor and DNA repair inhibitors are individually a small molecule, protein, fusion protein, peptide, nucleic acid, aptamer, avimer, or derivatives or fragments thereof.

In some embodiments of the above method, the pyrimidine synthesis inhibitor is an inhibitor of dihydroorotate dehydrogenase (DHODH), an inhibitor of orotate phosphoribosyl transferase, an inhibitor of orotidylate decarboxylase, a direct inhibitor of CAD, a S6 kinase beta-1 (S6K1) inhibitor, an mTORC1 inhibitor, an inhibitor of mammalian target of rapamycin complex 1 (mTORC1) signaling, or a combination thereof. In various embodiments, the pyrimidine synthesis inhibitor is a DHODH inhibitor. In some embodiments, the DHODH inhibitor is teriflunomide, leflunomide, or a combination thereof. In various embodiments, the DHODH inhibitor is teriflunomide. In some embodiments, teriflunomide is administered at a dose from about 2.5 mg to about 25 mg. In various embodiments, the leflunomide is administered at a dose from about 4 mg to about 40 mg. In some embodiments, the pyrimidine synthesis inhibitor is a S6K1 inhibitor. In various embodiments, the S6K1 inhibitor is PF-4708671. In some embodiments, PF-4708671 is administered at a dose from about 0.5 mg to about 50 mg.

In various embodiments of the above method, the DNA repair inhibitor is an ataxia telangiectasia and Rad3-related (ATR) inhibitor, a checkpoint kinase 1 (CHK1) inhibitor, or a poly ADP ribose polymerase (Parp) inhibitor. In some embodiments, the ATR inhibitor is AZD6738, VX-970, or a combination thereof. In various embodiments, the ATR inhibitor is VX-970. In some embodiments, VX-970 is administered at a dose of from about 1 mg to about 100 mg. In various embodiments, the ATR inhibitor is AZD6738. In some embodiments, AZD6738 is administered at a dose from about 20 mg to about 240 mg.

In various embodiments of the above method, the tumor or cancer cells are in a brain, breast, bladder, bone, cartilage, cervix, colon, cornea, eye, neural tissue, glia, esophagus, fallopian tube, heart, pancreas, intestines, gallbladder, kidney, liver, lung, ovary, pancreas, parathyroid, pineal gland, pituitary gland, prostate, spinal cord, spleen, skeletal muscle, skin, muscle, stomach, testis, thymus, thyroid, trachea, urogenital tract, ureter, urethra, uterus, endometrium, vagina, or combination thereof. In various embodiments, the ARID1A-mutant tumor or cancer is a gynecologic cancer. In some embodiments, the ARID1A-mutant tumor or cancer cell is in the ovary, uterus, endometrium, vagina, stomach, gallbladder, or bladder. In various embodiments, the ARID1A-mutant cancer is clear cell ovarian cancer, endometrioid ovarian cancer, endometrial cancer, or uterine carcinosarcoma. In various embodiments, the cancer is not a PTEN-mutant cancer.

In various embodiments, the above method further includes determining the presence of an ARID1A mutation in cells of the subject prior to administering the pyrimidine synthesis inhibitor and DNA repair inhibitor.

In various embodiments of the above method, steps (i) and (ii) occur simultaneously.

In another aspect, provided herein is a kit including a) a composition comprising a pyrimidine synthesis inhibitor, b) a composition comprising a DNA repair inhibitor, and c) optionally instructions for use. In various embodiments, the composition of a) comprises about 2.5 mg to about 1 g of the pyrimidine synthesis inhibitor. In some embodiments, the composition of b) comprises about 1 mg to about 1 g of the DNA repair inhibitor.

In various embodiments of the above kit, the pyrimidine synthesis inhibitor and DNA repair inhibitors are individually a small molecule, protein, fusion protein, peptide, nucleic acid, aptamer, avimer, or derivatives or fragments thereof.

In some embodiments of the above kit, the pyrimidine synthesis inhibitor is an inhibitor of DHODH, an inhibitor of orotate phosphoribosyl transferase, an inhibitor of orotidylate decarboxylase, a direct inhibitor of CAD, a S6K1 inhibitor, an mTORC1 inhibitor, an inhibitor of mTORC1 signaling, or a combination thereof. In various embodiments, the pyrimidine synthesis inhibitor is a DHODH inhibitor. In some embodiments, the DHODH inhibitor is teriflunomide, leflunomide, or a combination thereof. In various embodiments, the DHODH inhibitor is teriflunomide. In some embodiments, the pyrimidine synthesis inhibitor is a S6K1 inhibitor. In various embodiments, the S6K1 inhibitor is PF-4708671.

In various embodiments of the above kit, the DNA repair inhibitor is an ATR inhibitor, a CHK1 inhibitor, or a Parp inhibitor. In some embodiments, the ATR inhibitor is AZD6738, VX-970, or a combination thereof. In various embodiments, the ATR inhibitor is VX-970. In some embodiments, the ATR inhibitor is AZD6738.

In another aspect, provided herein is a method for treating an ARID1A-mutant tumor or cancer in a subject in need thereof comprising administering the compositions of the above kit to treat the subject. In various embodiments of the method, teriflunomide is administered at a dose from about 2.5 mg to about 25 mg. In some embodiments of the method, leflunomide is administered at a dose from about 4 mg to about 40 mg. In various embodiments, AZD6738 is administered at a dose from about 20 mg to about 240 mg. In some embodiments, VX-970 is administered at a dose of about 1 mg to about 100 mg.

In various embodiments of the above method, the tumor or cancer is in a brain, breast, bladder, bone, cartilage, cervix, colon, cornea, eye, neural tissue, glia, esophagus, fallopian tube, heart, pancreas, intestines, gallbladder, kidney, liver, lung, ovary, pancreas, parathyroid, pineal gland, pituitary gland, prostate, spinal cord, spleen, skeletal muscle, skin, muscle, stomach, testis, thymus, thyroid, trachea, urogenital tract, ureter, urethra, uterus, endometrium, vagina, or combination thereof. In some embodiments, the tumor or cancer is in the ovary, uterus, endometrium, vagina, stomach, gallbladder, or bladder. In some embodiments, the ARID1A-mutant tumor or cancer is a gynecologic cancer. In various embodiments, the ARID1A-mutant cancer is clear cell ovarian cancer, endometrioid ovarian cancer, endometrial cancer, or uterine carcinosarcoma. In some embodiments, the cancer is not a PTEN-mutant cancer.

In various embodiments, the above method further includes determining the presence of an ARID1A mutation in cells of the subject prior to administering the composition of a) or b).

In another aspect, provided herein is a method for decreasing proliferation of an aberrantly proliferating cell comprising contacting the aberrantly proliferating cell with the compositions of the above kit. In some embodiments, the aberrantly proliferating cell is in a subject. In various embodiments, the aberrantly proliferating cell is a tumor or cancer cell.

In some embodiments of the above method, the tumor or cancer cell is in a brain, breast, bladder, bone, cartilage, cervix, colon, cornea, eye, neural tissue, glia, esophagus, fallopian tube, heart, pancreas, intestines, gallbladder, kidney, liver, lung, ovary, pancreas, parathyroid, pineal gland, pituitary gland, prostate, spinal cord, spleen, skeletal muscle, skin, muscle, stomach, testis, thymus, thyroid, trachea, urogenital tract, ureter, urethra, uterus, endometrium, vagina, or combination thereof. In various embodiments, the tumor or cancer cell is in the ovary, uterus, endometrium, vagina, stomach, gallbladder, or bladder. In some embodiments, the aberrantly proliferating cell is a gynecologic cancer cell. In some embodiments, the cancer cell is a clear cell ovarian cancer cell, an endometrioid ovarian cancer cell, an endometrial cancer cell, or a uterine carcinosarcoma cell. In some embodiments, the cell is not a PTEN-mutant cancer cell.

In some embodiments, the above method further includes determining whether the cell is likely to include an ARID1A mutation prior to contacting the cell with the compositions.

In various embodiments of the above method, the subject is a mammal. In some embodiments, the mammal is a human.

In some embodiments, the above method includes administering at least one additional cancer therapy.

These and other aspects of the present invention will be apparent to those of ordinary skill in the art in the following description, claims and drawings.

BRIEF DESCRIPTION OF DRAWINGS

This patent application file contains at least one drawing executed in color. Copies of this patent application with color drawing(s) will be provided by the Office upon request and payment of the necessary fee.

FIG. 1A shows Coomassie blue staining. The right lane is staining of the ARID1A complex immunopurified from an ARID1A-wildtype cell line (KLE). The left lane is a stained immunopurified control IgG complex. Arrows designate protein band identification by LC-MS/MS, with black text for ARID1A and SWI/SNF family members and red text for the multifunctional enzyme CAD. FIGS. 1B-1D show an assessment of endogenous protein-protein interactions in an ARID1A-wildtype cell line. Immunoprecipitation with the indicated antibody or control IgG antibody was performed, and immunoprecipitated proteins were detected by immunoblotting. At least two independent experiments were done, and representative immunoblots are shown. FIG. 1B shows shows that both CAD and the core SWI/SNF subunit SMARCA4 co-immunoprecipitated with ARID1A. Immunoprecipitation was done using an anti-ARID1A antibody. FIG. 1C shows that ARID1A, but not SMARCA4, co-immunoprecipitated with CAD. Immunoprecipitation was done using an anti-CAD antibody. FIG. 1D shows that endogenous ARID1A, but not CAD, co-immunoprecipitated with SMARCA4. Immunoprecipitation was done using an anti-SMARCA4 antibody. FIG. 1E shows constructs where recombinant, glutathione S-transferase (GST)-tagged proteins were made to include full-length CAD (SEQ ID NO: 5) or one of four unique non-overlapping CAD fragments (SEQ ID NO: 6-9). Each of the CAD fragments contained a functional enzyme component, as shown. CAD fusion proteins were expressed in bacteria. FIG. 1F shows immunoblots where whole-cell lysates were prepared using HEK293T cells made to express HA-tagged full-length ARID1A (SEQ ID NO: 4) followed by a GST pulldown assay using recombinant GST-CAD fusion proteins and immunoblotting using an anti-HA antibody to detect HA-ARID1A (SEQ ID NO: 4). Recombinant full-length GST-CAD (SEQ ID NO: 5) and the GST-ATCase domain (SEQ ID NO: 9) demonstrated in vitro binding to HA-tagged ARID1A (SEQ ID NO: 4). FIG. 1G shows constructs where recombinant ARID1A-V5 fusion proteins (SEQ ID NO: 10-12) were made for expression of full-length ARID1A (1-2285) (SEQ ID NO: 10), N-terminal ARID1A (1-1758) (SEQ ID NO: 11), or C-terminal ARID1A (1759-2285) (SEQ ID NO: 12) in HEK293T cells. FIG. 1G discloses "6XHis" as SEQ ID NO: 15. FIG. 1H shows immunoblots demonstrating that the GST-ATCase fusion protein (SEQ ID NO: 9) (but not the control GST protein assessed on the left side of the panel (GST-IP)) demonstrated in vitro binding to V5-tagged, full-length ARID1A (1-2285) (SEQ ID NO: 10) and to C-terminal ARID1A (1759-2285) (SEQ ID NO: 12), but not to N-terminal ARID1A (1-1758) (SEQ ID NO: 11). These immunoblots indicate that the protein-protein interaction of ARID1A and CAD is localized to the C-terminal regions of both CAD (ATCase domain, 1823-2225) and ARID1A (1759-2285).

FIG. 2A shows that protein expression levels of total CAD and phosphorylated CAD increased in ARID1A-knockdown cells compared to control cells, as shown by immunoblotting with anti-CAD and anti-phosphorylated-CAD antibodies. Immunoblotting was completed using an anti-ARID1A antibody to demonstrate knockdown of ARID1A protein expression following stable transfection with short hairpin RNAs, shARID1A (a) (SEQ ID NO: 1) and shARID1A (b) (SEQ ID NO: 2), compared with control transfection with a non-targeting short hairpin RNA, shCON (SEQ ID NO: 3). Equal protein loading was shown by immunoblotting with an anti-β-actin antibody and Ponceau staining of the nitrocellulose membrane. At least five independent experiments were done, and representative results are depicted in FIG. 2A. FIG. 2B is an immunoblot showing restoration of ARID1A protein expression in SKOV2 and OVISE cells following stable transfection with Lenti-puro-ARID1A-V5 (ARID1A) and doxycycline (Dox) induction compared with no induction, or compared with control transfection with Lenti-puro-LacZ-V5 (LacZ), with or without Dox induction. Protein expression levels of V5 tag were assessed, confirming Dox-inducible expression in transfected cell lines. At least three independent experiments were done, and representative results are shown in FIG. 2B. FIG. 2C shows immunoblots for evaluating the effect of ARID1A on CAD protein. Immunoblotting using anti-CAD and anti-CAD Ser1859 antibodies was performed. CAD and phosphorylated CAD protein expression decreased in SKOV3 and OVISE with ARID1A-restoration following stable transfection with Lenti-puro-ARID1A (ARID1A) and induction with Dox, compared with no Dox induction, or compared with control transfection with Lenti-puro-LacZ (LacZ), with or without Dox induction. Equal protein loading was demonstrated by immunoblotting with an anti-GAPDH antibody. At least three independent experiments were done, and representative results are shown in FIG. 2C. FIG. 2D shows representative immunofluorescence staining of ES2 cells for phosphorylated CAD Ser1859 (green) and ARID1A (red). P-CAD Ser1859 protein increased in the ARID1A-knockdown cells compared to control cells. Nuclei are indicated in FIG. 2D by DAPI staining. The scale bar in FIG. 2D corresponds to 40 μm. FIG. 2E shows representative immunofluorescence staining of the SKOV3 (left) and OVISE (right) cell lines for phosphorylated CAD Ser1859 (green) and ARID1A (red). P-CAD Ser1859 protein decreased in ARID1A-restoration cells following induction by doxycycline (Dox) for 2 days compared to control cells. Nuclei are indicated in FIG. 2E by DAPI staining. The scale bar in FIG. 2E corresponds to 20 μm.

FIG. 3A is a diagram showing the steps in a de novo pyrimidine synthesis pathway. FIG. 3B is a bar graph showing an effect of ARID1A knockdown on de novo pyrimidine synthesis. Knockdown cells were grown in media including carbon-14-labeled aspartate. After a 6-hour incubation, RNA was isolated from the cells, and carbon-14 incorporation into the RNA was quantified as counts per minute (cpm) measured by a scintillation counter and was normalized to amount of RNA (micrograms). The bar graph shows increased carbon-14 incorporation into RNA in ARID1A-knockdown cells (shARID1A) relative to control cells (shCon). Mean±SD calculated from two independent experiments is shown in the bar graph. "**" indicates a $P<0.0001$ according to a two-tailed t-test. FIG. 3C is a bar graph showing cellular UTP levels in ARID1A-knockdown cells, shARID1A (a) and shARID1A (b). UTP increased in ARID1A-knockdown cells relative to control cells, shCon. Mean±SD calculated from two independent experiments is shown. "*" indicates $P<0.001$ as calculated by One-way ANOVA with Tukey's post-test. FIG. 3D is a bar graph showing cellular UTP levels in ARID1A-restoration cell lines (SKOV3, left, and OVISE, right) following stable transfection with Lenti-puro-ARID1A (ARID1A) and induction with doxycycline (Dox) compared to no Dox induction, or compared to control transfection with Lenti-puro-LaxZ (LacZ), with or without Dox. Mean±SD calculated from two independent experiments is shown. "" indicates $P<0.01$, and "*" $P<0.001$, where P is calculated using One-way ANOVA with Tukey's post-test.

FIG. 4A shows in an upper panel a plot quantifying the effect of teriflunomide on cells. The Y-axis represents the relative cell number following drug treatment for 72 hours at concentrates represented by the X-axis. ES2 ARID1A-knockdown cells, depicted by a blue line for shARID1A (a) and a green line for shARID1A (b), were more sensitive to teriflunomide, resulting in a decreased cell number following drug treatment, compared to untransfected cells (black line) or shCon cells (gray line). The lower panel of FIG. 4A is a bar graph summarizing data depicted in the upper panel of FIG. 4A. The bar graph shows the teriflunomide concentration that resulted in a 50% growth inhibitory effect ($IC_{50}$. The bars depict mean $IC_{50}$±SD for five independent experiments. "**" indicates a $P<0.0001$, where P has been calculated by One-way ANOVA with Tukey's post-test. FIG. 4B shows in an upper panel a plot quantifying the effect of teriflunomide in SKOV3 cells that were stably transfected with Lenti-puro-ARID1A-V5 (ARID1A) or Lenti-puro-LacZ-V5 (LacZ). ARID1A-restoration cells induced by doxycycline (ARID1A-Dox) (green line) were more resistant to teriflunomide, resulting in an increased cell number following drug treatment, compared to uninduced cells (blue line). The lower panel of FIG. 4B is a bar graph summarizing data depicted in the upper panel of FIG. 4B. The bar graph shows the teriflunomide concentration that resulted in a 50% growth inhibitory effect ($IC_{50}$). The bars depict mean $IC_{50}$±SD for five independent experiments. "*" indicates a $P<0.001$, where P has been calculated by One-way ANOVA with Tukey's post-test. FIG. 4C shows in an upper panel a plot quantifying the effect of teriflunomide in OVISE cells that were stably transfected with Lenti-puro-ARID1A-V5 (ARID1A) compared with control cells transfected with control cells transfected with non-targeting Lenti-puro-LacZ-V5 (LacZ). ARID1A-restoration cells induced by Dox (green line) were more resistant to teriflunomide, resulting in an increased cell number following drug treatment, compared to uninduced cells (blue line). The lower panel of FIG. 4C is a bar graph summarizing data depicted in the upper panel of FIG. 4C. The bar graph shows the teriflunomide concentration that resulted in a 50% growth inhibitory effect (IC$_{50}$). The bars depict mean IC$_{50}$±SD for five independent experiments. "***" indicates a P<0.001, where P has been calculated by One-way ANOVA with Tukey's post-test. FIG. 4D is a plot showing the effect of teriflunomide on xenograft-bearing mice administered 4 mg/kg teriflunomide every other day (black arrows). The effect of teriflunomide on tumor xenograft growth is shown by depiction of the mean tumor volume±SD (N=6 to 8 animals/group) for each of the following groups: shCon treated with vehicle (black line), shARID1A treated with vehicle (blue line), shCon treated with teriflunomide (gray line), and shARID1A treated with teriflunomide (green line). Teriflunomide effectively inhibited tumor growth of shARID1A xenografts (green line), but not shCon xenografts (gray line). FIG. 4E is a box plot summarizing data shown in FIG. 4D by graphing terminal tumor volumes. Bars depict median (middle line) and mean (+) tumor volumes for each group. "*" indicates P<0.05, where P has been calculated by One-way ANOVA with Tukey's post-test. FIG. 4F shows images of representative xenograft tumor tissue sections stained with hematoxylin and eosin. Similar characteristics of high-grade carcinoma were observed in all xenograft tumor samples. FIG. 4G shows immunoblots of representative tumor xenograft cell lysates. ARID1A, CAD, and phospho-CAD Ser1859 protein expression was evaluated. ARID1A-knockdown xenografts (shARID1A) showed decreased ARID1A protein levels and increased CAD and phospho-CAD protein levels. Equal protein loading was confirmed by Ponceau staining of nitrocellulose membranes (not shown) and by immunoblotting with an anti-GAPDH antibody. FIG. 4H shows representative immunohistology stains of xenograft tumor tissue sections for ARID1A, CAD, and phosphorylated CAD Ser1859. The negative-control samples underwent the same immunohistology staining procedure but without primary antibody incubation. Upregulation of CAD and P-CAD Ser1859 was observed in the ARID1A-knockdown xenografts (shARID1A) compared to control xenografts (shCon). This was consistent with immunoblotting results. Scale bars shown in FIG. 4H represents 50 µm. FIG. 4I is Kaplan-Meier survival curves quantifying the effect of teriflunomide in an ARID1A-deficient SKOV3 tumor xenograft model. 4 mg/kg teriflunomide was administered to xenograft-bearing mice every other day. Survival was significantly prolonged in the teriflunomide treatment group compared to the vehicle control group. "**" indicates P<0.01, where P has been calculated by a log-rank test.

FIG. 5A is a plot showing the effect of combination treatment of ES2 cells with teriflunomide and AZD6738 for 72 h. ARID1A-knockdown cells, depicted by a blue line for shARID1A (a) and a green line for shARID1A (b), were more sensitive to combination treatment compared to untransfected cells (black line) or shCon cells (gray line). FIG. 5B is a plot showing the effect of combination treatment of ES2 cells with teriflunomide and VX-970 for 72 h. ARID1A-knockdown cells, as depicted by the blue line for shARID1A (a) and the green line for shARID1A (b), were more sensitive to combination treatment compared to untransfected cells (black line) or shCon cells (gray line). FIG. 5C is a plot showing the effect of combination treatment of ARID1A-restoration OVISE cells with teriflunomide and AZD6738 for 72 h. ARID1A-induced cells (ARID1A-Dox), depicted by the green line, were more resistant to combination treatment compared to non-induced cells, or control cells. FIGS. 5D-5F are FA-CI plots (i.e., Chou-Talalay plots), where x=fraction affected (FA) vs. y=combination index (CI). CI<1, =1, and >1 indicate synergism, an additive effect, and antagonism, respectively. FIG. 5D is an FA-CI plot summarizing the data shown in FIG. 5A. FIG. 5E is an FA-CI plot summarizing the data shown in FIG. 5B. FIG. 5F is an FA-CI plot summarizing the data shown in FIG. 5C. FIG. 5G shows immunoblots evaluating γ-H2AX protein expression in ES2 cells lysates prepared at 48 h or 72 h. Teriflunomide (15 µM) and ATRi AZD6738 (1.5 µM) were used in single-drug and combination treatment groups. AZD6738 treatment decreased levels of P-CHK1 Ser345, as expected. ARID1A-knockdown cells (shARID1A) in the single-drug treatment groups showed increased γ-H2AX protein levels, but the highest levels were in a Teri+AZD combination treatment group. Equal protein loading was confirmed by immunoblotting with an anti-GAPDH antibody. FIG. 5H shows immunoblots evaluating Teri+VX combination treatment by detecting γ-H2AX protein expression in ES2 cell lysates prepared at both 24 h and 48 h. Teriflunomide (15 µM) and VX-970 (0.075 µM) were used in single-drug and combination treatment groups. ARID1A-knockdown cells (shARID1A) showed increased γ-H2AX protein levels in the single-drug treatment groups, but the highest levels were in the Teri+VX combination treatment group. Equal protein loading was confirmed by immunoblotting with an anti-GAPDH antibody. FIG. 5I shows representative immunofluorescence stains of ES2 cells for γ-H2AX (green) and DAPI (blue) at 24 h. Teriflunomide (15 µM), AZD6738 (1.5 µM), and VX-970 (0.075 µM) were used in single-drug and combination treatment groups. ARID1A-knockdown cells (shARID1A) showed increased γ-H2AX protein levels in the single-drug treatment groups, but the highest levels were in the Teri+VX combination treatment group. Scale bars shown in FIG. 5I represent 10 µm. FIG. 5J is a plot showing the effect of combination treatment with teriflunomide and AZD6738 of xenograft-bearing mice. The effect on tumor xenograft growth is shown by depiction of the mean tumor volume±SD (N=from 7 animals/group to 9 animals/group) for each of the following groups: shARID1A treated with vehicle (black line), shARID1A treated with teriflunomide (green line), shARID1A treated with AZD6738 (blue line), and shARID1A treated with teriflunomide and AZD6738 (red line). Teriflunomide (4 mg/kg) or vehicle was intraperitoneally injected every other day. AZD6738 (25 mg/kg) or vehicle was given by oral gavage every day. Combination treatment more effectively inhibited tumor growth of shARID1A xenografts (red line) compared to single-drug-treated xenografts (green and blue lines). FIG. 5K shows representative images of ES2-shARID1A xenografts treated with vehicle control, teriflunomide, AZD6738, or teriflunomide plus AZD6738. Images were taken at endpoints of scheduled treatments. Vehicle control reached maximum tumor size on day 21. Tumor size on day 29 showed that combination treatment more effectively inhibited tumor growth of shARID1A xenografts compared to single-drug-treated xenografts.

FIG. 7 includes an image of a Ponceaus s stain showing equal loading of samples.

FIG. 9 includes a left panel that is a cell growth curve showing cell growth (Y-axis) following 72 h of treatment at concentrations of teriflunomide indicated on the X-axis. FIG. 9 includes a right panel that is a bar graph showing the teriflunomide IC50 for HCT116 ARID1A knockout cells compared with control cells. Each bar represents mean±SD of 3 independent experiments. "****" indicates P<0.0001, where P was calculated by two-tailed t-test.

FIG. 10A is a cell growth curve indicating cell growth (Y-axis) following 72 h treatment at concentrations of PF-4708671 indicated on the X-axis. Each bar represents mean±SD of 3 independent experiments. FIG. 10B is a bar graph showing the PF-4708671 IC50 for each cell line. Each bar shows mean±SD of 3 independent experiments. "*" indicates P<0.001, and "" indicates P<0.01, where P was calculated by one-way ANOVA with Tukey's post-test.

FIG. 11A is a plot showing the effect of teriflunomide on tumor xenograft growth. Mean tumor volume is plotted with bars representing±SD (N=10 animals/group) for the following two groups: shCon treated with vehicle (black line) and shCon treated with teriflunomide (green line). Tumor volumes were similar between the treatment and vehicle groups. FIG. 11B is a bar graph summarizing tumor weight on day 17. Bars in FIG. 11B represent ±SD (N=10 animals/group). FIGS. 11C and 11D are plots showing analyses of a correlation of tumor weight with tumor volume. FIG. 11E is an image of tumors on day 17.

FIG. 12 shows light microscopy images of cell morphology following treatment with teriflunomide, AZD6738, or a combination of both drugs for 72 h. The concentrations of teriflunomide and AZD6738 were 15 μM and 1.5 μM AZD6738, respectively; treatment concentrations were derived from respective IC50 values for each drug in ES2 cells.

FIGS. 13A-13D are plots showing correlation analyses of tumor weights with tumor volumes in ES2-shARID1A xenografts treated with vehicle control, teriflunomide, AZD6738, or teriflunomide plus AZD6738. Data are from an endpoint of scheduled treatment (21 or 29 days). The vehicle group reached terminal volume by day 21.

FIG. 9 includes a left panel and a right panel. The left panel is a plot of cell growth (Y-axis) measured following 72 h treatment with concentrations of VX-970 indicated on the X-axis. Each symbol represents mean±SD of three independent experiments. The right panel is a bar graph showing $IC_{50}$ for VX-970 treatment of ARID1A-knockout HCT116 cells compared with control cells. Bars show mean±SD of three independent experiments. "****" indicates P<0.0001, where P is determined by two-tailed t-test.

DETAILED DESCRIPTION

The present invention provides methods and kits for treatment of ARID1A-mutant tumors, cancers, or aberrantly proliferating cells. More particularly, the present invention provides methods and kits for combination treatment of a subject in need thereof or of a cell(s) where the combination treatment includes administering a pyrimidine synthesis inhibitor and administering a DNA repair inhibitor.

Figure 3:
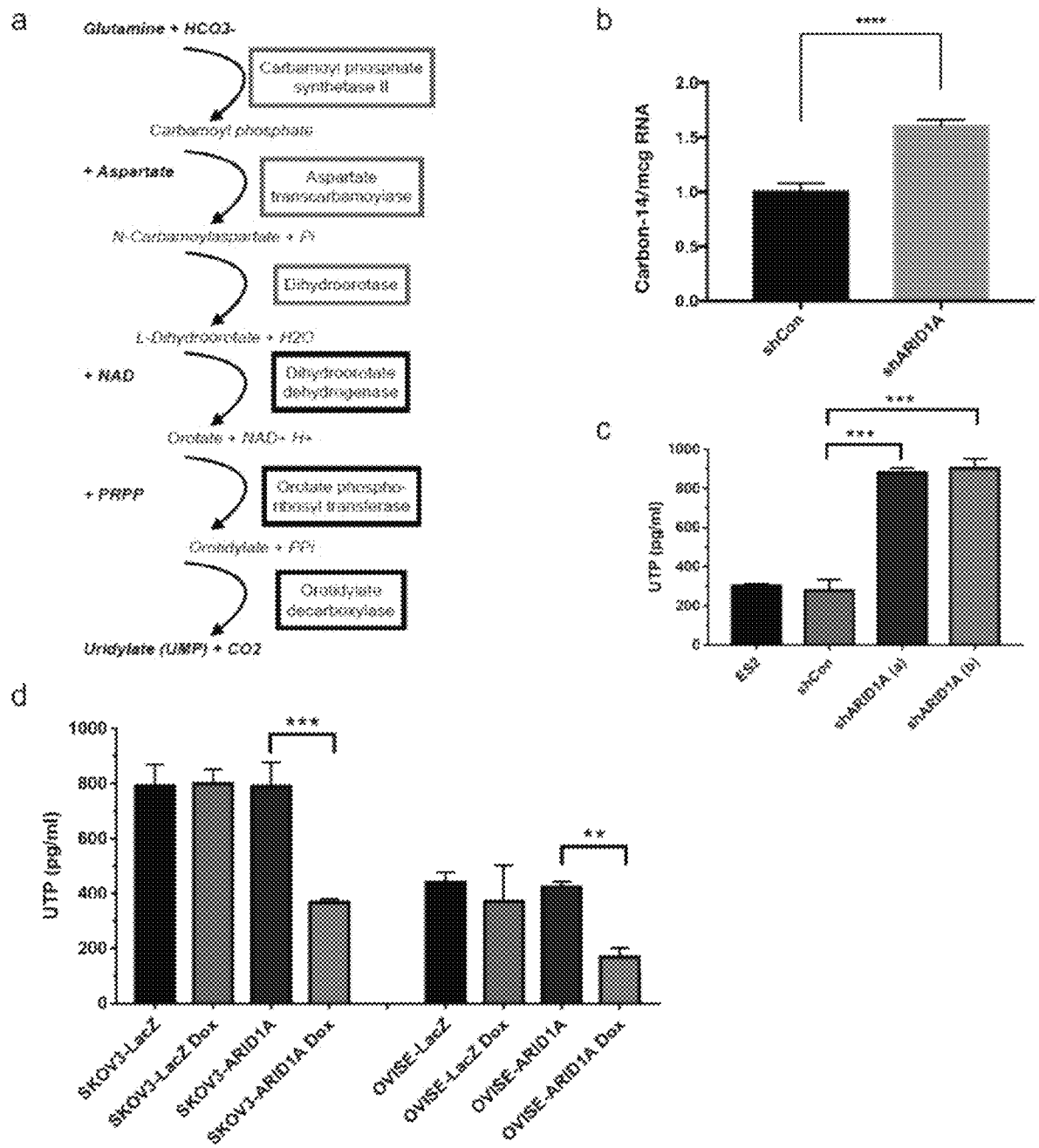
FIGS. 3A-3D show that ARID1A regulates de novo pyrimidine synthesis.

The present invention is based on the surprising discovery demonstrated in the examples that ARID1A, a commonly mutated tumor suppressor in human cancer, interacts with CAD such that an ARID1A deficiency effects an increase in CAD activity and, thereby, effects an increase in pyrimidine synthesis in a cell. As noted in the background section above, there exists an ongoing need for identifying improved methods, kits, and compositions for treatment of ARID1A-based cancers. Therefore, the discovery of an interaction between CAD and ARID1A prompted investigations into effective cancer or tumor treatment methods targeting pyrimidine synthesis because CAD catalyzes three reactions central to pyrimidine synthesis in a cell, as shown in FIG. 3A.

Further investigations led to the surprising discovery demonstrated in the examples that combined administration of pyrimidine synthesis inhibitors (e.g., DHODH inhibitors such as teriflunomide or leflunomide, or S6K1 inhibitors such as PF-4708671) and DNA synthesis inhibitors (e.g., ATR inhibitors such as AZD6738 or VX-970) may result in a synergistic treatment effect. In certain embodiments, DNA synthesis inhibitors potentiate the effects of pyrimidine synthesis inhibitors on tumor or cancer cell proliferation and/or viability.

Definitions

Unless defined otherwise, technical and scientific terms used herein have the same meaning as commonly understood by one of ordinary skill in the art to which this invention belongs.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "patient", "individual", "subject", "mammal", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The term "inhibit", "inhibitor", "suppress" or "suppressor", with respect to a biological activity or process (e.g., DNA repair or pyrimidine synthesis), refers to a decrease in the biological activity or basal activity of the biological process.

The term "activate", "activator", "enhance" or "enhancer", with respect to a biological activity or process (e.g., DNA repair), refers to an increase in the biological activity or basal activity of the biological process.

The term "proliferation" refers to the processes leading to an increase of cell size and/or cell number. As used herein, proliferation may include one or more of the following: tumor cell growth, angiogenesis, innervation, and metastasis.

The term "aberrantly proliferating cells" (or "aberrant cell proliferation") refers to cells having proliferation that deviates from the normal, proper, or expected course. For example, aberrant cell proliferation includes inappropriate proliferation of cells wherein cellular components (e.g., DNA) and/or cellular processes of the cell have become damaged, impaired or defective. Aberrant cell proliferation may also include indications caused by, mediated by, or resulting in inappropriately high levels of cell division, inappropriately low levels of cell death (e.g., apoptosis), or both. Such indications can be characterized, for example, by single or multiple local abnormal proliferations of cells, groups of cells or tissue(s), and include cancerous (benign or malignant) and noncancerous indications. In some embodiments, the aberrantly proliferating cell is a tumor or cancer cell.

As used herein, "tumor" refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "vehicle" or "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "synergy" may be defined as any significant deviation from additivity with regard to a resulting quantifiable biological response when administering two drugs to a subject or to a cell. Synergy, alternatively phrased, is an interaction between two or more drugs that causes the total effect of the drugs to be greater than the sum of the individual effects of each drug. An example of a deviation from additivity would be when a cumulative effect of two drugs used in combination is greater than an effect that would be predicted by summing effects observed for each drug used in isolation.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Methods of the Invention

In one aspect is provided a method for treating an ARID1A-mutant tumor or cancer in a subject in need thereof. In certain embodiments, the method includes administering to the subject an effective amount of a pyrimidine synthesis inhibitor. In certain embodiments, the method further includes administering to the subject an effective amount of a DNA repair inhibitor. In certain embodiments, the method includes administering both a pyrimidine synthesis inhibitor and a DNA repair inhibitor.

In various embodiments, the ARID1A-mutant cells are tumor or cancer cells. In various embodiments, the ARID1A-mutant cells are aberrantly proliferating cells.

ARID1A-Mutant Cells

In various embodiments, the ARID1A-mutant cells are tumor or cancer cells. In some embodiments, the tumor or cancer may be localized or originate anywhere within a subject including, but not limited to, brain, breast, bladder, bone, cartilage, cervix, colon, cornea, eye, neural tissue, glia, esophagus, fallopian tube, heart, pancreas, intestines, gallbladder, kidney, liver, lung, ovary, pancreas, parathyroid, pineal gland, pituitary gland, prostate, spinal cord, spleen, skeletal muscle, skin, muscle, stomach, testis, thymus, thyroid, trachea, urogenital tract, ureter, urethra, uterus, endometrium, vagina, or a combination thereof. In some embodiments the tumor or cancer is in the ovary, uterus, endometrium, vagina, stomach, gallbladder, bladder, or a combination thereof. In certain embodiments, the tumor or cancer can be a gynecologic cancer. In certain embodiments, the tumor or cancer can be a clear cell ovarian cancer, endometrioid ovarian cancer, endometrial cancer, or uterine carcinosarcoma. In some aspects, the cancer is not a PTEN-mutant cancer.

In various embodiments, the ARID1A-mutant cells are aberrantly proliferating cells. In some embodiments, the aberrantly proliferating cells are associated with a cell proliferative disorder or disease such as, but not limited to, a precancerosis, a dysplasia, a metaplasia, psoriasis, psoriatic arthritis, rheumatoid arthritis, benign proliferative skin diseases, ichthyosis, lichen plannus, papilloma, basal cell carcinoma, squamous cell carcinoma, fibroproliferative diseases such as restenosis, vasoproliferative diseases, dermatoproliferative diseases, endometriosises, arteriovenous malformation (AVM) (e.g., brain AVM) and neoplastic diseases of the eye.

Diseases associated with aberrant cell proliferation that can be treated with the methods include, but are not limited to, a tumor, a cancer, a precancerosis lesion, a dysplasia, a metaplasia, psoriasis, psoriatic arthritis, rheumatoid arthritis, benign proliferative skin diseases, ichthyosis, lichen plannus, papilloma, basal cell carcinoma, squamous cell carcinoma, fibroproliferative diseases such as restenosis, vasoproliferative diseases, dermatoproliferative diseases, endometriosises, arteriovenous malformation (AVM) (e.g., brain AVM) and neoplastic diseases of the eye. Other hyperproliferative diseases that may be treated using the methods of the invention include, but are not limited to inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, or oral hairy leukoplakia.

Examples of cancer that can be treated with the methods of the invention include but are not limited to, carcinoma, lymphoma, blastoma, sarcoma, and leukemia. More particular examples of such cancers include breast cancer (including ductal carcinoma in situ (DCIS), invasive breast cancer (ILC or IDC), triple-negative breast cancer, inflammatory breast cancer, Paget disease of the breast, angiosarcoma, and phyllodes tumor), squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, colon cancer, colorectal cancer, endometrial or uterine carcinoma, salivary gland carcinoma, kidney cancer, liver cancer, prostate cancer, vulval cancer, thyroid cancer, hepatic carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion. Additional examples of cancer can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at internet website of Merck Manuals); and SEER Program Coding and Staging Manual 2016, each of which are incorporated by reference in their entirety for all purposes. A cancer may be diagnosed using criteria generally accepted in the art, including the presence of a malignant tumor.

Pyrimidine Synthesis Inhibitor

The pyrimidine synthesis inhibitor may be a small molecule, protein, fusion protein, peptide, nucleic acid, aptamer, avimer, or derivatives or fragments thereof.

The pyrimidine synthesis inhibitor may be any molecule or compound, optionally one of those listed immediately supra, where the molecule or compound is capable of inhibiting the expression, activation, or enzymatic activity of proteins mediating pyrimidine synthesis in a cell or, alternatively, where the molecule or compound is capable of modifying the availability of particular metabolites in a cell (e.g., through sequestration, binding, chelation, or chemical modification).

In certain embodiments, the pyrimidine synthesis inhibitor is an inhibitor of orotate phosphoribosyl transferase, an inhibitor of orotidylate decarboxylase, a direct inhibitor of CAD (a trifunctional multi-domain enzyme including carbamoyl phosphate synthetase II, aspartate transcarbamoylase, and dihydroorotase), a ribosomal protein S6 kinase beta-1 (S6K1) inhibitor, a mammalian target of rapamycin complex 1 (mTORC1) inhibitor, an inhibitor of mTORC1 signaling, or a combination thereof. In some embodiments, the pyrimidine synthesis inhibitor is an inhibitor of any protein involved in signaling or enzymatic activity correlated with pyrimidine synthesis in a cell.

The pyrimidine synthesis inhibitor may be a direct or indirect inhibitor of pyrimidine synthesis. An example of a direct inhibitor of pyrimidine synthesis is any compound or molecule that through a direct physical interaction with an enzyme modifies activity of the enzyme which catalyzes a reaction necessary for synthesis of pyrimidine in a cell, wherein a product of the reaction is or ultimately becomes a pyrimidine molecule. An example of an indirect inhibitor of pyrimidine synthesis is any compound or molecule modifying functionality of an enzyme or protein involved in promoting expression of enzymes involved in pyrimidine synthesis in a cell or any compound or molecule modifying functionality of an enzyme that catalyzes or otherwise facilitates activation or an increase in activity of an enzyme involved in pyrimidine synthesis (e.g., a phosphorylase, a phosphatase, a kinase, a signaling protein, or a protein that physically interacts or otherwise binds to an enzyme involved in pyrimidine synthesis).

In some embodiments, the pyrimidine synthesis inhibitor is a dihydroorotate dehydrogenase (DHODH) inhibitor. The DHODH inhibitor may be administered to a subject at a dose effective in reducing tumor size or cancer cell count in a subject or in a biological sample. The DHODH inhibitor may be any compound or molecule (alternatively, a drug) known to one of skill in the art to inhibit the enzymatic activity, activation, or expression of DHODH. Non-limiting examples of DHODH inhibitors include teriflunomide, leflunomide, or a combination thereof.

Teriflunomide can be administered at a dose from about 1 mg to about 200 mg, from about 1 mg to about 100 mg, from about 2 mg to about 50 mg, or from 2.5 mg to about 25 mg, from about 2.5 mg to about 200 mg, or from about 5 mg to about 50 mg. In various embodiments, teriflunomide is administered at about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg.

Leflunomide can be administered at a dose from about 1 mg to about 200 mg, from about 1 mg to about 100 mg, from about 2 mg to about 80 mg, from about 4 mg to about 40 mg, or from about 8 mg to about 20 mg. In various embodiments, leflunomide is administered at about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg.

In some embodiments, the pyrimidine synthesis inhibitor is an inhibitor of S6K1. The S6K1 inhibitor may be any compound or molecule (alternatively, a drug) known to one of skill in the art to inhibit enzymatic activity, activation, or expression of S6K1. A non-limiting example of an S6K1 inhibitor is PF-4708671.

The S6K1 inhibitor may be administered to a subject at a dose effective in reducing tumor size or reducing cancer cell count in a subject or in a biological sample. As non-limiting examples, PF-4708671 can be administered at a dose from about 0.1 mg to about 100 mg, from about 0.5 to about 50 mg, about 1 mg to about 25 mg, from about 2 mg to about 50 mg, or from about 2.5 mg to about 25 mg. In various embodiments, PF-4708671 is administered at about, at least about, or no more than about 0.1 mg, 0.25 mg, 0.5 mg, 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg.

DNA Repair Inhibitor

The DNA repair inhibitor may be a small molecule, protein, fusion protein, peptide, nucleic acid, aptamer, avimer, or derivatives or fragments thereof The DNA repair inhibitor may be any molecule or compound, optionally one of those listed supra, where the molecule or compound is capable of inhibiting the expression, activation, or enzymatic activity of proteins mediating DNA repair in a cell or, alternatively, where the molecule or compound is capable of modifying the availability of particular metabolites in a cell (e.g., through sequestration, binding, chelation, or chemical modification) involved in DNA repair. In certain embodiments, the DNA repair inhibitor inhibits activity or expression of a protein involved in cell signaling activated by DNA damage (e.g., ATR, ATM, JNK).

In some embodiments, the DNA repair inhibitor directly or indirectly inhibits activity or expression of an enzyme that catalyzes repair of DNA damage (e.g., inhibitors of SIRT6, MRE11, BRCA1, BRCA2, or DNA-PDcs). Non-limiting examples of DNA damage include mismatch, pyrimidine dimes, alkylation, and double-strand breaks, or various combinations thereof. The DNA repair inhibitor may be a direct or indirect inhibitor of DNA repair. An example of a direct inhibitor of DNA repair is any compound or molecule modifying through direct physical interaction activity of an enzyme catalyzing a reaction necessary for repair of damaged DNA in a cell, wherein a product of the reaction is or ultimately becomes a non-damaged DNA molecule. An example of an indirect inhibitor of DNA repair is any compound or molecule modifying functionality of an enzyme or protein involved in promoting expression or proper recruitment to a location within a cell of enzymes involved in DNA repair in the cell or any compound or molecule modifying functionality or recruitment of an enzyme that catalyzes or otherwise facilitates activation or an increase in activity of an enzyme involved in DNA repair (e.g., a phosphorylase, a phosphatase, a kinase, a signaling protein, or a protein that physically interacts or otherwise binds to an enzyme involved in DNA repair).

In some embodiments the DNA repair inhibitor is an inhibitor of ATR. The ATR inhibitor may be any compound or molecule (alternatively, a drug) known to one of skill in the art to inhibit enzymatic activity, activation, or expression of S6K1. Non-limiting examples of inhibitors of ATR include AZD6738, VX-970, or a combination thereof.

The DNA repair inhibitor may be administered to a subject at a dose effective in reducing tumor size or reducing cancer cell count in a subject or in a biological sample. In some embodiments, the DNA repair inhibitor is a Parp inhibitors (e.g., olaparib, niraparib, rucaparib). In embodiments, the DNA repair inhibitor is a CHK1 inhibitor.

VX-970 can be administered at a dose from about 0.5 mg to about 200 mg, from about 1 mg to about 100 mg, from about 10 mg to about 100 mg, or from about 2 mg to about 50 mg. In various embodiments, VX-970 is administered at about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg.

AZD6738 can be administered at a dose from about 1 mg to about 500 mg, from about 10 mg to about 480 mg, from 10 mg to about 300 mg, or from about 20 mg to about 240 mg, from about 40 mg to about 120 mg, or from about 1 mg to about 50 mg. In various embodiments, AZD6738 is administered at about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, or 400 mg.

Combination Treatment

The pyrimidine synthesis inhibitor and the DNA repair inhibitor are each administered to a subject at dosages, frequencies, and by a route resulting in a reduction in tumor size or cancer cell count or cell survival rate. The drugs administered may be independently administered at times, which may include administrations that are simultaneous, non-simultaneous, or various combinations thereof. As non-limiting examples, each drug may be administered at different frequencies, at different times, or by different routes of entry. In some embodiments, the drugs can be administered simultaneously and/or the drugs may be administered so that each drug is simultaneously present within a subject.

In certain embodiments, the pyrimidine synthesis inhibitor and the DNA repair inhibitor are each administered in a therapeutically effective amount. In certain embodiments, the combination therapy results in a synergistic effect. The dosages of the composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly, biweekly, or every other day or fractionated into smaller doses and administered daily, semi-weekly, etc., to maintain an effective dosage level. It is contemplated that a variety of doses will be effective to achieve the intended effect.

In various embodiments each drug is administered by a common route of entry. In some embodiments, all drugs are administered orally. Non-limiting examples of routes of entry by which each drug may be administered include orally, intravenously, transdermally, by inhalation, or rectally. In certain embodiments, the compositions are formulated for parenteral administration, e.g., intravascular (intravenous or intraarterial), intraperitoneal, intratumoral, intraventricular, intrapleural or intramuscular administration. In certain embodiments, the composition is reconstituted from a lyophilized preparation prior to administration.

The drugs can each administered periodically and at a predetermined frequency to a subject. Non-limiting examples of frequencies include from about 1 to about 24 hours, from about 1 to about 48 hours, from about 1 hour to about 7 days, from about 1 hour to about 8 hours, from about 1 day to about 2 days, about 8 hours, about 12 hours, less than 1 hour, and about 24 hours. In some embodiments, teriflunomide is administered daily. In some embodiments, leflunomide is administered daily. In some embodiments, VX-90 is administered daily or every other day. In some embodiments, AZD6738 is administered twice daily. One of skill in the art will understand that subjects may administer a drug at varying frequencies on account of various individual circumstances; therefore, the time periods and frequencies listed herein represent advised, recommended, or ideal average frequencies of administration around which actual self-administration regimens may vary from subject to subject.

It is also contemplated that when used to treat various diseases/disorders, the methods and compositions of the present invention can be utilized with additional therapeutic methods/agents suitable for the same or similar diseases/disorders. In certain embodiments, such other therapeutic methods/agents can be co-administered (simultaneously or sequentially) to generate additive or synergistic effects. Suitable therapeutically effective dosages for each agent may be lowered due to the additive action or synergy.

In some embodiments, the methods and/or compositions of the present invention can be used in combination with at least one additional cancer therapy. For example, the methods and/or compositions of the invention can be used in combination with conventional cancer therapies, such as, e.g., surgery, chemotherapy or combinations thereof, depending on type of the tumor, patient condition, other health issues, and a variety of factors. Non-limiting examples of cancer therapies also include radiation therapy, bone marrow transplant, immunotherapy, hormone therapy, targeted drug therapy, cryoablation, and radiofrequency ablation. In some embodiments, the additional cancer therapy includes administering to a subject at least one chemotherapeutic agent that is not a pyrimidine synthesis inhibitor or a DNA repair inhibitor. In certain embodiments, the radiation is X-rays, gamma rays, alpha particles, beta particles, proton beams, neutron beams, or negative Pi mesons.

In certain embodiments, other therapeutic agents useful for combination cancer therapy with the methods and/or compositions of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain, Nature. 2000 Sep. 14; 407(6801):249-57, which is incorporated herein by reference in its entirety for all purposes. In one embodiment, methods and/or compositions of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present invention include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

The methods and/or compositions of the invention may also be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e). The methods of the invention can also be combined with other treatments such as midostaurin, enasidenib, or a combination thereof.

In one embodiment of any of the above methods of the invention, the method further comprises administering to the subject one or more additional compounds selected from immuno-suppressives, biologicals, probiotics, prebiotics, and cytokines (e.g., IFN or IL-2). As another non-limiting example, methods and/or compositions of the invention can also be combined with other therapies that block inflammation (e.g., via blockage of IL1, INFα/β, IL6, TNF, IL23, etc.).

Use of a Kit

In various aspects is provided a method for using a kit (described below) to treat an ARID1A-mutant tumor or cancer in a subject in need thereof. The method comprises administering compositions of the kit to treat a subject. The compositions may individually be administered according to any of the methods described herein. The compositions of the kit may be used for decreasing proliferation of an aberrantly proliferating cell by contacting the aberrantly proliferating cell with the compositions of the kit.

Determining Presence of ARID1A Mutation

In some aspects, the method further includes determining the presence of an ARID1A mutation in cell genomes of a subject prior to administering the pyrimidine synthesis inhibitor and/or the DNA repair inhibitor. It will be understood by one of skill in the art that determining that a subject harbors an ARID1A mutation constitutes establishing a high or reasonable (more likely than not) probability that aberrantly proliferating cells within the subject will also harbor an ARID1A mutation or, further, that the aberrantly proliferating cells may be part of an ARID1A mutant cancer or tumor.

Kits of the Invention

In another aspect is provided a kit. The kit comprises a) a composition comprising the pyrimidine synthesis inhibitor, b) a composition comprising the DNA repair inhibitor, and, optionally, c) instructions for use of the pyrimidine synthesis inhibitor composition and the DNA repair inhibitor composition in the treatment of an ARID1A-mutant tumor, cancer, or disease associated with aberrantly proliferating cells.

In another aspect is provided a kit. The kit comprises a) a composition comprising the pyrimidine synthesis inhibitor and a composition comprising the DNA repair inhibitor, and, optionally, b) instructions for use of the pyrimidine synthesis inhibitor composition and the DNA repair inhibitor composition in the treatment of an ARID1A-mutant tumor, cancer, or disease associated with aberrantly proliferating cells.

In certain embodiments, the pyrimidine synthesis inhibitor composition comprises the pyrimidine synthesis inhibitor(s) disclosed above and in the concentrations disclosed above.

In some embodiments, the pyrimidine synthesis inhibitor composition comprises from about 0.1 mg to about 1 g, from about 0.1 mg to about 100 mg, from about 0.5 to about 50 mg, from about 1 mg to about 500 mg, from about 1 mg to about 200 mg, from about 1 mg to about 100 mg, about 1 mg to about 25 mg, from about 2 mg to about 500 mg, from about 2 mg to about 200 mg, from about 2 mg to about 100 mg, from about 2 mg to about 80 mg, from about 2 mg to about 50 mg, from about 2.5 mg to about 1 g, from 2.5 mg to about 40 mg, from about 2.5 mg to about 25 mg, from about 4 mg to about 40 mg, from about 5 mg to about 50 mg, or from about 8 mg to about 20 mg of the pyrimidine synthesis inhibitor. In various embodiments, the pyrimidine synthesis inhibitor composition comprises about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1 g.

In certain embodiments, the DNA repair inhibitor composition comprises the DNA repair inhibitor(s) disclosed above and in the concentrations disclosed above.

In some embodiments, the DNA repair inhibitor composition comprises from about 0.1 mg to about 1 g, from about 1 mg to about 1 g, from about 1 mg to about 500 mg, from about 1 mg to about 100 mg, from about 1 mg to about 50 mg, from about 2 mg to about 50 mg, from about 10 mg to about 480 mg, from about 10 mg to about 300 mg, from about 10 mg to about 100 mg, from about 20 mg to about 240 mg, or from about 40 mg to about 120 mg of the DNA repair inhibitor. In various embodiments, the DNA repair inhibitor composition comprises about, at least about, or no more than about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1 g.

In an embodiment, a method is provided comprising using the kit to treat ARID1A-mutant tumor or cancer cells (alternatively, an ARID1A-mutant tumor or cancer) in a subject in need thereof. The method includes administering the pyrimidine synthesis inhibitor and the DNA repair inhibitor as described supra.

Dosage Forms

In various embodiments of the invention, compositions of the kit are present in one or more dosage forms for treating a subject. For example, compositions can be administered in solid or liquid form. Examples of solid dosage forms include, but are not limited to, individual units present in capsules or tablets as powders or granules, or present in tablets conventionally formed by compression molding. Such compressed tablets can be prepared by compression of three or more drugs and a pharmaceutically acceptable carrier in a suitable machine. Molded tablets can optionally be coated or grooved to have inscriptions on the tablets. Tablets can be formulated for immediate release, substantial immediate release, delayed release, controlled release, or extended release. In addition, dosage forms of the present invention can include acceptable carriers or salts known in the art (Handbook of Pharmaceutical Excipients, American Pharmaceutical Association (1986), which is incorporated herein by reference in its entirety).

In various embodiments, dosage forms for treating a subject include tablets, capsules, gels, orally disintegrating tablets, multilayer tablets, effervescent tablets, beads, chewing lozenges, lozenges, oral syrups, powders, lollipops, parenteral, intrathecal injection, inhalation, nasal sprays, transdermal patches, iontophoresis, and absorbent gels. Further dosage forms include liquid, liquid tannate, suppository, injection, IV drip, and combinations thereof.

In current embodiments, the composition of the present invention comprises the agent in immediate release, immediate release, controlled release, extended release, other release dosage form or pattern, or combinations thereof.

Excipients suitable for inclusion in compositions of the present disclosure include diluents, binders, disintegrants, dispersants, lubricants, glidants, stabilizers, interfaces. An activator and a colorant are included. Diluents, also called "fillers," can be used to increase tablet bulk so that a practical size for tableting is obtained. Non-limiting examples of diluents include lactose, cellulose, microcrystalline cellulose, mannitol, dry starch, hydrolyzed starch, powdered sugar, talc, Sodium chloride, silicon dioxide, titanium oxide, dicalcium phosphate dihydrate, calcium sulfate, calcium carbonate (calcium calcium) alumina, and kaolin). A binder can impart tackiness to the tablet formulation, and the binder can be used to help keep a tablet intact after tableting. Non-limiting examples of suitable binders include starch (including corn starch and pregelatinized starch), gelatin, sugars (e.g., glucose, dextrose, sucrose, lactose, sorbitol, cellulose, polyethylene glycol, wax, natural rubber and synthetic rubber (e.g., natural and synthetic gums), acacia, tragacanth, sodium alginate, and synthetic polymers (polymethacrylates, polyvinylpyrrolidone, etc.). Non-limiting examples of lubricants include magnesium stearate, calcium stearate, stearic acid, glyceryl behenate, and polyethylene glycol. Disintegrants can facilitate tablet disintegration after administration, and non-limiting examples thereof include starch, alginic acid, cross-linked polymers (e.g., cross-linked polyvinyl pyrrolidone), croscarmellose sodium, glycol potassium acid starch, potassium or sodium starch glycolate, clay, cellulose, starch, gum, and combinations thereof. Non-limiting examples of suitable glidants include silicon dioxide and talc. Stabilizers can inhibit or delay drug degradation reactions (including oxidation reactions). Surfactants can also include and can be anionic, cationic, amphoteric, or nonionic surfactants. If desired, tablets may also contain non-toxic adjuvants (pH buffering agents, preservatives (e.g., antioxidants), wetting agents or emulsifying agents). Compositions of the present disclosure may further include solubilizing agents, coating agents, and/or flavoring agents.

Controlled release formulations can include one or more combinations of excipients that delay the release of the drug by coating the active drug or by transient binding or by reducing its solubility. Examples of these excipients include cellulose ethers (such as hydroxypropyl methylcellulose or silicified microcrystalline cellulose), polyvinyl acetate-based excipients, and methacrylate and methacrylic acid-based polymers and copolymers. In some embodiments, a composition is formulated for extended or controlled release.

Immediate release formulations include one or more combinations of excipients capable of rapid release (such as 1 minute to 1 hour after administration) of a pharmaceutically active agent (such as the pyrimidine synthesis inhibitor or the DNA repair inhibitor). In one embodiment, the immediate release excipient is microcrystalline cellulose, sodium carboxymethyl cellulose, sodium starch glycolate, corn starch, colloidal silica, sodium lauryl sulfate, magnesium stearate, croscarmellose sodium, crospovidone NF, Avicel PH200, and combinations thereof.

Pharmaceutical carriers or vehicles suitable for administration of compositions provided herein include all such carriers known to those skilled in the art to be appropriate for a particular mode of administration.

Compositions disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions may further comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods

The following materials and methods were used, unless described otherwise in a specific Example.

Plasmids. HA-tagged full-length ARID1A (SEQ ID NO: 4) was amplified by PCR from pCNA6-V5/His-ARID1A (provided by I.-M. Shih8) and subcloned into the pCIN4 expression vector[20]. To construct the expression plasmids for GST-CAD (SEQ ID NO: 5) and GST-CAD fragments (SEQ ID NO: 6-9), cDNA sequences of full-length CAD and its fragments were amplified by PCR from pcDNA3.1-HisFlag-CAD (Addgene) and subcloned into the pGEX 4T-2 vector (GE Healthcare Life Sciences) for expression in BL21 bacteria. V5-tagged full-length BAF250a (SEQ ID NO: 10); V5-tagged BAF250a fragment, amino acids 1-1758 (SEQ ID NO: 11); and V5-tagged BAF250a fragment, amino acids 1759-2285 (SEQ ID NO: 12), were created by G. R. Crabtree7 and obtained from Addgene. Short hairpin RNA (shRNA) lentiviral plasmids were kindly provided by I.-M. Shih8. shRNA sequences for ARID1A were as follows: sh1 (TRCN0000059090), target sequence CCTCTCTTATACACAGCAGAT (SEQ ID NO: 1), and sh2 (TRCN0000059091), target sequence CCGTTGAT-GAACTCATTGGTT (SEQ ID NO: 2). The vector backbone is pLKO.1. V5/His-tagged pLenti-puro-LacZ and pLenti-puro-ARID1A were obtained from Addgene.

Antibodies and Drugs. Antibodies for ARID1A, CAD, CAD (for immunohistochemistry, IHC), and βactin were from Bethyl Laboratories. Antibodies for BRG1 (SMARCA4), Phospho-CAD (phosphorylated at Serine 1859), Phospho-CHK1 (phosphorylated at Serine 345), phosphor-Histone H2AX (γH2AX), HA, V5, RPS6, Phospho-RPS6, and GAPDH were from Cell Signaling Technology. Anti-IgG and HRP-labeled anti-rabbit secondary antibodies were from Invitrogen. Leflunomide was from Enzo Life Sciences. Teriflunomide and PF-4708671 were from Tocris. AZD6738 was from ChemScene. VX-970 (VE-822) was from Selleck Chemicals.

Cell Lines. Adherent cell lines were cultured in RPMI 1640 (from Gibco) supplemented with 10% fetal bovine serum (from Gibco) and 1% penicillin-streptomycin (from Gibco) at 37° C., 5% CO2. Low-passage-number cells were used, and all cell lines tested negative for mycoplasma using the MycoAlert Mycoplasma Detection Kit (from Lonza). The following ovarian and endometrial cancer cell lines were used: ES26, KLE5, SKOV3, OVISE (from JCRB Cell Bank), and HEC-1-A5 cells and their stably transfected subclones, as described below. Cell lines were authenticated using the GenePrint10 kit (form Promega) and matching to their original profiles (at ATCC). ARID1A protein expression status was confirmed by immunoblotting. HEK293FT cells were from Thermo Fisher Scientific. ARID1A-knockout HCT116 (homozygous truncating mutations, Q456*/Q456*) and ARID1A-wildtype HCT116 colorectal carcinoma cells were from Horizon Discovery.

Mass Spectrometry Analysis of the Immunopurified ARID1A Complex. Immunoprecipitated ARID1A protein complex was separated by gel electrophoresis, followed by peptide analysis of digested gel bands by C18 reversed-phase chromatography using an UltiMate 3000 RSLCnano System (from Thermo Scientific) equipped with an Acclaim PepMap C18 column (from Thermo Scientific) and connected to a TriVersa NanoMate nanoelectrospray source (from Advion) and a linear ion trap LTQ XL mass spectrometer (from Thermo Scientific). Protein identification was performed using Mascot search engine v. 2.5.1 (from Matrix Science) against the NCBI *Homo sapiens* database. Scaffold software v. 4.5.1 (from Proteome Software) was used to validate MS/MS peptide and protein identification based on 95% peptide and 99% protein probabilities, respectively.

Immunoblot Analysis and Co-Immunoprecipitation Assay. For immunoblotting experiments, cells were lysed in BC200 lysis buffer [20 mM Tris-HCl (pH 7.5), 200 mM NaCl, 1 mM EDTA, 0.2% Nonidet P-40 (NP-40), freshly added complete protease inhibitor cocktail (from Roche), and PhosSTOP phosphatase inhibitor (from Roche)] or in boiling SDS lysis buffer [1% SDS and 10 mM Tris-Cl (pH 7.5)], as previously described[21]. Protein concentrations were quantified using a modified Lowry assay, and equal protein amounts were loaded onto a 10% SDS-PAGE gel and separated by gel electrophoresis, followed by transfer to a nitrocellulose membrane. The nitrocellulose membrane was stained with Ponceau S to confirm equal protein loading and then blocked in 2% BSA in Tris-buffered saline with 0.1% Tween-20 (tris buffered saline with tween, or TBST). Primary antibody incubation was done for 2 h at room temperature or, for phospho-specific antibodies, overnight at 4° C. An HRP-conjugated secondary antibody was used, followed by detection using enhanced chemiluminescence substrate (from Pierce). Autoradiograph images were scanned and saved as unmodified TIFF images, and densitometry analysis was done with ImageJ (from NIH) software.

For co-immunoprecipitation, cells were lysed in BC150 lysis buffer [20 mM Tris-HCl (pH 7.5), 150 mM NaCl, 10% glycerol, 1 mM EDTA, 0.2% NP-40, and freshly added complete protease inhibitor cocktail (from Roche)]. Cell lysates were incubated with primary antibody or IgG control antibody at 4° C. overnight, followed by incubation with Protein A Agarose beads (from Sigma-Aldrich) for 1 h at 4° C. After five washes with lysis buffer, the bound proteins were eluted from the beads in 2× Laemmli SDS sample loading buffer at 95° C. for 5 min and then loaded onto a 10% SDS-PAGE gel. Proteins were transferred to nitrocellulose membranes, and immunoblotting was performed as described above.

Glutathione S Transferase (GST) Protein-Protein Interaction Assay. Recombinant proteins, GST, GST-tagged CAD (SEQ ID NO: 5), and GST-tagged CAD fragments (SEQ ID NO: 6-9), see FIG. 2A, were purified as previously described[22]. HEK293T cells were transfected with pCIN4-HA-ARID1A using Lipofectamine 3000 (from I nvitrogen). Forty-eight hours later, the cells were lysed in lysis buffer [50 mM Tris-HCl (pH 8), 5 mM EDTA, 150 mM NaCl, 0.5% NP-40, and freshly added 1 mM DTT and complete protease inhibitor cocktail (from Roche)]. The HEK293T lysates were then incubated for 2 h at 4° C. with 25 µg Glutathione Sepharose 4B beads (from Amersham) bound to GST-CAD (SEQ ID NO: 5) or its fragments (SEQ ID NO: 6-9). After washing in lysis buffer, bound proteins were eluted from the beads with 2× Laemmli SDS sample loading buffer at 95° C. for 5 min, loaded onto a 10% SDS-PAGE gel, and then transferred to a nitrocellulose membrane and immunoblotted using the indicated primary antibodies.

To evaluate the domain of ARID1A that potentially interacts with GST-ATCase, HEK293T cells were transfected with pCDNA6-V5/His.b (empty vector), pcDNA6-ARID1A 1-1758 (N-terminus), pcDNA6-ARID1A 1759-2285 (C-terminus), or pcDNA6-ARID1A (full-length) expression plasmid using Lipofectamine 3000 (from Invitrogen). Forty-eight hours later, the cells were lysed as described above. Lysates were then incubated for 2 h at 4° C. with 25 µg Glutathione Sepharose 4B beads (Amersham) bound to GST or GST-ATCase. After washing in lysis buffer, bound proteins were eluted from the beads in 2× Laemmli SDS sample loading buffer at 95° C. for 5 min and then loaded onto an SDS-PAGE gel, followed by transfer to a nitrocellulose membrane and immunoblotting using the indicated primary antibodies.

Short Hairpin RNA (shRNA)-Mediated Knockdown and Expression of ARID1A in ovarian and endometrial carcinoma cells. shRNA lentiviral supernatants were produced using standard protocols, as previously described[8]. Vectors were transfected into HEK293FT cells using X-tremeGENE 9 DNA Transfection Reagent (from Roche). Retroviral supernatants isolated at 48 h were diluted 1:1 in culture medium and used to infect ARID1A-wildtype ES2 and KLE cell lines. Stably transfected subclones were expanded using puromycin (from Dot Scientific) drug selection. For expression of ARID1A in the ARID1A-mutant HEC-1-A cell line, pCIN4-HA-ARID1A was transfected using X-tremeGENE 9 DNA Transfection Reagent (from Roche), followed by selection with G418 (from Gibco). For expression of ARID1A in the ARID1A-mutant SKOV3 and OVISE cell lines, V5/His-tagged pLenti-puro-LacZ and pLenti-puro-ARID1A were transfected using lentivirus. Lentivirus was produced using HEK293FT cells with the second-generation packaging system pSPAX2 (Addgene plasmid) and pMD2.G (Addgene plasmid). Stably transfected subclones were expanded using puromycin and blasticidin (Gibco) drug selection.

14C aspartate incorporation into RNA and DNA. Cells were plated in 60-mm² dishes 48 h prior to experiment (cells grew to 85-90% confluent when the experiment started). Fresh medium was added to the subconfluent cells, and 5 µCi L-[U-$^{14}$C]aspartic acid (0.1 mCi/mL, PerkinElmer) was added to each plate. After 6 h of incubation at 37° C., the cells were lysed, and RNA and DNA were prepared following a manufacturer's manual for the AllPrep DNA/RNA Mini Kit (from Qiagen). The amounts of RNA and DNA were quantified, and the radioactivity in each sample was determined by liquid scintillation. [$^{14}$C]Aspartate incorporation into RNA or DNA was respectively normalized to the amount of RNA or DNA and expressed as cpm/µg RNA or cpm/µg DNA.

Uridine Triphosphate (UTP) assay. UTP was examined with an enzyme immuno-based plate-reader assay according to manufacturer's recommendations (Aviva Systems Biology). Briefly, cells were cultured in medium with or without drug treatment. For metabolite extraction, the medium was aspirated, and the same number of cells were collected by trypsinizing and counting. The cells were lysed by ultrasonication (Qsonica Q125; Time: 2 min, Pulse: 15 s on/15 s off, Amplitude: 50%). Insoluble material in lysates was pelleted by centrifugation at 12,000 rpm for 10 min at 4° C. Metabolite-containing supernatants were assessed using a UTP ELISA Kit. Plates were read at 450 nm with a standard microplate reader. UTP level was calculated using the formula (Relative OD450)=(Well OD450)−(Mean Blank Well OD450).

Cytotoxicity assay. Cells were seeded in 96-well plates, with 2000 cells in 100 µL/well, and cultured for 24 h. The cells were treated with serial dilutions of drugs or without drug for an additional 72 h. Cell number was determined using a sulforhodamine B (SRB) assay, as previously described[23]. Briefly, cells were fixed with 20% trichloroacetic acid (TCA), air-dried, and stained with 0.4% SRB dissolved in 1% acetic acid. After washing, protein-bound dye was solubilized with 10 mM unbuffered Tris-base solution (pH 10.5) and detected at 510 nm using a microplate reader. Percentage of cell-growth was calculated using the following formula:

% cell growth=[(Absorbance sample)/(Absorbance untreated)]×100

Using CalcuSyn software (Biosoft), dose-effect curves were generated, and drug concentrations corresponding to a 50% decrease in cell number (IC50) were determined.

Immunofluorescence. Cells plated on coverslips were kept in medium. For detecting proteins, coverslips were fixed with 2% paraformaldehyde for 10 min, permeabilized with 0.5% Triton X-100 for 10 min, and blocked with 1% BSA in 20 mmol/L Tris-HCl (pH 7.5) for 20 min. The coverslips were then incubated with primary antibody (anti-ARID1A, 1:500; anti-CAD, 1:50; or P-CAD Ser1859, 1:50) overnight at 4° C. and with secondary antibody for 2 h at room temperature. For multicolor staining, an additional blocking step was conducted after the first secondary antibody staining. DAPI was used to label the nucleus. Images of cells were acquired using a BZ-X710 fluorescence microscope (from KEYENCE) and analyzed using ImageJ (from NIH).

Immunohistochemistry (IHC). IHC was performed by incubating FFPE tissue section slides in antigen retrieval solution [0.01 M sodium citrate (pH 6.0)] for 20 min in a pressure cooker. The slides were blocked in blocking solution (5% goat serum and 2% BSA in TBS) for 30 min and then incubated with primary antibodies (anti-ARID1A, 1:500; anti-CAD, 1:50) overnight at 4° C. The slides were then incubated with a secondary antibody from an EnVision G12 Doublestain System (from DAKO) for 10 min at room temperature, followed by DAB staining for visualization. The slides were counterstained with hematoxylin and bluing in PBS, dehydrated in graded alcohol, cleared in xylene, and coverslipped in Permount (from Fisher Scientific). Images were visualized using a BZ-X710 fluorescence microscope (from KEYENCE) and analyzed using ImageJ (from NIH).

Animal Model. All animal procedures were conducted in accordance with a protocol approved by the Institutional Animal Care and Use Committee at Yale University.

Three mouse experiments were performed: (i) to assess an effect of teriflunomide on ES2 cells in vivo, (ii) to assess an effect of teriflunomide on SKOV3 cells in vivo, and (iii) to assess a combination effect of teriflunomide and AZD6738 on ES2-shARID1A cells in vivo. All experiments were performed using subcutaneous cell-xenograft models generated by injecting cells into the flanks of 6-week-old female athymic NCr-nu/nu mice (Charles River Laboratories).

Animal-human dose translation was calculated as previously described[24]. Tumor volumes were measured every other day by caliper to determine tumor volume using the formula (length/2)×(width$^2$). Animal weights were recorded, and mice were observed for any toxicities. Experiments were terminated when mean tumor volume of a vehicle ES2-shCon group reached 1000 mm$^3$. Tumor xenografts were excised at time of euthanasia. Representative samples were flash-frozen in liquid nitrogen for subsequent protein expression analysis by immunoblotting, as well as being formalin-fixed paraffin-embedded (alternatively, FFPE) for subsequent hematoxylin and eosin staining and immunohistochemical analysis. FFPE sections were reviewed by a pathologist (alternatively, P.H.), and cellular necrosis was quantified as % cross-sectional area of bisected tumor xenografts.

Figure 4:
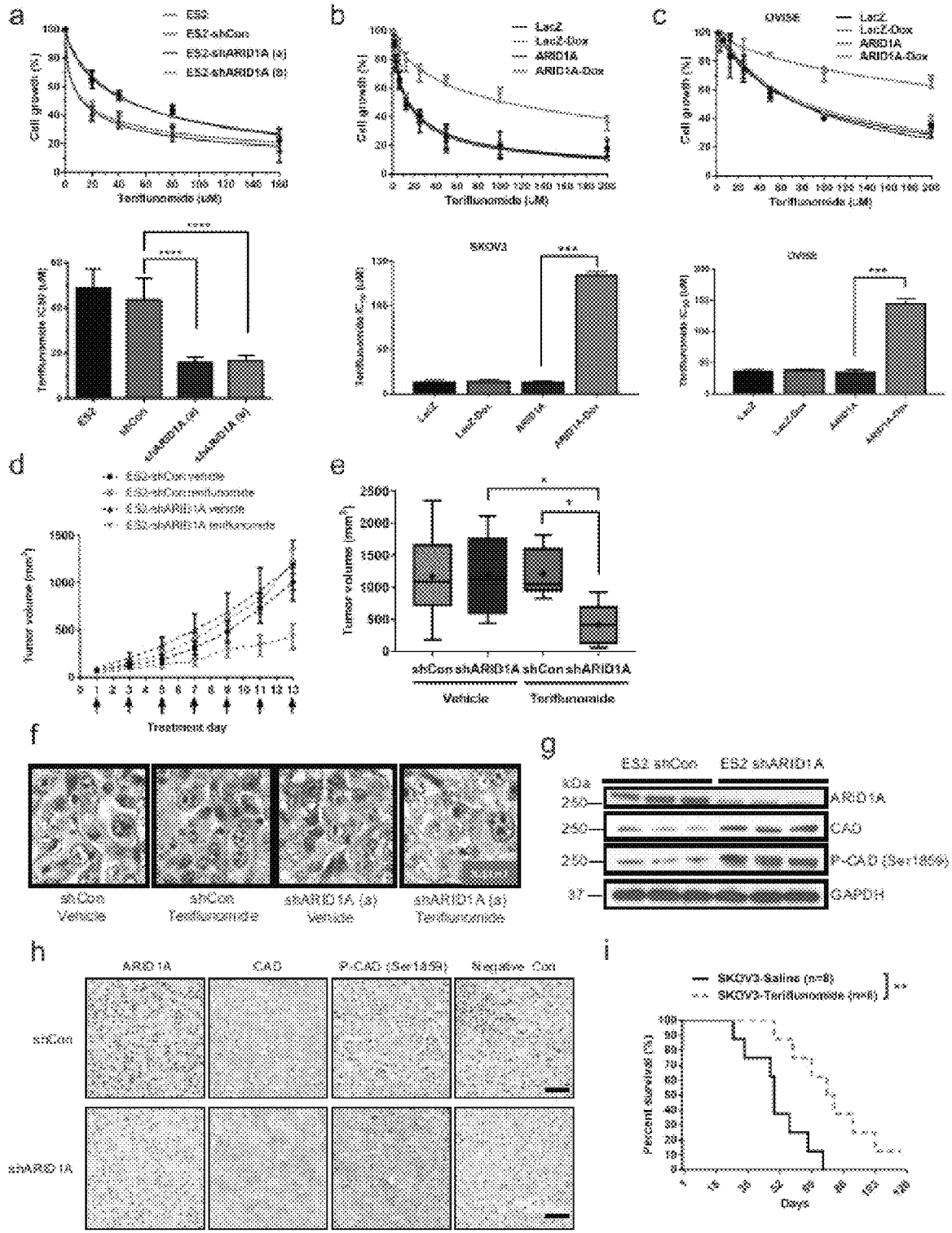
FIGS. 4A-4I show that ARID1A-deficiency increases sensitivity to DHODH inhibitors.

(i) To assess the effect of teriflunomide on ES2 cells, xenograft models were generated by injecting ES2-shCon or ES2-shARID1A cells (1×10$^6$ cells) subcutaneously. When mean tumor volume reached approximately 100 mm$^3$, animals were randomized into treatment groups; mice with xenograft volume <20 mm$^3$ or >160 mm$^3$ were excluded. Teriflunomide was solubilized in DMSO and diluted to 0.5 mg/mL with PBS. Treatment with teriflunomide or vehicle was initiated 24 h after tumor injection. Mice were treated with teriflunomide (4 mg/kg) or vehicle intraperitoneally every other day, as shown in FIG. 4D.

(ii) To assess the effect of teriflunomide on SKOV3 cells, xenograft models were generated by injecting SKOV3 cells [2×10$^6$ cells mixed 1:1 (v/v) with Matrigel (from BD Biosciences)] subcutaneously. When mean tumor volume reached approximately 100 mm$^3$, animals were randomized into treatment groups. Teriflunomide treatment was used the same way as in ES2 xenograft models. A survival curve is shown in FIG. 4J; terminal tumor volume was 1000 mm$^3$.

(iii) To assess the combination effect of teriflunomide and AZD6738 on ES2-shARID1A cells in vivo, xenograft models were generated by injecting ES2-shARID1A cells [2×10$^6$ cells mixed 1:1 (v/v) with Matrigel (from BD Biosciences)] subcutaneously. When the mean tumor volume reached approximately 100 mm$^3$, the animals were randomized into treatment groups. Teriflunomide treatment was used the same way as in the ES2 xenograft models. AZD6738 was solubilized in DMSO and diluted to 0.5 mg/mL with 10% 2-hydroxypropyl-b-cyclodextrin. Treatment with AZD6738 (25 mg/kg) or vehicle was performed daily by oral gavage, as shown in FIG. 5J.

Statistics. An independent-samples t-test was applied when two groups of data were compared. Multiple-group comparisons were done using one-way analysis of variance (ANOVA) with Tukey's post-test. Statistical analyses and graphing were performed using SPSS 22 (from IBM) and Prism 7 (from GraphPad). P-values less than 0.05 were considered significant.

Example 1: Demonstrating that ARID1A Interacts with CAD

Figure 6:
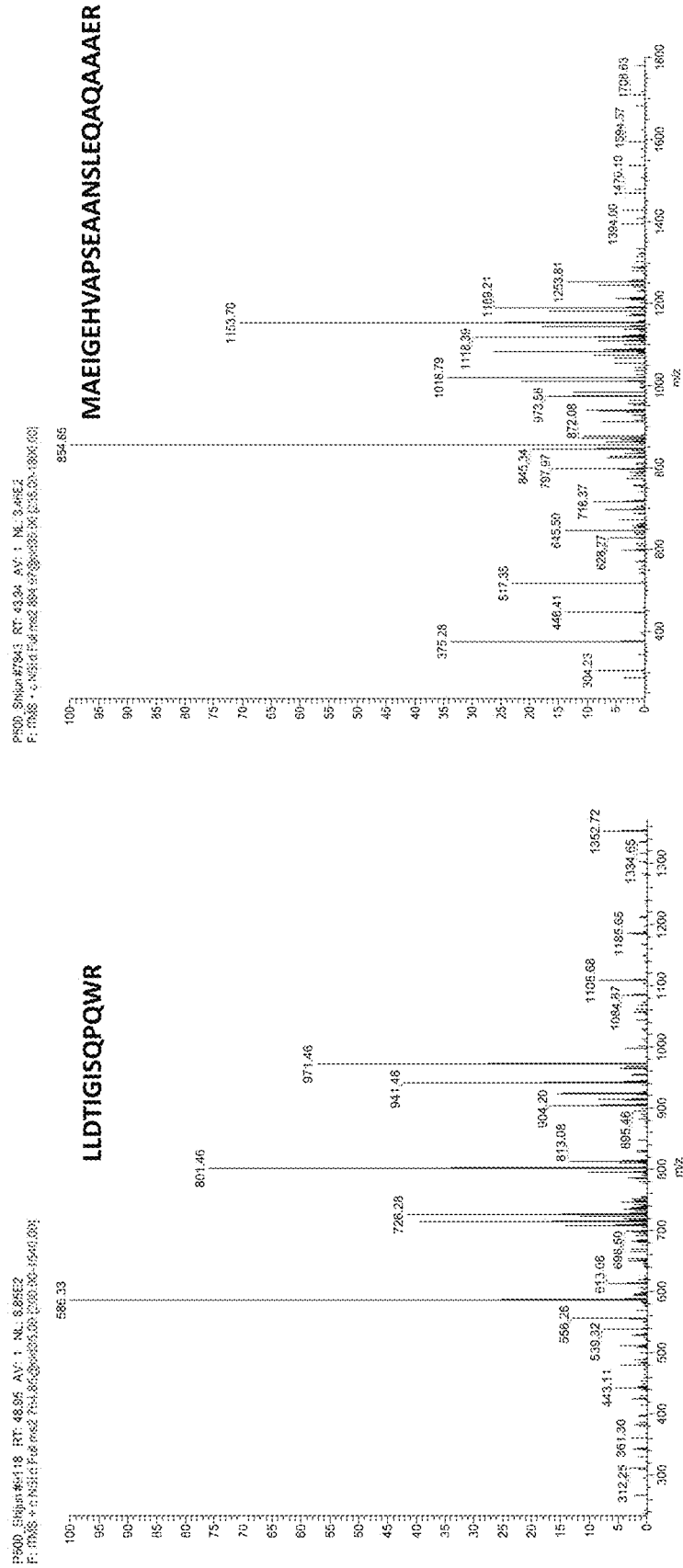
FIG. 6 shows representative fragmentation spectra of CAD peptides (SEQ ID NO: 13-14).

To investigate unknown functions of ARID1A, mass spectrometry was used to analyze immunoaffinity-purified ARID1A complex with the aim to identify novel ARID1A-interacting proteins. First, endogenous ARID1A complex was immunoprecipitated from ARID1A wildtype endometrial cancer cells (KLE)[5]. A resulting Coomassie stained SDS-PAGE gel is shown in FIG. 1A. In addition to known BAF subunit proteins, a ~250 kD protein band was observed and excised for analysis. Following trypsin proteolysis, peptide sequences were determined by liquid chromatography-tandem mass spectrometry (LC-MS/MS) and identified to be Carbamoyl-phosphate synthetase 2, Aspartate transcarbamoylase, and Dihydroorotase (CAD). Fragmentation spectra of CAD peptides (SEQ ID NO: 13-14) are shown in FIG. 6. LC-MS/MS analysis of the immunopurified ARID1A complex from ARID1A wildtype ovarian cancer cells (E52[6]) was performed similar results identifying CAD peptides were obtained.

Figure 1:
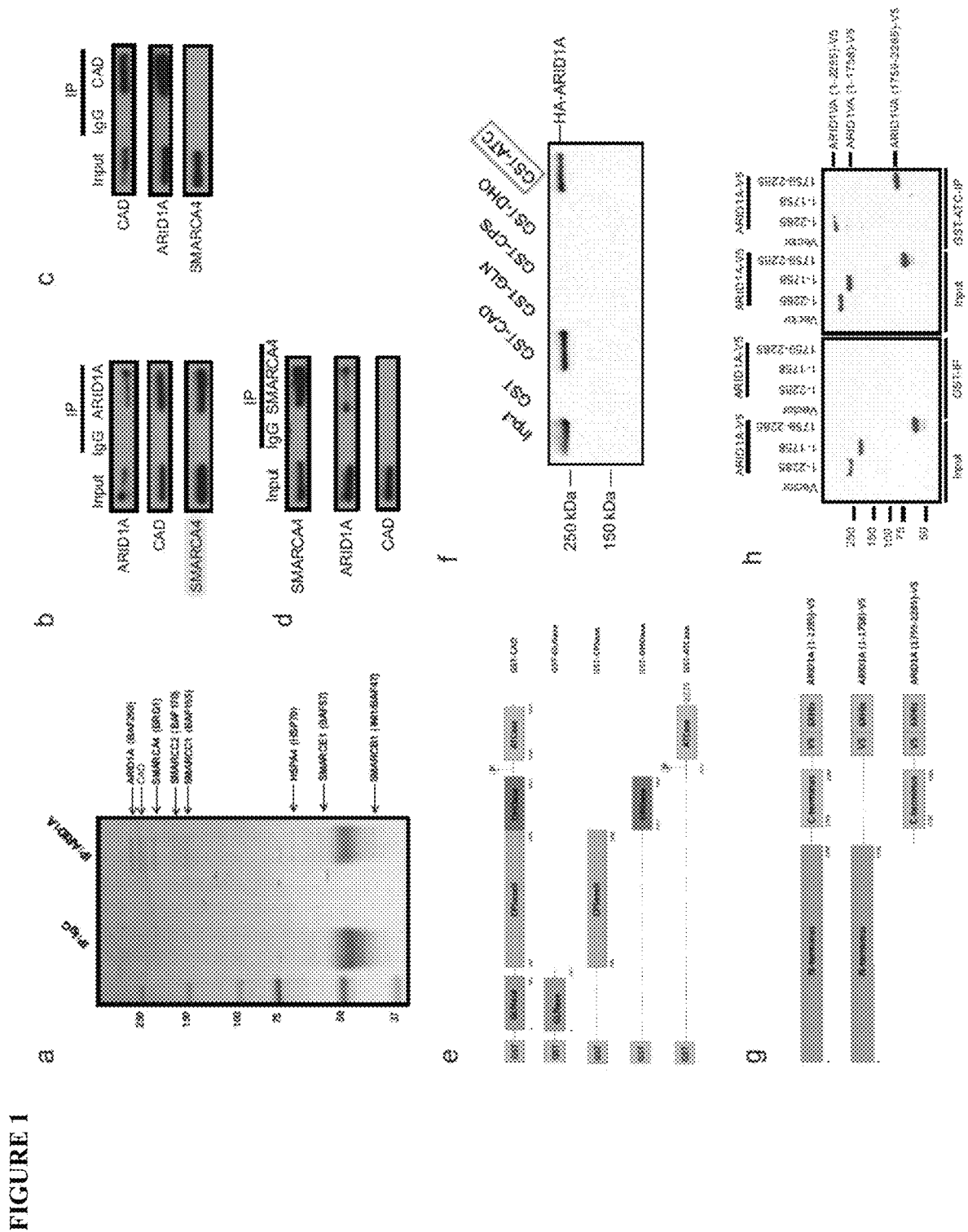
FIGS. 1A-1H show that ARID1A interacts with CAD.

Immunoprecipitation using anti-ARID1A (FIG. 1B) and anti-CAD (FIG. 1C) antibodies followed by immunoblotting confirmed interaction between endogenous ARID1A and CAD in cell lines that express wild-type ARID1A. Co-immunoprecipitation experiments in ARID1A-wildtype ovarian cancer (E52)[5] cells are shown in FIG. 1. Similar results were seen in ARID1A-wildtype endometrial cancer cells (KLE), data not shown. In addition to ARID1A, another core subunit of the BAF complex is SMARCA4

(also known as BRG1)[7]. It was found that SMARCA4 co-immunoprecipitated with ARID1A (FIG. 1B). In contrast, SMARCA4 did not co-immunoprecipitate with CAD, nor did CAD co-immunoprecipitate with SMARCA4, suggesting that the BAF complex itself does not interact with CAD (FIG. 1C, 1D).

Bases of interactions of CAD and ARID1A were further investigated in vitro. Recombinant GST-tagged full-length CAD (SEQ ID NO: 5) and CAD protein fragments, corresponding to protein domains (SEQ ID NO: 6-9) shown in FIG. 1E, were expressed in *Escherichia coli*. In vitro interaction of full-length CAD (SEQ ID NO: 5) with ARID1A was demonstrated by GST pulldown assay (FIG. 1F). By using recombinant GST-tagged CAD fragments (SEQ ID NO: 6-9) as bait, the ARID1A-interacting domain of CAD was localized to the aspartate transcarbamylase (ATCase) domain (FIG. 1F). In a following set of experiments, GST-ATCase (SEQ ID NO: 9) was used as bait, and full-length ARID1A (SEQ ID NO: 10), N-terminus ARID1A (SEQ ID NO: 11), or C-terminus ARID1A (SEQ ID NO: 12) was expressed in HEK293 (FIG. 1G). GST-ATCase (SEQ ID NO: 9) pulled down full-length ARID1A (SEQ ID NO: 10), as expected, and C-terminus ARID1A (SEQ ID NO: 12) but not N-terminus ARID1A (SEQ ID NO: 11) (FIG. 1h). Thus, the CAD-interacting domain of ARID1A was localized at the C-terminus.

Figure 2:
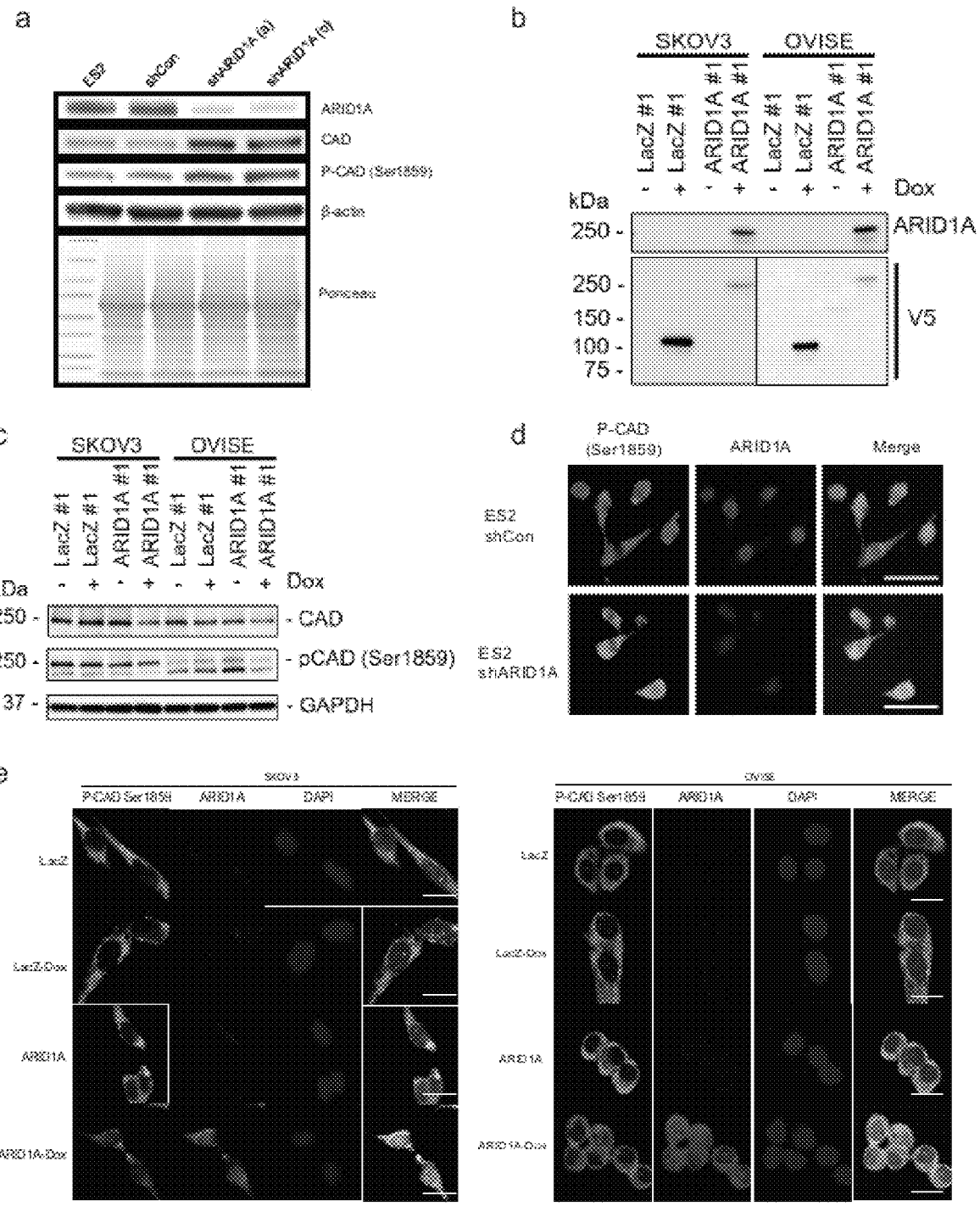
FIGS. 2A-2E show that ARID1A negatively regulates CAD.
Figure 7:
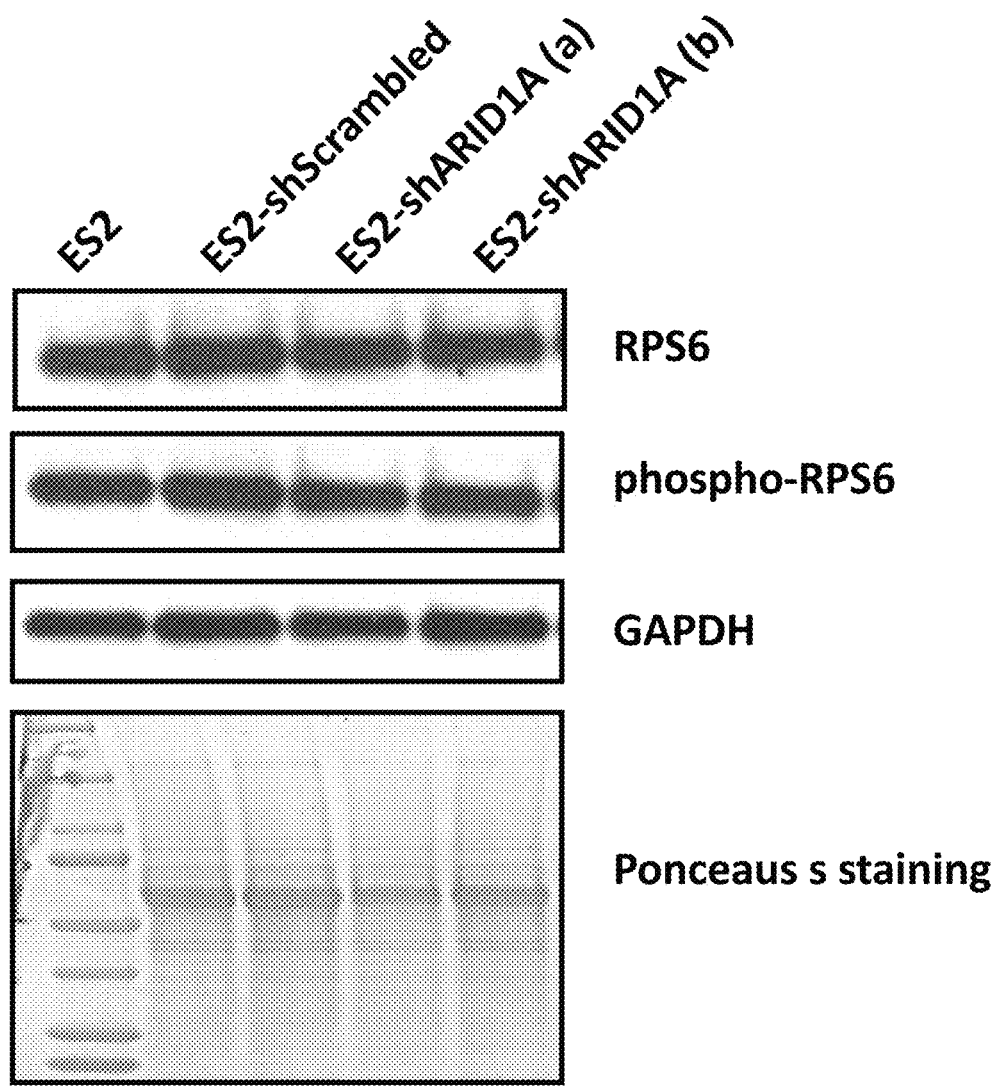
FIG. 7 shows a representative immunoblot demonstrating unchanged RPS6 and phosphorylated RPS6 in ARID1A knockdown cells compared to control cells.

Example 2: Investigations into the Role of ARID1A as a Regulator of CAD Via Protein-Protein Interaction ARID1A as a potential regulator of CAD via protein-protein interaction was investigated. ARID1A mutations in human cancers are typically associated with loss of ARID1A (BAF250A) protein expression due to truncating nonsense or frameshift mutations. To investigate functional consequences of ARID1A mutation and protein deficiency, previously validated short hairpin(sh) RNA vectors (SEQ ID NO: 1-2) provided by I.-M. Shih[8] were used to knockdown ARID1A, and clones stably transfected with the vectors, the clones being called shARID1A(a) and shARID1A(b), were used in further analyses. Knockdown of ARID1A was confirmed by immunoblotting (FIG. 2A). Resulting phenotype was evaluated relative to isogenic cells transfected with a non-targeting scrambled control shRNA (shCon) (SEQ ID NO: 3), and untransfected cells. As shown in FIG. 2A, ARID1A knockdown cells demonstrated increased total CAD levels. CAD activity is controlled via phosphorylation at several key regulatory sites, including serine 1859, phosphorylated by ribosomal protein S6 kinase B1 (RPS6KB1, also known as S6K)[9,10]. Shown in FIG. 2A, serine 1859 phosphorylated CAD protein levels increased following ARID1A knockdown, paralleling an increase in total CAD. ARID1A knockdown does not affect total or phosphorylated levels of the RPS6KB1 canonical substrate, ribosomal protein S6 suggesting that the increased CAD phosphorylation is not due to increased RPS6KB1 activity (FIG. 7). Correlation of ARID1A with CAD was confirmed by immunofluresence observation (FIG. 2D). Similar to observations in ES2 cells, when ARID1A is depleted in ARID1A wild-type KLE endometrial carcinoma cells by shRNA (SEQ ID NO: 1-2), total and phosphorylated CAD levels increased compared with control shRNA transfection (data not shown).

Conversely, the effect of ARID1A restoration on CAD was determined using ARID1A-mutant ovarian cancer cell lines, SKOV3 and OVISE. Both cell lines contained ARID1A mutations. Loss of ARID1A protein expression was confirmed by immunoblotting. To control ARID1A gene expression, a Tet-On tetracycline system was established in SKOV3 and OVISE cell lines. Expression of ARID1A was confirmed by immuboblotting (FIG. 2B). CAD phosphorylation (Serine-1859) and total CAD protein level was increased in ARID1A restoration cells (FIG. 2C). Negative correlation of ARID1A with CAD was confirmed by immunofluresence observation (FIG. 2E).

Figure 8:
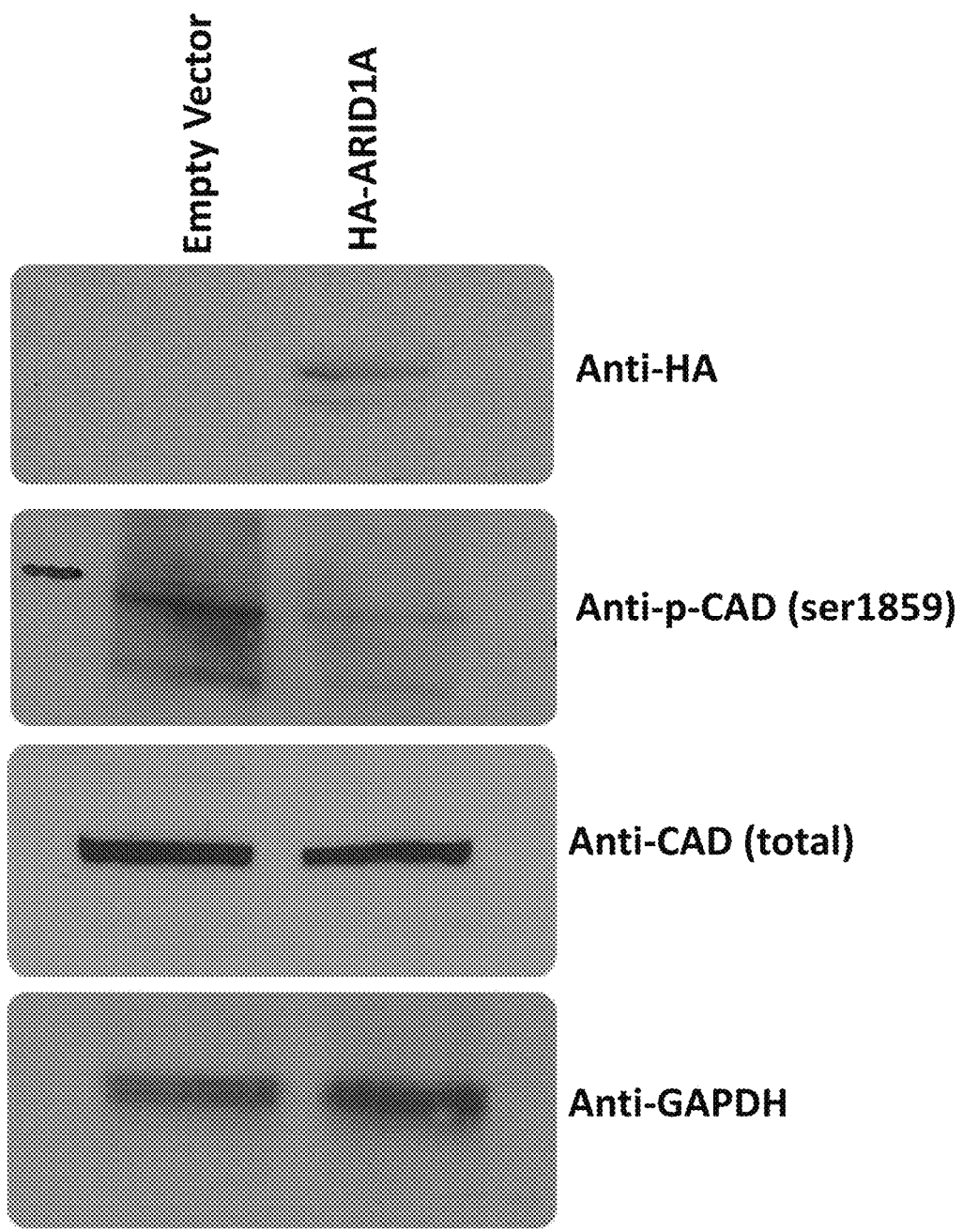
FIG. 8 is an immunoblot showing restoration of ARID1A expression in ARID1A-mutant cell line HEC-1-A leads to a reduction in phosphorylated and total CAD.

A similar result was confirmed in HEC-1-A, an ARID1A-mutant endometrial cancer cell line. This cell line has two heterozygous truncating mutations at p.Q1835* and p.Q2115*[11]. Loss of ARID1A protein expression was confirmed by immunoblotting. Following transfection with full-length ARID1A, compared with control empty vector, CAD phosphorylation (Serine-1859) and total CAD protein level was reduced (Suppl. FIG. 8). Cumulatively, these findings indicate that wildtype ARID1A functions as a negative regulator of CAD, wherein ARID1A deficiency results in an increase in total and phosphorylated CAD.

Example 3: Investigations into Whether ARID1A Deficiency Affects De Novo Pyrimidine Synthesis ATCase enzymatic activity of CAD catalyzes the reaction of carbamoyl phosphate and aspartate to N-carbamoyl aspartate, and is the first committed step in de novo pyrimidine biosynthesis (FIG. 3A). To quantify a rate of de novo pyrimidine synthesis, incorporation of $^{14}C$-radiolabelled aspartate into RNA and DNA was measured. RNA and DNA synthesized via the pyrimidine salvage pathway do not incorporate $^{14}C$-radiolabelled aspartate, imparting specificity for measuring de novo pyrimidine synthesis. ARID1A knockdown resulted in increased $^{14}C$ incorporation into RNA, indicating increased de novo pyrimidine synthesis (FIG. 3B). Increased $^{14}C$ incorporation was similarly observed in DNA (data not shown). Given that de novo pyrimidine biosynthesis affects further pathways to uridine metabolites synthesis, UTP level in both ARID1A knockdown and restoration cell lines were examined. It was observed that UTP level was increased in ARID1A knockdown cells (FIG. 3C). Doxycline induced ARID1A and increased the abundance of UTP in both SKOV3 and OVISE cells (FIG. 3D). Together, these data indicate that a negative correlation of ARID1A and CAD levels corresponds to ARID1A negatively regulating de novo pyrimidine biosynthesis.

Example 4: Evaluating the Effect of DHODH Inhibitors on ARID1A Deficient Cells Elevated rates of de novo pyrimidine synthesis in ARID1A deficient cells may alter sensitivity to a pyrimidine synthesis blockade. An effect of inhibitors of dihydroorotate dehydrogenase (DHODH), the enzyme immediately downstream of CAD that catalyzes the conversion of dihydroorotate to orotate, was evaluated. As shown in FIG. 4A, ARID1A knockdown cells were significantly more sensitive to DHODH inhibition using teriflunomide. Similar results were observed using leflunomide (data not shown), which is a DHODH inhibitor. Conversely, an effect of ARID1A restoration on teriflunomide was determined using ARID1A-mutant ovarian cancer cell lines, SKOV3 and OVISE. ARID1A restoration cells were more resistant to teriflunomide and showed significantly higher IC50 in both ARID1A restoration cells (FIGS. 4B and 4C).

Figure 9:
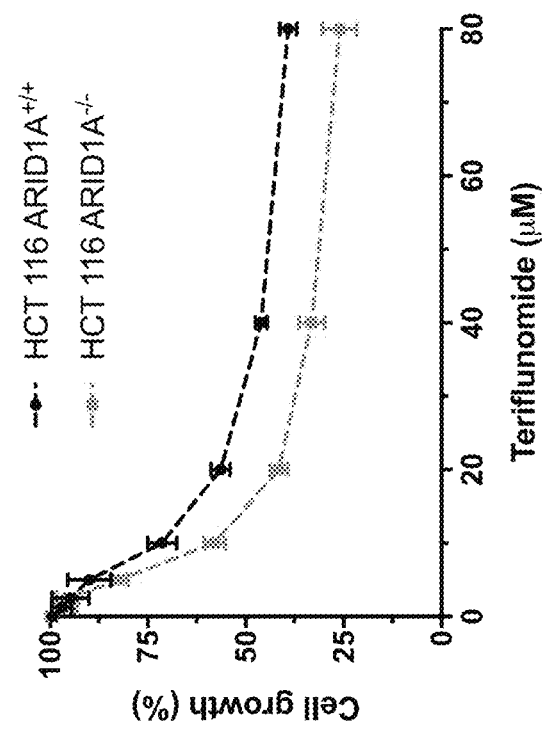
FIG. 9 shows that HCT116 ARID1A knockout cells are more sensitive to teriflunomide compared to control cells (HCT116 ARID1A wild-type).
Figure 9:
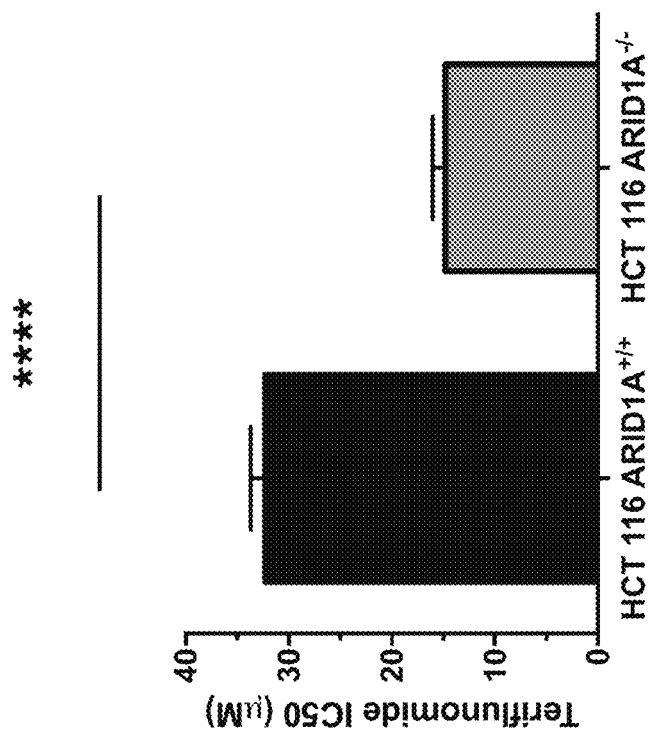

A novel finding of vulnerability to a de novo pyrimidine synthesis blockade was confirmed by several complementary approaches. The effect of DHODH inhibition in HCT116 colorectal carcinoma cells with homozygous knockout of ARID1A by knock-in of premature stop codons (Q456*/Q456*) was evaluated. Compared to wildtype HCT116 cells, ARID1A (Q456*/Q456*) HCT116 cells were significantly hypersensitive to DHODH inhibitors (FIG. 9).

Figure 10:
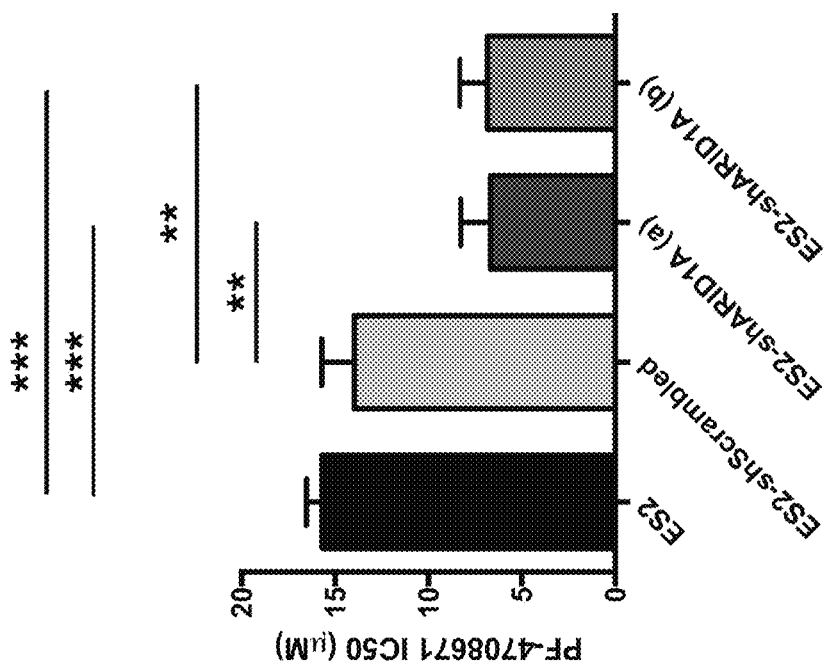
FIGS. 10A and 10B show that ES2 knockdown cells are more sensitive to the S6 kinase inhibitor PF-4708671.
Figure 10:
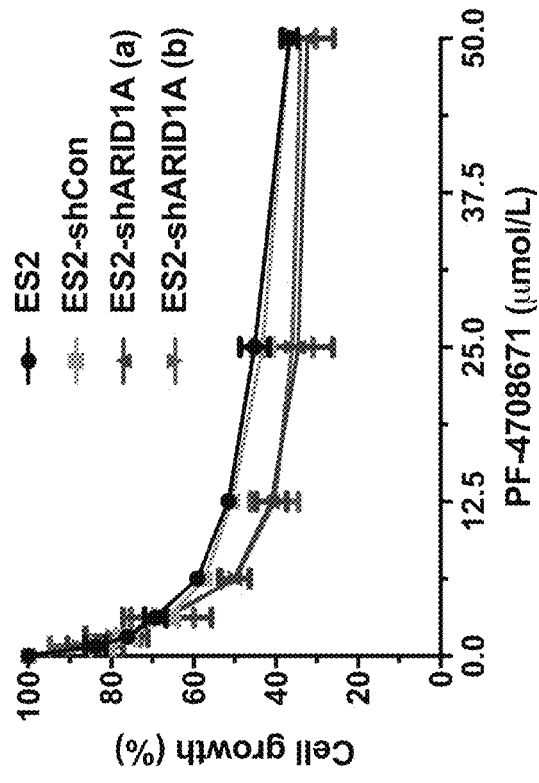

Whether ARID1A deficiency is associated with hypersensitivity to S6K1 inhibition was also evaluated, since S6K1 is an upstream activator of CAD via phosphorylation at Serine-1859. ES2-shARID1A cells were significantly hypersensitive to the S6K1 inhibitor, PF-4708671, compared to ES2-shCon cells or untransfected (ARID1A-wildtype) ES2 cells (FIG. 10).

Figure 11:
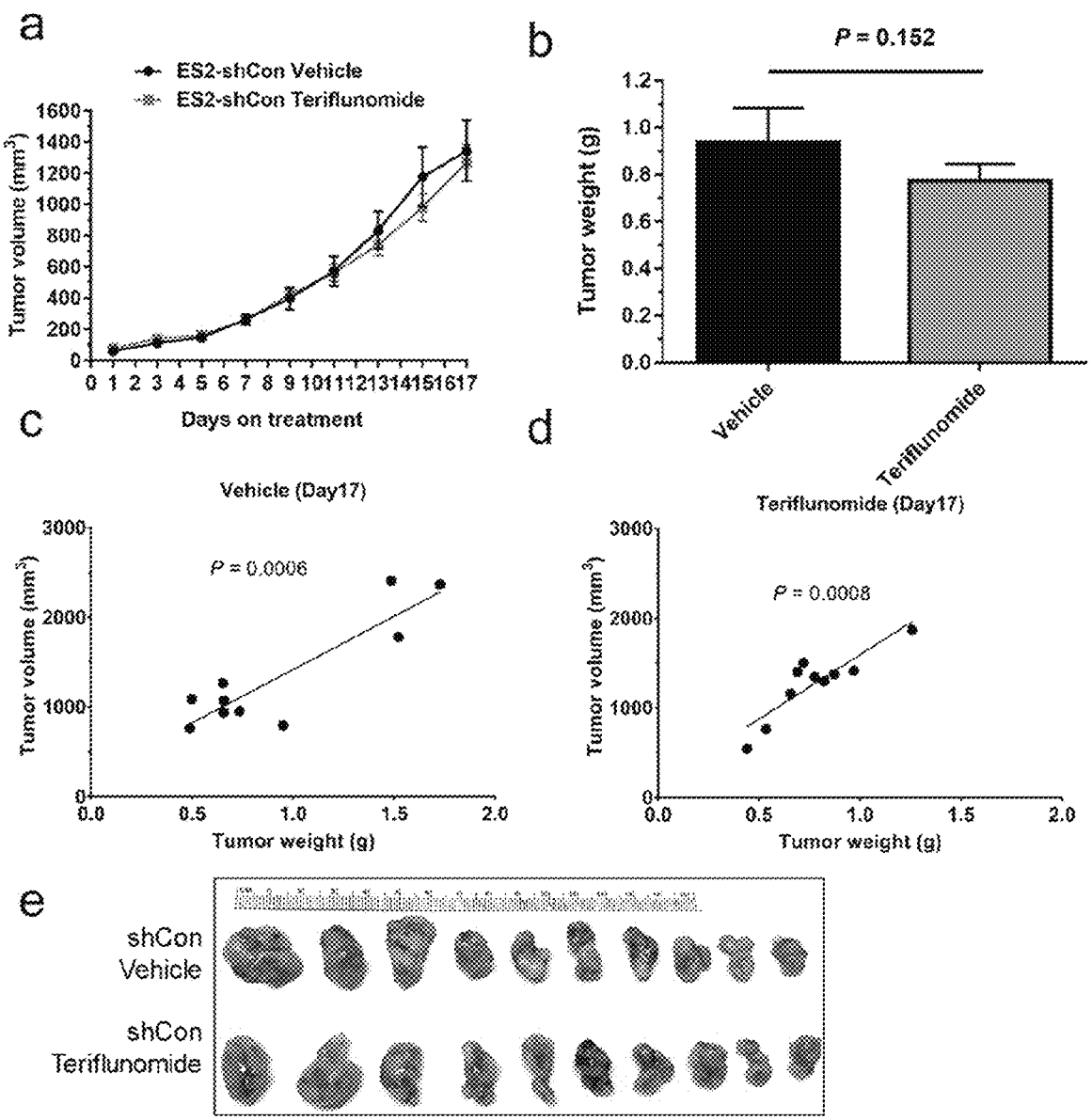
FIGS. 11A-11E show the effect of teriflunomide in an ES2-shCon tumor xenograft model. The xenograft model was generated by subcutaneously injecting ES2-shCon cells in Matrigel (1:1) into athymic nude mice. Teriflunomide (4 mg/kg) or vehicle was intraperitoneally injected every other day. Tumor size was recorded on the same day.

In vivo validation is an important step in translation of scientific findings to clinical application. Therefore, the therapeutic efficacy of DHODH inhibition was evaluated using mice bearing tumor xenografts that recapitulate human clear cell ovarian cancer (FIG. 4D). Confirmation of ARID1A knockdown in vivo was done by immunoblotting of representative excised tumor xenografts (FIG. 4H). ARID1A-deficient tumor xenografts exhibited higher total and phosphorylated CAD level (FIGS. 4H and 4I). Xenograft-bearing mice were randomized to treatment with teriflunomide, or vehicle alone. Teriflunomide was administered intraperitoneally at a well-tolerated dosing regimen of 4 mg/kg every other day, corresponding to a human equivalent dose of 0.32 mg/kg (i.e., 19.2 mg for a 60 kg human). This dose level is ~30% lower than the FDA-approved dose level of 14 mg daily for the treatment of multiple sclerosis in patients[12]. There was no significant weight loss or toxicity in mice in treatment or vehicle control groups. As shown in FIG. 4D, FIG. 4E, and FIG. 11, teriflunomide selectively suppressed tumor growth in ARID1A-deficient tumor xenografts.

Representative formalin-fixed paraffin embedded (FFPE) tissue sections were prepared from twelve tumor xenografts excised at experiment termination. Shown in FIG. 4G, hematoxylin and eosin stained sections showed diffuse proliferation of high grade epithelioid to focally spindle cells with marked cytological atypia including marked pleomorphism, high nuclear to cytoplasmic ratio, prominent nucleoli and brisk mitotic activity including atypical mitotic features. Similar cellular morphology was seen in shARID1A and shCon xenografts, and marked areas of tumor cell necrosis was observed. Cellular necrosis was quantified as % cross-sectional area of each bisected tumor xenograft. Mean cellular necrosis was similar in untreated shARID1A and shCon xenografts, but significantly higher in a teriflunomide-treated shARID1A xenograft group compared to teriflunomide-treated shCon xenografts (FIG. 4F). Thus, single agent teriflunomide treatment effectively suppressed growth of ARID1A-deficient xenografts and this growth suppression was associated with increased tumor cell necrosis, as observed in xenografts excised following six doses of teriflunomide. The effect of teriflunomide in ARID1A-deficient SKOV3 tumor xenograft models (FIG. 4I) was also evaluated. Teriflunomide significantly improved the animal survival compared to the vehicle treatment group.

Example 5: Combination Treatments

Teriflunomide treatment showed a robust increase in phosphorylation of CHK1 on serine 345 in ES2-shARID1A cells compared with the ES2-shCon group (FIG. 5G). This result indicated that nucleotide depletion by DHODH inhibitors induced DNA damage in ARID1A-deficient cells and triggered protective downstream signaling pathways that involve CHK1 kinase activation. Thus, a hypothis was proposed that treatment of cells with ATR inhibitors could potentiate a cytotoxic effect of DHODH inhibition.

Figure 5:
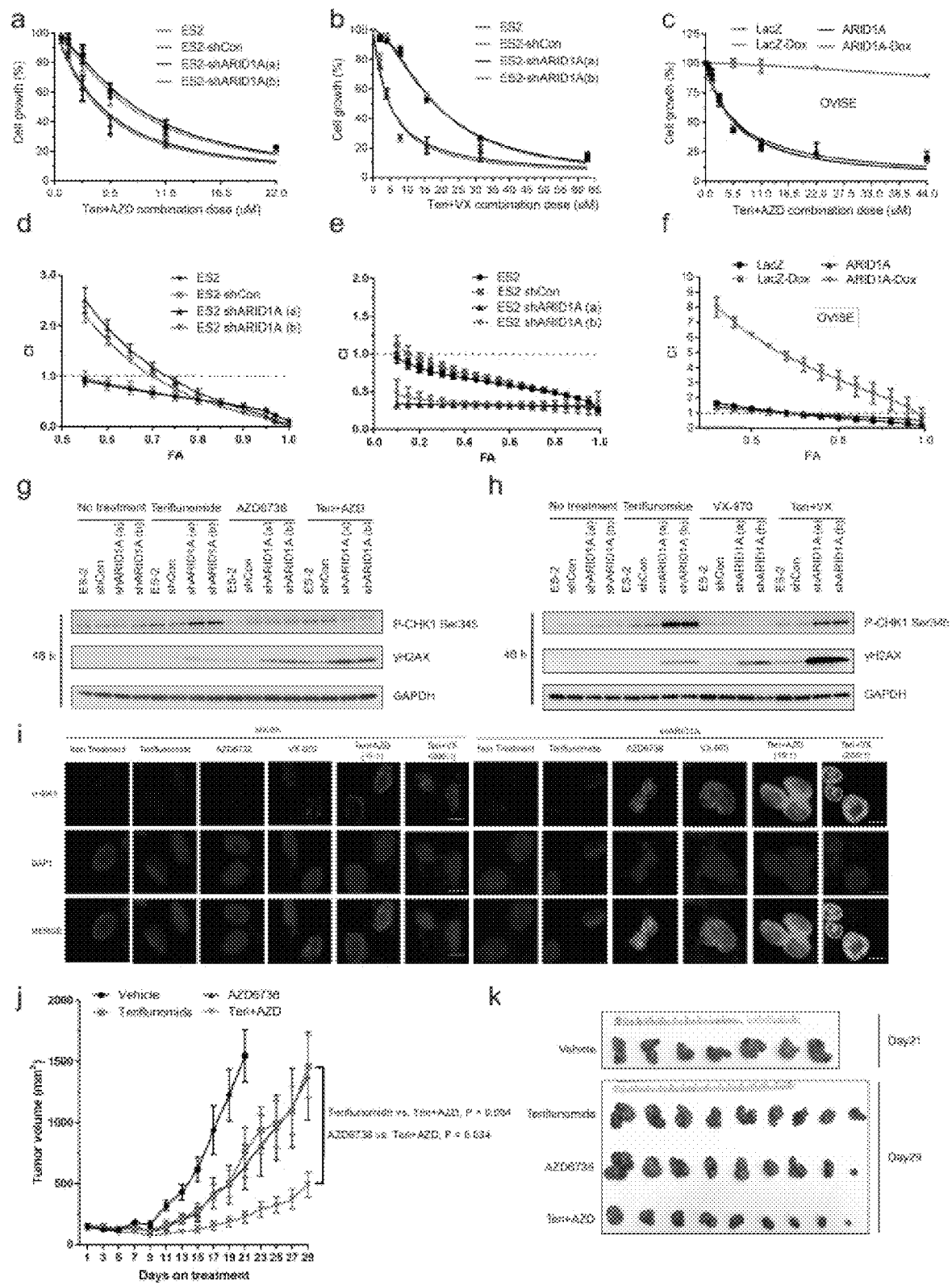
FIGS. 5A-5K show that combination treatment with DHODH inhibitor (DHODHi) and ATR inhibitor (ATRi) is synergistic and efficacious.
Figure 12:
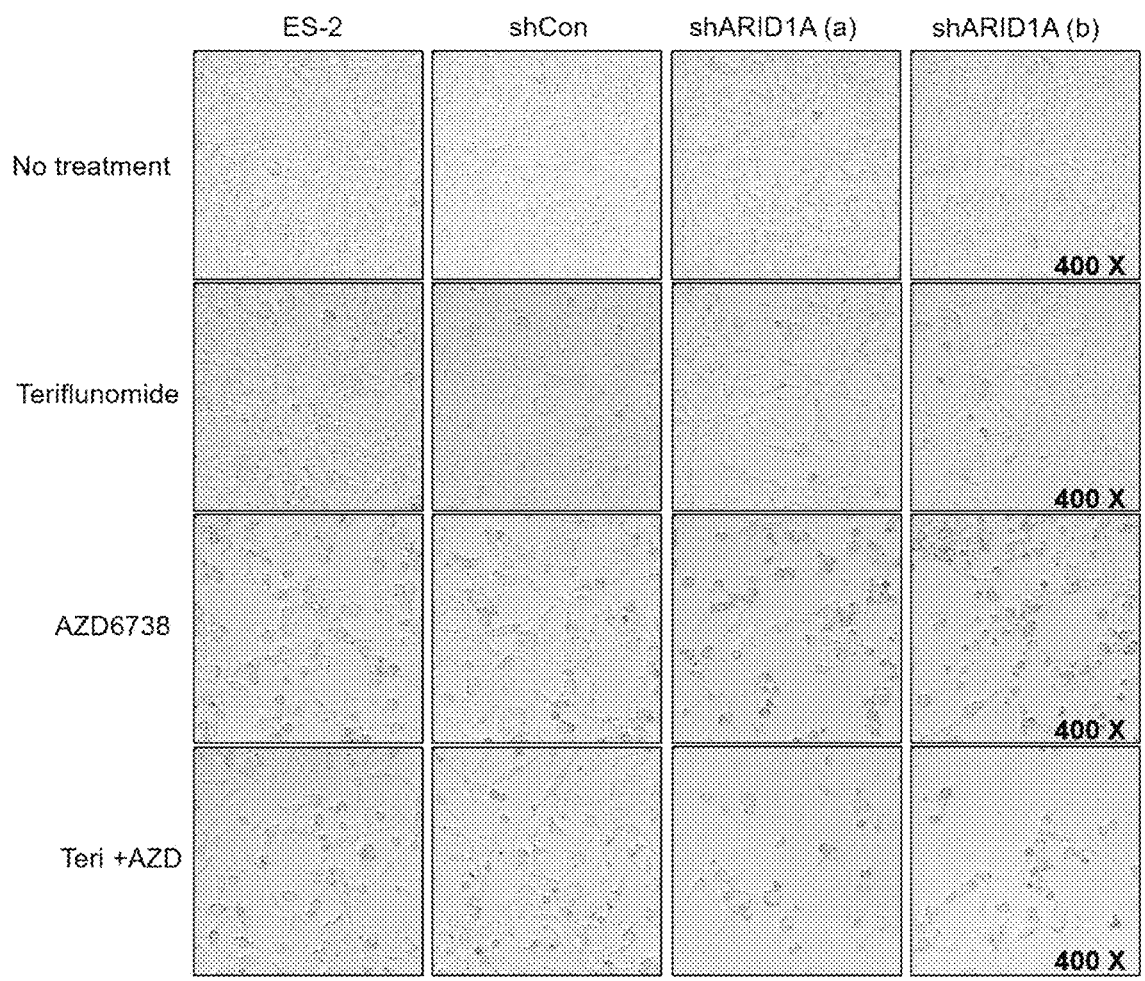
FIG. 12 shows that cell growth arrest in ARID1A-knockdown cells (shARID1A) was greatest in a Teri-AZD combination treatment group.

Shown in FIG. 5, combination treatment with DHODH and ATR inhibitors induced some degree of synergy in both ARID1A wildtype and knockdown cells (FIG. 12, and Tables 1 and 2 below). While synergy is observed in both ARID1A wildtype and knockdown cells, synergism is most pronounced/most potently observed in ARID1A knockdown cells at drug concentrations corresponding to an effective therapeutic dose (i.e. ED75, ED90). In other words, more potent synergism (indicated by lower CI values) are observed at therapeutically effective drug concentrations of the inhibitors.

TABLE 1

Analysis of a combination of AZD6738 with FDA-approved teriflunomide in ES2 cells.

| Cell, Plasmid and Drug | CI Values at | | | Dm (μM) | r | $CI_{wt}$ |
| --- | --- | --- | --- | --- | --- | --- |
| | ED50 | ED75 | ED90 | | | |
| ES2-Teriflunomide | N/A | N/A | N/A | 26.36 ± 2.18 | 0.98 ± 0.009 | N/A |
| SCR-Teriflunomide | N/A | N/A | N/A | 28.15 ± 1.59 | 0.98 ± 0.003 | N/A |
| shARID1A (a)-Teriflunomide | N/A | N/A | N/A | 17.86 ± 1.32*** | 0.91 ± 0.052 | N/A |
| shARID1A (b)-Teriflunomide | N/A | N/A | N/A | 16.76 ± 0.92*** | 0.99 ± 0.003 | N/A |
| ES2-AZD6738 | N/A | N/A | N/A | 1.23 ± 0.16 | 0.92 ± 0.020 | N/A |
| SCR-AZD6738 | N/A | N/A | N/A | 1.18 ± 0.17 | 0.92 ± 0.026 | N/A |
| shARID1A (a)-AZD6738 | N/A | N/A | N/A | 0.20 ± 0.01*** | 0.88 ± 0.022 | N/A |
| shARID1A (b)-AZD6738 | N/A | N/A | N/A | 0.24 ± 0.03*** | 0.85 ± 0.016 | N/A |
| ES2-Combo (10:1 molar ratio) | 0.91 ± 0.099 | 0.53 ± 0.007 | 0.32 ± 0.028 | 7.57 ± 0.50 | 0.98 ± 0.002 | 0.49 ± 0.005 |
| SCR-Combo (10:1 molar ratio) | 0.95 ± 0.152 | 0.54 ± 0.091 | 0.31 ± 0.065 | 7.85 ± 1.05 | 0.99 ± 0.010 | 0.49 ± 0.083 |
| shARID1A (a)-Combo (10:1 molar ratio) | 2.51 ± 0.251 | 0.68 ± 0.076 | 0.22 ± 0.030 | 4.57 ± 0.18** | 0.98 ± 0.006 | 0.76 ± 0.049 |
| shARID1A (b)-Combo (10:1 molar ratio) | 2.21 ± 0.154 | 0.55 ± 0.054 | 0.17 ± 0.050 | 4.62 ± 0.19** | 0.98 ± 0.004 | 0.64 ± 0.020 |

In Table 1 CI values were determined for the indicated two-drug combinations at 50% (ED50), 75% (ED75), and 90% (ED90) inhibition of cell proliferation using a CalcuSyn program. Drug concentrations corresponding to a median effect (Dm) are shown for each treatment; teriflunomide concentration is shown for combination (Combo) treatment at a 10:1 fixed molar ratio of two drugs, teriflunomide and AZD6738. Weighted CI ($CI_{wt}$), which is calculated using the formula $CI_{wt}=(ED50+2ED75+3ED90)/6$, showed an overall synergistic interaction of the two drugs; a $CI_{wt}<0.8$, =0.8 to 1.2, and >1.2 indicates synergism, an additive effect, and antagonism, respectively. Datasets from at least three independent experiments were combined, and each table cell contains the mean value±SD. SCR, ES2-shScrambled. N/A, not applicable. Statistical analysis was carried out by one-way ANOVA with Bonferroni's post-hoc test, and differences were considered significant at $P<0.01$ and *$P<0.001$ as compared to the ES2 parental group with the same drug treatment.

TABLE 2

Analysis of combination of VX-970 with teriflunomide in ES2 cells.

| Cell, Plasmid, and Drug | CI Values at | | | Dm | R | $CI_{wt}$ |
|---|---|---|---|---|---|---|
| | ED50 | ED75 | ED90 | | | |
| ES2-Teri (µM) | N/A | N/A | N/A | 29.09 ± 0.54 | 0.97 ± 0.004 | N/A |
| SCR-Teri (µM) | N/A | N/A | N/A | 26.67 ± 1.26 | 0.97 ± 0.002 | N/A |
| shARID1A (a)-Teri (µM) | N/A | N/A | N/A | 15.57 ± 1.79*** | 0.99 ± 0.005 | N/A |
| shARID1A (b)-Teri (µM) | N/A | N/A | N/A | 15.46 ± 3.11*** | 0.98 ± 0.011 | N/A |
| ES2-VX970 (nM) | N/A | N/A | N/A | 165.22 ± 3.84 | 0.95 ± 0.004 | N/A |
| SCR-VX970 (nM) | N/A | N/A | N/A | 169.55 ± 9.24 | 0.96 ± 0.008 | N/A |
| shARID1A (a)-VX970 (nM) | N/A | N/A | N/A | 54.33 ± 1.31*** | 0.98 ± 0.005 | N/A |
| shARID1A (b)-VX970 (nM) | N/A | N/A | N/A | 63.32 ± 10.37*** | 0.98 ± 0.003 | N/A |
| ES2-Combo (200:1) | 0.63 ± 0.053 | 0.51 ± 0.015 | 0.42 ± 0.015 | 18.26 ± 1.72 | 0.98 ± 0.002 | 0.48 ± 0.026 |
| SCR-Combo (200:1) | 0.68 ± 0.078 | 0.53 ± 0.060 | 0.41 ± 0.060 | 18.03 ± 2.31 | 0.97 ± 0.010 | 0.50 ± 0.058 |
| shARID1A (a)-Combo (200:1) | 0.32 ± 0.020 | 0.30 ± 0.009 | 0.30 ± 0.009 | 4.92 ± 0.75 | 0.95 ± 0.006 | 0.31 ± 0.009 |
| shARID1A (b)-Combo (200:1) | 0.33 ± 0.023 | 0.31 ± 0.101 | 0.31 ± 0.101 | 5.08 ± 0.88*** | 0.93 ± 0.004 | 0.31 ± 0.119 |

In Table 2 CI values were determined for indicated two-drug combinations at 50% (ED50), 75% (ED75), and 90% (ED90) inhibition of ES2 cell proliferation using a CalcuSyn program. Drug concentrations (in µM for teriflunomide, in nM for VX980) corresponding to median effect (Dm) are shown for each treatment; teriflunomide concentration is shown for combination (Combo) treatment at a 200:1 fixed molar ratio of the two drugs, teriflunomide and VX-970. $CI_{wt}$ showed an overall synergistic interaction of the two drugs. $CI_{wt}<0.8$, =0.8 to 1.2, and >1.2 indicates synergism, an additive effect, and antagonism, respectively. $CI_{wt}$ value was calculated using the formula: $CI_{wt}=(ED50+2ED75+3ED90)/6$. Datasets from at least three independent experiments were combined, and each table cell contains the mean value±SD. Teri, teriflunomide. SCR, ES2-sh-Scrambled. N/A, not applicable. Statistical analysis was carried out by one-way ANOVA with Bonferroni's post-hoc test, and differences were considered significant at ***P<0.001 as compared to the ES2 parental group with the same drug treatment.

Conversely to the case for knockdown cells, ARID1A restoration cells showed relative drug resistance and an antagonistic interaction to combination treatment (FIG. 5C, 5F and Table 3).

In Table 3, CI values were determined for indicated two-drug combinations at 50% (ED50), 75% (ED75), and 90% (ED90) inhibition of OVISE cell proliferation using the CalcuSyn program. $CI_{wt}$ showed the overall synergic effect of combination tests. $CI_{wt}<0.8$, =0.8 to 1.2, and >1.2 indicates synergism, an additive effect, and antagonism, respectively. A $CI_{wt}$ value was assigned as follows: (ED50+2ED75+3ED90)/6. Datasets from at least three independent experiments were combined, and means±SD were calculated for each combination. Teri, teriflunomide. N/A, not applicable. Statistical analysis was carried out by one-way ANOVA with Bonferroni's post-hoc test, and differences were considered significant at ***P<0.001 as compared to the ARID1A restoration group induced by doxycycline with the same drug treatment.

A combination effect of DHODH and ATR inhibitors in A2780 cells was also evaluated (Table 4), JH005 (Table 5), and HEC-1A cells (Table 6), and observed a synergistic interaction in these cell lines.

TABLE 3

Analysis of a combination of AZD6738 with FDA-approved teriflunomide in ARID1A-restoration OVISE cells.

| Plasmid and Drug | CI Values at | | | Dm | r | $CI_{wt}$ |
|---|---|---|---|---|---|---|
| | ED50 | ED75 | ED90 | | | |
| LacZ-Teri (µM) | N/A | N/A | N/A | 18.24 ± 1.19*** | 0.98 ± 0.025 | N/A |
| LacZ Dox-Teri (µM) | N/A | N/A | N/A | 19.30 ± 1.24*** | 0.99 ± 0.008 | N/A |
| ARID1A-Teri (µM) | N/A | N/A | N/A | 19.08 ± 1.07*** | 0.99 ± 0.001 | N/A |
| ARID1A Dox-Teri (µM) | N/A | N/A | N/A | 109.48 ± 3.18 | 0.98 ± 0.011 | N/A |
| LacZ-AZD6738 (µM) | N/A | N/A | N/A | 0.70 ± 0.03*** | 0.95 ± 0.030 | N/A |
| LacZ Dox-AZD6738 (µM) | N/A | N/A | N/A | 0.67 ± 0.11*** | 0.96 ± 0.021 | N/A |
| ARID1A-AZD6738 (µM) | N/A | N/A | N/A | 0.77 ± 0.16*** | 0.98 ± 0.012 | N/A |
| ARID1A Dox-AZD6738 (µM) | N/A | N/A | N/A | 6.99 ± 0.34 | 0.98 ± 0.014 | N/A |
| LacZ-Combo (10:1) | 1.30 ± 0.160 | 0.70 ± 0.048 | 0.40 ± 0.047 | 6.55 ± 1.03*** | 0.94 ± 0.013 | 0.65 ± 0.047 |
| LacZ Dox-Combo (10:1) | 1.16 ± 0.220 | 0.64 ± 0.030 | 0.39 ± 0.035 | 5.70 ± 0.81*** | 0.96 ± 0.002 | 0.60 ± 0.035 |
| ARID1A-Combo (10:1) | 1.18 ± 0.088 | 0.84 ± 0.182 | 0.65 ± 0.196 | 6.41 ± 0.48*** | 0.95 ± 0.013 | 0.80 ± 0.196 |
| ARID1A Dox-Combo (10:1) | 6.15 ± 0.254 | 3.21 ± 1.026 | 1.86 ± 0.934 | 262.45 ± 20.20 | 0.99 ± 0.004 | 3.02 ± 0.934 |

TABLE 4

Analysis of the combination of AZD6738 with teriflunomide in A2780 cells.

| Drug | CI Values at | | | Dm | m | R | $CI_{wt}$ |
| --- | --- | --- | --- | --- | --- | --- | --- |
| | ED50 | ED75 | ED90 | | | | |
| Teriflunomide | N/A | N/A | N/A | 18.91 ± 1.39 | 0.82 ± 0.13 | 0.99 ± 0.001 | N/A |
| AZD6738 | N/A | N/A | N/A | 5.54 ± 1.06 | 1.19 ± 0.18 | 0.99 ± 0.003 | N/A |
| Combo (10:1) | 0.74 ± 0.03 | 0.47 ± 0.05 | 0.31 ± 0.08 | 10.40 ± 0.82 | 1.48 ± 0.35 | 0.99 ± 0.003 | 0.44 ± 0.06 |

In Table 4, CI values were determined for indicated two-drug combinations at 50% (ED50), 75% (ED75), and 90% (ED90) inhibition of A2780 cell proliferation using a CalcuSyn program. Drug concentrations corresponding to a median effect (Dm) are shown for each treatment; teriflunomide concentration is shown for a combination (Combo) treatment at a 10:1 fixed molar ratio of two drugs, teriflunomide and AZD6738. $CI_{wt}$ showed the overall synergistic interaction of the two drugs. $CI_{wt}$<0.8, =0.8 to 1.2, and >1.2 indicate synergism, an additive effect, and antagonism, respectively. A $CI_{wt}$ value was calculated using the formula: $CI_{wt}=(ED50+2ED75+3ED90)/6$. Datasets from at least three independent experiments were combined, and each table cell contains the mean value±SD.

TABLE 5

Analysis of the combination of AZD6738 with teriflunomide in JHOC-5 cells.

| Drug | CI Values at | | | Dm | m | R | $CI_{wt}$ |
| --- | --- | --- | --- | --- | --- | --- | --- |
| | ED50 | ED75 | ED90 | | | | |
| Teriflunomide | N/A | N/A | N/A | 25.20 ± 1.85 | 1.10 ± 0.03 | 0.98 ± 0.006 | N/A |
| AZD6738 | N/A | N/A | N/A | 2.91 ± 0.76 | 1.20 ± 0.12 | 0.99 ± 0.012 | N/A |
| Combo (10:1) | 1.03 ± 0.03 | 0.82 ± 0.05 | 0.66 ± 0.09 | 13.64 ± 1.42 | 1.52 ± 0.22 | 0.99 ± 0.008 | 0.78 ± 0.06 |

In Table 5, CI values were determined for indicated two-drug combinations at 50% (ED50), 75% (ED75), and 90% (ED90) inhibition of JHOC-5 cell proliferation using a CalcuSyn program. The drug concentrations corresponding to a median effect (Dm) are shown for each treatment; teriflunomide concentration is shown for combination (Combo) treatment at a 10:1 fixed molar ratio of two drugs, teriflunomide and AZD6738. $CI_{wt}$ showed the overall synergistic interaction of the two drugs. $CI_{wt}$<0.8, =0.8 to 1.2, and >1.2 indicates synergism, an additive effect, and antagonism, respectively. A $CI_{wt}$ value was calculated using the formula: $CI_{wt}=(ED50+2ED75+3ED90)/6$. Datasets from at least three independent experiments were combined, and each table cell contains the mean value±SD.

TABLE 6

Analysis of combination of AZD6738 with teriflunomide in HEC-1A cells.

| Drug | CI Values at | | | Dm | m | R | $CI_{wt}$ |
| --- | --- | --- | --- | --- | --- | --- | --- |
| | ED50 | ED75 | ED90 | | | | |
| Teriflunomide | N/A | N/A | N/A | 50.49 ± 4.99 | 0.85 ± 0.26 | 0.99 ± 0.005 | N/A |
| AZD6738 | N/A | N/A | N/A | 4.47 ± 0.45 | 1.25 ± 0.20 | 0.99 ± 0.003 | N/A |
| Combo (10:1) | 0.81 ± 0.10 | 0.67 ± 0.24 | 0.61 ± 0.30 | 19.06 ± 0.61 | 1.36 ± 0.38 | 0.99 ± 0.004 | 0.66 ± 0.25 |

In Table 6, CI values were determined for indicated two-drug combinations at 50% (ED50), 75% (ED75), and 90% (ED90) inhibition of HEC-1A cell proliferation using a CalcuSyn program. The drug concentrations corresponding to a median effect (Dm) are shown for each treatment; teriflunomide concentration is shown for combination (Combo) treatment at a 10:1 fixed molar ratio of two drugs, teriflunomide and AZD6738. The $CI_{wt}$ showed the overall synergistic interaction of the two drugs. $CI_{wt}$<0.8, =0.8 to 1.2, and >1.2 indicates synergism, an additive effect, and antagonism, respectively. A $CI_{wt}$ value was calculated using the formula: $CI_{wt}=(ED50+2ED75+3ED90)/6$. Datasets from at least three independent experiments were combined, and each table cell contains the mean value±SD.

Figure 13:
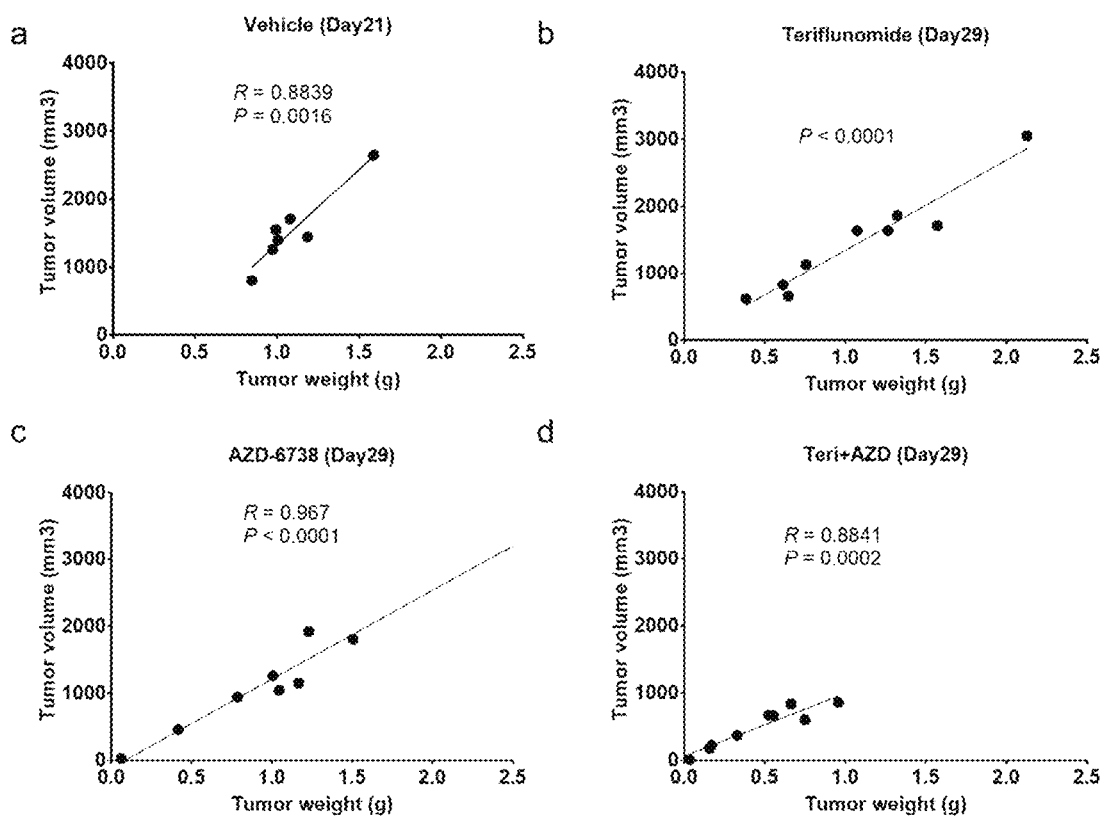
FIGS. 13A-13D show that there is a strong correlation of tumor weight with tumor volume in each xenograft treatment group.
Figure 14:
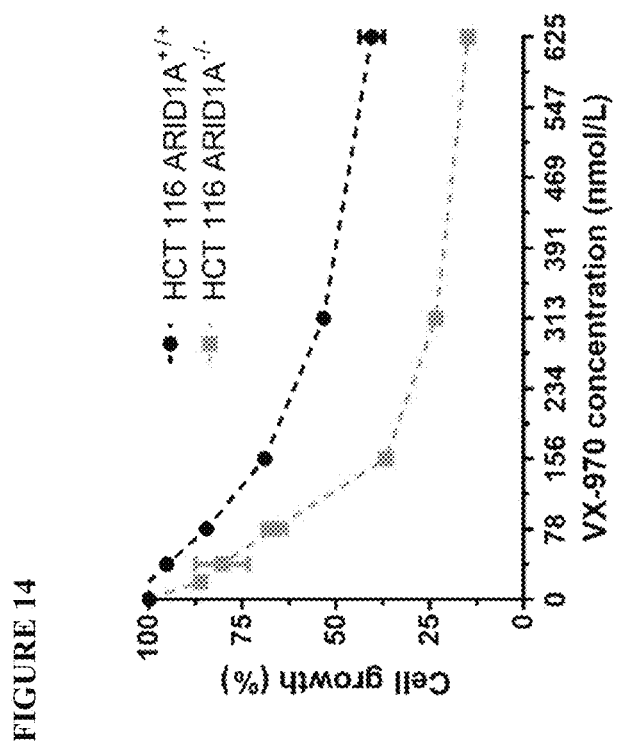
FIG. 14 shows that ARID1A-knockout HCT116 cells were more sensitive to VX-970 compared to control cells.

Combination treatments resulted in DNA damage. ARID1A knockdown cells showed increased gamma-H2AX protein levels in single drugs treatment groups, with highest in combination treatment groups (FIG. 5G-5I). Combining teriflunomide with AZD6738 significantly arrested ES2-tumor volume and progression in xenograft models (FIG. 5J, 5K and FIG. 13).

Example 6: Evaluating ARID1A-Knockout HCT116 Cell Sensitivity to VX-970

ARID1A-knockout HCT116 cells were more sensitive to VX-970 compared to control cells (FIG. 9). A cell growth curve was prepared following 72 h of treatment with different concentrations of VX-970.

REFERENCES

1. Wilson, B. G. & Roberts, C. W. SWI/SNF nucleosome remodellers and cancer. *Nature Reviews Cancer* 11, 481 (2011).
2. Wiegand, K. C. et al. ARID1A mutations in endometriosis-associated ovarian carcinomas. *New England Journal of Medicine* 363, 1532-1543 (2010).
3. Jones, S. et al. Frequent mutations of chromatin remodeling gene ARID1A in ovarian clear cell carcinoma. *Science* 330, 228-231 (2010).
4. Wu, R.-C., Wang, T.-L. & Shih, I.-M. The emerging roles of ARID1A in tumor suppression. *Cancer Biology & Therapy* 15, 655-664 (2014).
5. Forbes, S. A. et al. COSMIC: somatic cancer genetics at high-resolution. *Nucleic Acids Research* 45, D777-D783 (2016).
6. Anglesio, M. S. et al. Type-specific cell line models for type-specific ovarian cancer research. *PLoS ONE* 8, e72162 (2013).
7. Dykhuizen, E. C. et al. BAF complexes facilitate decatenation of DNA by topoisomerase IIα. *Nature* 497, 624 (2013).
8. Guan, B., Wang, T.-L. & Shih, I.-M. ARID1A, a factor that promotes formation of SWI/SNF-mediated chromatin remodeling, is a tumor suppressor in gynecologic cancers. *Cancer Research* 71, 6718-6727 (2011).
9. Robitaille, A. M. et al. Quantitative phosphoproteomics reveal mTORC1 activates de novo pyrimidine synthesis. *Science* 339, 1320-1323 (2013).
10. Ben-Sahra, I., Howell, J. J., Asara, J. M. & Manning, B. D. Stimulation of de novo pyrimidine synthesis by growth signaling through mTOR and S6K1. *Science* 339, 1323-1328 (2013).
11. Barretina, J. et al. The Cancer Cell Line Encyclopedia enables predictive modelling of anticancer drug sensitivity. *Nature* 483, 603 (2012).
12. O'Connor, P. et al. Randomized trial of oral teriflunomide for relapsing multiple sclerosis. *New England Journal of Medicine* 365, 1293-1303 (2011).
13. Bitler, B. G. et al. Synthetic lethality by targeting EZH2 methyltransferase activity in ARID1A-mutated cancers. *Nature Medicine* 21, 231 (2015).
14. Williamson, C. T. et al. ATR inhibitors as a synthetic lethal therapy for tumours deficient in ARID1A. *Nature Communications* 7, 13837 (2016).
15. Bitler, B. G. et al. ARID1A-mutated ovarian cancers depend on HDAC6 activity. *Nature Cell Biology* 19, 962 (2017).
16. Shen, J. et al. ARID1A deficiency impairs the DNA damage checkpoint and sensitizes cells to PARP inhibitors. *Cancer Discovery* 5, 752-767 (2015).
17. Samartzis, E. P. et al. Loss of ARID1A expression sensitizes cancer cells to PI3K- and AKT-inhibition. *Oncotarget* 5, 5295 (2014).
18. Lee, D., Yu, E. J., Ham, I.-H., Hur, H. & Kim, Y.-S. AKT inhibition is an effective treatment strategy in ARID1A-deficient gastric cancer cells. *OncoTargets and Therapy* 10, 4153 (2017).
19. Chandler, R. L. et al. Coexistent ARID1A-PIK3CA mutations promote ovarian clear-cell tumorigenesis through pro-tumorigenic inflammatory cytokine signalling. *Nature Communications* 6, 6118 (2015).
20. Rees, S. et al. Bicistronic vector for the creation of stable mammalian cell lines that predisposes all antibiotic-resistant cells to express recombinant protein. *BioTechniques* 20, 102-110 (1996).
21. Yang, C.-P. H. & Horwitz, S. B. Taxol mediates serine phosphorylation of the 66-kDa Shc isoform. *Cancer Research* 60, 5171-5178 (2000).
22. Keller, D. M., Zeng, S. X. & Lu, H. Interaction of p53 with cellular proteins. *Methods in molecular biology* (Clifton, N.J.) 234, 121-133, doi:10.1385/1-59259-408-5:121 (2003).
23. Huang, G. S. et al. Insulin-like growth factor 2 expression modulates Taxol resistance and is a candidate biomarker for reduced disease-free survival in ovarian cancer. *Clinical Cancer Research* 16, 2999-3010 (2010).
24. Reagan-Shaw, S., Nihal, M. & Ahmad, N. Dose translation from animal to human studies revisited. *The FASEB Journal* 22, 659-661 (2008).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

SEQUENCE LISTING

| SEQ ID NO. | Name | Sequence |
|---|---|---|
| 1 | sh1 (TRCN0000059090) | CCTCTCTTATACACAGCAGAT |
| 2 | sh2 (TRCN0000059091) | CCGTTGATGAACTCATTGGTT |
| 3 | shCon | CCTAAGGTTAAGTCGCCCTCGCTCGAGCGAGGGCGACTTAACCTTAGG |
| 4 | HA-tagged full-length ARID1A | GAATTCATGTACCCATACGATGTTCCAGATTACGCTGCTAGCCTCGAGCCACCATGGCCGCG CAGGTCGCCCCCGCCGCCGCCAGCAGCCTGGGCAACCCGCCGCCGCCGCCGCCCTCGGA GCTGAAGAAAGCCGAGCAGCAGCAGCGGGAGGAGGCGGGGGGCGAGGCGGCGGCGGCG GCAGCGGCCGAGCGCGGGGAAATGAAGGCAGCCGCCGGGCAGGAAAGCGAGGGCCCCGC CGTGGGGCCGCCGCAGCCGCTGGGAAAGGAGCTGCAGGACGGGGCCGAGAGCAATGGGG GTGGCGGCGGCGGCGGAGCCGGCAGCGGCGGCGGGCCCGGCGCGGAGCGGACCTGAA GAACTCGAACGGGAACGCGGGCCCTAGGCCCGCCCTGAACAATAACCTCACGGAGCCGCC CGGCGGCGGCGGTGGCGGCAGCAGCGATGGGGTGGGGGCGCCTCCTCACTCAGCCGCGG CCGCCTTGCCGCCCCCAGCCTACGGCTTCGGGCAACCCTACGGCCGGAGCCCGTCTGCCG TCGCCGCCGCCGCGGCCGCCGTCTTCCACCAACAACATGGCGGACAACAAAGCCCTGGCCT |

SEQUENCE LISTING

| SEQ ID NO. | Name | Sequence |
|---|---|---|
| | | GGCAGCGCTGCAGAGCGGCGGCGGCGGGGGCCTGGAGCCCTACGCGGGGCCCCAGCAGA |
| | | ACTCTCACGACCACGGCTTCCCCAACCACCAGTACAACTCCTACTACCCCAACCGCAGCGCC |
| | | TACCCCCCGCCCGCCCCGGCCTACGCGCTGAGCTCCCCGAGAGGTGGCACTCCGGGCTCC |
| | | GGCGCGGCGGCGGCTGCCGGCTCCAAGCCGCCTCCCTCCTCCAGCGCCTCCGCCTCCTCG |
| | | TCGTCTTCGTCCTTCGCTCAGCAGCGCTTCGGGGCCATGGGGGGAGGCGGCCCCTCCGCG |
| | | GCCGGCGGGGGAACTCCCCAGCCCACCGCCACCCCCACCCTCAACCAACTGCTCACGTCG |
| | | CCCAGCTCGGCCCGGGGCTACCAGGGCTACCCCGGGGGCGACTACAGTGGCGGGCCCCA |
| | | GGACGGGGGCGCCGGCAAGGGCCCGGCGGACATGGCCTCGCAGTGTTGGGGGGCTGCGG |
| | | CGGCGGCAGCTGCGGCGGCGGCGCCTCGGGAGGGGCCCAACAAAGGAGCCACCACGCG |
| | | CCCATGAGCCCCGGGAGCAGCGGCGGCGGGGGGCAGCCGCTCGCCCGGACCCCTCAGCC |
| | | ATCCAGTCCAATGGATCAGATGGGCAAGATGAGACCTCAGCCATATGGCGGGACTAACCCAT |
| | | ACTCGCAGCAACAGGGACCTCCGTCAGGACCGCAGCAAGGACATGGGTACCCAGGGCAGC |
| | | CATACGGGTCCCAGACCCCGCAGCGGTACCCGATGACCATGCAGGGCCGGGCGCAGAGTG |
| | | CCATGGGCGGCCTCTCTTATACACAGCAGATTCCTCCTTATGGACAACAAGGCCCCAGCGGG |
| | | TATGGTCAACAGGGCCAGACTCCATATTACAACCAGCAAAGTCCTCACCCTCAGCAGCAGCA |
| | | GCCACCCTACTCCCAGCAACCACCGTCCCAGACCCCTCATGCCCAACCTTCGTATCAGCAGC |
| | | AGCCACAGTCTCAACCACCACAGCTCCAGTCCTCTCAGCCTCCATACTCCCAGCAGCCATCC |
| | | CAGCCTCCACATCAGCAGTCCCCGGCTCCATACCCCTCCCAGCAGTCGACGACACAGCAGC |
| | | ACCCCCAGAGCCAGCCCCCTACTCACAGCCACAGGCTCAGTCTCCTTACCAGCAGCAGCA |
| | | ACCTCAGCAGCCAGCACCCTCGACGCTCTCCCAGCAGGCTGCGTATCCTCAGCCCCAGTCT |
| | | CAGCAGTCCCAGCAAACTGCCTATTCCCAGCAGCGCTTCCCTCCACCGCAGGAGCTATCTCA |
| | | AGATTCATTTGGGTCTCAGGCATCCTCAGCCCCCTCAATGACCTCCAGTAAGGGAGGGCAAG |
| | | AAGATATGAACCTGAGCCTTCAGTCAAGACCCTCCAGCTTGCCTGATCTATCTGGTTCAATAG |
| | | ATGACCTCCCCATGGGGACAGAAGGAGCTCTGAGTCCTGGAGTGAGCACATCAGGGATTTC |
| | | CAGCAGCCAAGGAGAGCAGAGTAATCCAGCTCAGTCTCCTTTCTCTCCTCATACCTCCCCTC |
| | | ACCTGCCTGGCATCCGAGGCCCTTCCCCGTCCCTGTTGGCTCTCCCGCCAGTGTTGCTCA |
| | | GTCTCGCTCAGGACCACTCTCGCCTGCTGCAGTGCCAGGCAACCAGATGCCACCTCGGCCA |
| | | CCCAGTGGCCAGTCGGACAGCATCATGCATCCTTCCATGAACCAATCAAGCATTGCCCAAGA |
| | | TCGAGGTTATATGCAGAGGAACCCCCAGATGCCCCAGTACAGTTCCCCCCAGCCCGGCTCA |
| | | GCCTTATCTCCGCGTCAGCCTTCCGGAGGACAGATACACACAGGCATGGGCTCCTACCAGC |
| | | AGAACTCCATGGGGAGCTATGGTCCCCAGGGGGGTCAGTATGGCCCACAAGGTGGCTACCC |
| | | CAGGCAGCCAAACTATAATGCCTTGCCCAATGCCAACTACCCCAGTGCAGGCATGGCTGGAG |
| | | GCATAAACCCCATGGGTGCCGGAGGTCAAATGCATGGACAGCCTGGCATCCCACCTTATGG |
| | | CACACTCCCTCCAGGGAGGATGAGTCACGCCTCCATGGGCAACCGGCCTTATGGCCCTAAC |
| | | ATGGCCAATATGCCACCTCAGGTTGGGTCAGGGATGTGTCCCCCACCAGGGGGCATGAACC |
| | | GGAAAACCCAAGAAACTGCTGTCGCCATGCATGTTGCTGCCAACTCTATCCAAAACAGGCCG |
| | | CCAGGCTACCCCAATATGAATCAAGGGGCATGATGGGAACTGGACCTCCTTATGGACAAGG |
| | | GATTAATAGTATGGCTGGCATGATCAACCCTCAGGGACCCCCATATTCCATGGGTGGAACCA |
| | | TGGCCAACAATTCTGCAGGGATGGCAGCCAGCCCAGAGATGATGGGCCTTGGGGATGTAAA |
| | | GTTAACTCCAGCCACCAAAATGAACAACAAGGCAGATGGGACACCCAAGACAGAATCCAAAT |
| | | CCAAGAAATCCAGTTCTTCTACTACAACCAATGAGAAGATCACCAAGTTGTATGAGCTGGGTG |
| | | GTGAGCCTGAGAGGAAGATGTGGGTGGACCGTTATCTGGCCTTCACTGAGGAGAAGGCCAT |
| | | GGGCATGACAAATCTGCCTGCTGTGGGTAGGAAACCTCTGGACCTCTATCGCCTCTATGTGT |
| | | CTGTGAAGGAGATTGGTGGATTGACTCAGGTCAACAAGAACAAAAAATGGCGGGAACTTGCA |
| | | ACCAACCTCAATGTGGGCACATCAAGCAGTGCTGCCAGCTCCTTGAAAAAGCAGTATATCCA |
| | | GTGTCTCTATGCCTTTGAATGCAAGATTGAACGGGGAGAAGACCCTCCCCCAGACATCTTTG |
| | | CAGCTGCTGATTCCAAGAAGTCCCAGCCCAAGATCCAGCCTCCCTCTCCTGCGGGATCAGGA |
| | | TCTATGCAGGGGCCCCAGACTCCCCAGTCAACCAGCAGTTCCATGGCAGAAGGAGGAGACT |
| | | TAAAGCCACCAACTCCAGCATCCACACCACACAGTCAGATCCCCCCATTGCCAGGCATGAGC |
| | | AGGAGCAATTCAGTTGGGATCCAGGATGCCTTTAATGATGGAAGTGACTCCACATTCCAGAA |
| | | GCGGAATTCCATGACTCCAAACCCTGGGTATCAGCCCAGTATGAATACCTCTGACATGATGG |
| | | GGCGCATGTCCTATGAGCCAAATAAGGATCCTTATGGCAGCATGAGGAAAGCTCCAGGGAGT |
| | | GATCCCTTCATGTCCTCAGGGCAGGGCCCCAACGGCGGGATGGGTGACCCCTACAGTCGTG |
| | | CTGCCGGCCCTGGGCTAGGAAATGTGGCGATGGGACCACGACAGCACTATCCCTATGGAGG |
| | | TCCTTATGACAGAGTGAGGACGGAGCCTGGAATAGGGCCTGAGGGAAACATGAGCACTGGG |
| | | GCCCCACAGCCGAATCTCATGCCTTCCAACCCAGACTCGGGGATGTATTCTCCTAGCCGCTA |
| | | CCCCCCGCAGCAGCAGCAGCAGCAGCAGCAACGACATGATTCCTATGGCAATCAGTTCTCCA |
| | | CCCAAGGCACCCTTCTGGCAGCCCTTCCCCAGCCAGCAGACTACAATGTATCAACAGCAA |
| | | CAGCAGAATTACAAGCGGCCAATGGATGGCACATATGGCCCTCCTGCCAAGCGGCACGAAG |
| | | GGGAGATGTACAGCGTGCCATACAGCACTGGGCAGGGGCAGCCTCAGCAGCAGCAGTTGC |
| | | CCCCAGCCCAGCCCCAGCCTGCCAGCCAGCAACAAGCTGCCCAGCCTTCCCCTCAGCAAGA |
| | | TGTATACAACCAGTATGGCAATGCCTATCCTGCCACTGCCACAGCTGCTACTGAGCGCCGAC |
| | | CAGCAGGCGGCCCCCAGAACCAATTTCCATTCCAGTTTGGCCGAGACCGTGTCTCTGCACCC |
| | | CCTGGCACCAATGCCCAGCAAAACATGCCACCACAAATGATGGGCGGCCCCATACAGGCAT |
| | | CAGCTGAGGTTGCTCAGCAAGGCACCATGTGGCAGGGCGTAATGACATGACCTATAATTAT |
| | | GCCAACAGGCAGAGCACGGGCTCTGCCCCCCAGGGCCCCGCCTATCATGGCGTGAACCGA |
| | | ACAGATGAAATGCTGCACACAGATCAGAGGGCCAACCACGAAGGCTCGTGGCCTTCCCATG |
| | | GCACACGCCAGCCCCATATGGTCCCTCTGCCCCTGTGCCCCCATGACAAGGCCCCCTCC |
| | | ATCTAACTACCAGCCCCCACCAAGCATGCAGAATCACATTCCTCAGGTATCCAGCCCTGCTC |
| | | CCCTGCCCCGGCCAATGGAGAACCGCACCTCTCCTAGCAAGTCTCCATTCCTGCACTCTGGG |
| | | ATGAAAATGCAGAAGGCAGGTCCCCAGTACCTGCCTCGCACATAGCACCTGCCCCTGTGCA |
| | | GCCCCCCATGATTCGGCGGGATATCACCTTCCCACCTGGCTCTGTTGAAGCCACACAGCCTG |
| | | TGTTGAAGCAGAGGAGGCGGCTCACAATGAAAGACATTGAACCCCGGAGGCATGGCGGGT |
| | | AATGATGTCCCTCAAGTCTGGTCTCCTGGCAGAGAGCACATGGGCATTAGATACCATCAACA |

| SEQ ID NO. | Name | Sequence |
|---|---|---|
| | | TCCTGCTGTATGATGACAACAGCATCATGACCTTCAACCTCAGTCAGCTCCCAGGGTTGCTA
GAGCTCCTTGTAGAATATTTCCGACGATGCCTGATTGAGATCTTTGGCATTTTAAAGGAGTAT
GAGGTGGGTGACCCAGGACAGAGAACGCTACTGGATCCTGGGAGGTTCAGCAAGGTGTCTA
GTCCAGCTCCCATGGAGGGTGGGGAAGAAGAAGAAGAACTTCTAGGTCCTAAACTAGAAGA
GGAAGAAGAAGAGGAAGTAGTTGAAAATGATGAGGAGATAGCCTTTTCAGGCAAGGACAAGC
CAGCTTCAGAGAATAGTGAGGAGAAGCTGATCAGTAAGTTTGACAAGCTTCCAGTAAAGATC
GTACAGAAGAATGATCCATTTGTGGTGGACTGCTCAGATAAGCTTGGGCGTGTGCAGGAGTT
TGACAGTGGCCTGCTGCACTGGCGGATTGGTGGGGGGGACACCACTGAGCATATCCAGACC
CACTTCGAGAGCAAGACAGAGCTGCTGCCTTCCCGGCCTCACGCACCCTGCCCACCAGCCC
CTCGGAAGCATGTGACAACAGCAGAGGGTACACCAGGGACAACAGACCAGGAGGGGCCCC
CACCTGATGGACCTCCAGAAAAACGGATCACAGCCACTATGGATGACATGTTGTCTACTCGG
TCTAGCACCTTGACCGAGGATGGAGCTAAGAGTTCAGAGGCCATCAAGGAGAGCAGCAAGTT
TCCATTTGGCATTAGCCCAGCACAGAGCCACCGGAACATCAAGATCCTAGAGGACGAACCCC
ACAGTAAGGATGAGACCCCACTGTGTACCCTTCTGGACTGGCAGGATTCTCTTGCCAAGCGC
TGCGTCTGTGTGTCCAATACCATTCGAAGCCTGTCATTTGTGCCAGGCAATGACTTTGAGATG
TCCAAACACCCAGGGCTGCTGCTCATCCTGGGCAAGCTGATCCTGCTGCACCACAAGCACC
CAGAACGGAAGCAGGCACCACTAACTTATGAAAAGGAGGAGGAACAGGACCAAGGGGTGAG
CTGCAACAAAGTGGAGTGGTGGTGGGACTGCTTGGAGATGCTCCGGGAAAACACCTTGGTT
ACACTCGCCAACATCTCGGGGCAGTTGGACCTATCTCCATACCCGAGAGCATTTGCCTGCC
TGTCCTGGACGGACTCCTACACTGGGCAGTTTGCCCTTCAGCTGAAGCCCAGGACCCCTTTT
CCACCCTGGGCCCAATGCCGTCCTTTCCCGCAGAGACTGGTCTTGGAAACCCTCAGCAAA
CTCAGCATCCAGGACAACAATGTGGACCTGATTCTGGCCACACCCCCCTTCAGCCGCCTGGA
GAAGTTGTATAGCACTATGGTGCGCTTCCTCAGTGACCGAAAGAACCCGGTGTGCCGGGAG
ATGGCTGTGGTACTGCTGGCCAACCTGGCTCAGGGGACAGCCTGGCAGCTCGTGCCATTG
CAGTGCAGAAGGGCAGTATCGGCAACCTCCTGGGCTTCCTAGAGGACAGCCTTGCCGCCAC
ACAGTTCCAGCAGAGCCAGGCCAGCCTCCTCCACATGCAGAACCCACCCTTTGAGCCAACTA
GTGTGGACATGATGCGGCGGGCTGCCCGCGCGCTGCTTGCCTTGGCCAAGGTGGACGAGA
ACCACTCAGAGTTTACTCTGTACGAATCACGGCTGTTGGACATCTCGGTATCACCGTTGATGA
ACTCATTGGTTTCACAAGTCATTTGTGATGTACTGTTTTTGATTGGCCAGTCCTCGTGAGGAT
CC |
| 5 | GST-tagged full-length CAD | GCTAGAATTCGTATGGCGGCCCTAGTGTTGGAGGACGGGTCGGTCCTGCGGGGCCAGCCCT
TTGGGGCCGCCGTGTCGACTGCCGGGGAAGTGGTGTTTCAAACCGGCATGGTCGGCTACCC
CGAGGCCCTCACTGATCCCTCCTACAAGGCACAGATCTTAGTGCTCACCTATCCTCTGATCG
GCAACTATGGCATCCCCCCAGATGAAATGGATGAGTTCGGTCTCTGCAAGTGGTTTGAATCC
TCGGGCATCCACGTAGCAGCACTGGTAGTGGGAGAGTGCTGTCCTACTCCCAGCCACTGGA
GTGCCACCCGCACCCTGCATGAGTGGCTGCAGCAGCATGGCATCCCTGGCTTGCAAGGAGT
AGACACTCGGGAGCTGACCAAGAAGTTGCGGGAACAGGGGTCTCTGCTGGGGAAGCTGGTC
CAGAATGGAACAGAACCTTCATCCCTGCCATTCTTGGACCCCAATGCCCGCCCCCTGGTACC
AGAGGTCTCCATTAAGACTCCACGGGTATTCAATACAGGGGGTGCCCCTCGGATCCTTGCTT
TGGACTGTGGCCTCAAGTATAATCAGATCCGATGCCTCTGCCAGCGTGGGGCTGAGGTCACT
GTGGTACCCTGGGACCATGCACTAGACAGCCAAGAGTATGAGGGTCTCTTCTTAAGTAATGG
GCCTGGTGACCCTGCCTCCTATCCCAGTGTCGTATCCACACTGAGCCGTGTTTTATCGAGC
CTAATCCCCGACCTGTCTTTGGGATCGCCTGGGACACCAGCTATTGGCCTTAGCCATTGGG
GCCAAGACTTACAAGATGAGATATGGGAACCGAGGCCATAACCAGCCCTGCTTGTTGGTGGG
CTCTGGGCGCTGCTTTCTGACATCCCAGAACCATGGGTTTGCTGTGGAGACAGACTCACTGC
CAGCAGACTGGGCTCCTCTCTTCACCAACGCCAATGATGGTTCCAATGAAGGCATTGTGCAC
AACAGCTTGCCTTTCTTCAGTGTCCAGTTTCACCCAGAGCACCAAGCTGGCCCTTCAGATATG
GAACTGCTTTTCGATATCTTTCTGGAAACTGTGAAAGAGGCCACAGCTGGGAACCCTGGGGG
CCAGACAGTTAGAGAGCGGCTGACTGAGCGCCTCTGTCCCCCTGGGATTCCCACTCCCGGC
TCTGGACTTCCACCACCACGAAAGGTTCTGATCCTGGGCTCAGGGGCCTCTCCATTGGCCA
AGCTGGAGAATTTGACTACTCGGGCTCTCAGGCAATTAAGGCCCTGAAGGAGGAAAACATCC
AGACGTTGCTGATCAACCCCAATATTGCCACAGTGCAGACCTCCCAGGGGCTGGCCGACAA
GGTCTATTTTCTTCCCATAACACCTCATTATGTAACCCAGGTGATACGTAATGAACGCCCCGA
TGGTGTGTTACTGACTTTTGGGGGCCAGACTGCTCTGAACTGTGGTGTGGAGCTGACCAAGG
CCGGGGTGCTGGCTCGGTATGGGGTCCGGGTCCTGGGCACACCAGTGGAGACCATTGAGC
TGACCGAGGATCGACGGGCCTTTGCTGCCAGAATGGCAGAGATCGGAGAGCATGTGGCCCC
GAGCGAGGCAGCAAATTCTCTTGAACAGGCCCAGGCAGCCGCTGAACGGCTGGGGTACCCT
GTGCTAGTGCGTGCAGCCTTTGCCCTGGGTGGCCTGGGCTCTGGCTTTGCCTCTAACAGGG
AGGAGCTCTCTGCTCTCGTGGCCCAGCTTTTGCCCATACCAGCCAAGTGCTAGTAGACAAG
TCTCTGAAGGGATGAAGGAGATTGAGTACGAGGTGGTGAGAGACGCCTATGGCAACTGTG
TCACGGTGTGTAACATGGAGAACTTGGACCCACTGGGCATCCACACTGGTGAGTCCATAGTG
GTGGCCCCTAGCCAGACACTGAATGACAGGAGTATCAGCTCCTGAGGCAGACAGCTATCA
AGGTGACCCAGCACCTGGGAATTGTTGGGGAGTGCAATGTGCAGTATGCCTTGAACCCTGA
GTCTGAGCAGTATTACATCATTGAAGTGAATGCCAGGCTCTCTCGCAGCTCTGCCCTGGCCA
GTAAGGCCACAGGTTATCCACTGGCTTATGTGGCAGCCAAGCTAGCATTGGGCATCCCTTTG
CCTGAGCTCAGGAACTCTGTGACAGGGGGTACAGCAGCCTTTGAACCCAGCGTGGATTATTG
TGTGGTGAAGATTCCTCGATGGGACCTTAGCAAGTTCCTGCGAGTCAGCACAAAGATTGGGA
GCTGCATGAAGAGCGTTGGTGAAGTCATGGGCATTGGGCGTTCATTTGAGGAGGCCTTCCA
GAAGGCCCTGCGCATGGTGGATGAGAACTGTGTGGGCTTTGATCACACAGTGAAACCAGTCA
GCGATATGGAGTTGGAGACTCCAACAGATAAGCGGATTTTTGTGGTGGCAGCTGCTTTGTGG
GCTGGTTATTCAGTGGACCGCCTGTATGAGCTCACACGCATCGACCGCTGGTTCCTGCACCG
AATGAAGCGTATCATCGACATGCCCAGCTGCTAGAACAACACCGTGGACAGCCTTTGCCGC
CAGACCTGCTGCAACAGGCCAAGTGTCTTGGCTTCTCAGACAAACAGATTGCCCTTGCAGTT |

SEQUENCE LISTING

| SEQ ID NO. | Name | Sequence |
|---|---|---|
| | | CTGAGCACAGAGCTGGCTGTTCGCAAGCTGCGTCAGGAACTGGGGATCTGTCCAGCAGTGA |
| | | AACAGATTGACACAGTTGCAGCTGAGTGGCCAGCCCAGACAAATTACCTATACCTAACGTATT |
| | | GGGGCACCACCCATGACCTCACCTTTCGAACACCTCATGTCCTAGTCCTTGGCTCTGGCGTC |
| | | TACCGTATTGGCTCTAGCGTTGAATTTGACTGGTGTGCTGTAGGCTGCATCCAGCAGCTCCG |
| | | AAAGATGGGATATAAGACCATCATGGTGAACTATAACCCAGAGACAGTCAGCACCGACTATG |
| | | ACATGTGTGATCGACTCTACTTTGATGAGATCTCTTTTGAGGTGGTGATGGACATCTATGAGC |
| | | TCGAGAACCCTGAAGGTGTGATCCTATCCATGGGTGGACAGCTGCCCAACAACATGGCCATG |
| | | GCGTTGCATCGGCAGCAGTGCCGGGTGCTGGGCACCTCCCCTGAAGCCATTGACTCGGCTG |
| | | AGAACCGTTTCAAGTTTTCCCGGCTCCTTGACACCATTGGTATCAGCCAGCCTCAGTGGAGG |
| | | GAGCTCAGTGACCTCGAGTCTGCTCGCCAATTCTGCCAGACCGTGGGGTACCCCTGTGTGG |
| | | TGCGCCCTCCTATGTGCTGAGCGGTGCTGCTATGAATGTGGCCTACACGGATGGAGACCT |
| | | GGAGCGCTTCCTGAGCAGCGCCAGCAGCCGTCTCCAAAGAGCATCCCGTGGTCATCTCCAAG |
| | | TTCATCCAGGAGGCTAAGGAGATTGACGTGGATGCCGTGGCCTCTGATGGTGTGGTGGCAG |
| | | CCATCGCCATCTCTGAGCATGTGGAGAATGCAGGTGTGCATTCAGGTGATGCGACGCTGGT |
| | | GACCCCCCCACAAGATATCACTGCCAAAACCCTGGAGCGGATCAAAGCCATTGTGCATGCTG |
| | | TGGGCCAGGAGCTACAGGTCACAGGACCCTTCAATCTGCAGCTCATTGCCAAGGATGACCA |
| | | GCTGAAAGTTATTGAATGCAACGTACGTGTCTCGCTCCTTCCCCTTCGTTTCCAAGACACT |
| | | GGGTGTGGACCTAGTAGCCTTGGCCACGCGGGTCATCATGGGGGAAGAAGTGGAACCTGTG |
| | | GGGCTAATGACTGGTTCTGGAGTCGTGGGAGTAAAGGTGCCTCAGTTCTCCTTCTCCCGCTT |
| | | GGCGGGTGCTGACGTGGTGTTGGGTGTGGAAATGACCAGTACTGGGGAGGTGGCCGGCTTT |
| | | GGGGAGAGCCGCTGTGAGGCATACCTCAAGGCCATGCTAAGCACTGGCTTTAAGATCCCCA |
| | | AGAAGAATATCCTGCTGACCATTGGCAGCTATAAGAACAAAAGCGAGCTGCTCCCAACTGTG |
| | | CGGCTACTGGAGAGCCTGGCTACAGCCTCTATGCCAGTCTCGGCACAGCTGACTTCTACAC |
| | | TGAGCATGGCGTCAAGGTAACAGCTGTGGACTGGCACTTTGAGGAGGCTGTGGATGGTGAG |
| | | TGCCCACCACAGCGGAGCATCCTGGAGCAGCTAGCTGAGAAAAACTTTGAGCTGGTGATTAA |
| | | CCTGTCAATGCGTGGAGCTGGGGGCCGGCGTCTCTCTTCCTTTGTCACCAAGGGCTACCGC |
| | | ACCCGACGCTTGGCCGCTGACTTCTCCGTGCCCCTAATCATCGATATCAAGTGCACCAAACT |
| | | CTTTGTGGAGGCCCTAGGCCAGATCGGGCCAGCCCCTCCTTTGAAGGTGCATGTTGACTGTA |
| | | TGACCTCCCAAAAGCTTGTGCGACTGCCGGGATTGATTGATGTCCATGTGCACCTGCGGGAA |
| | | CCAGGTGGGACACATAAGGAGGACTTTGCTTCAGGCACAGCCGCTGCCCTGGCTGGGGGTA |
| | | TCACCATGGTGTGTGCCATGCCTAATACCCGGCCCCCCATCATTGACGCCCCTGCTCTGGCC |
| | | CTGGCCCAGAAGCTGGCAGAGGCTGGCGCCCGGTGCGACTTTGCGCTATTCCTTGGGGCCT |
| | | CGTCTGAAAATGCAGGAACCTTGGGCACCGTGGCCGGGTCTGCAGCCGGGCTGAAGCTTTA |
| | | CCTCAATGAGACCTTCTCTGAGCTGCGGCTGGACAGCGTGGTCCAGTGGATGGAGCATTTC |
| | | GAGACATGGCCCTCCCACCTCCCATTGTGGCTCACGCAGAGCAGCAAACCGTGGCTGCTG |
| | | TCCTCATGGTGGCTCAGCTCACTCAGCGCTCAGTGCACATATGTCACGTGGCACGGAAGGA |
| | | GGGAGATCCTGCTAATTAAAGCTGCAAAGGCACGGGGCTTGCCAGTGACCTGCGAGGTGGCT |
| | | CCCCACCACCTGTTCCTAAGCCATGATGACCTGGAGCGCCTGGGGCTGGGAAGGGGGAG |
| | | GTCCGGCCTGAGCTTGGCTCCCGCCAGGATGTGGAAGCCCTGTGGGAGAACATGGCTGTCA |
| | | TCGACTGCTTTGCCTCAGACCATGCTCCCCATACCTTGGAGGAGAAGTGTGGGTCCAGGCCC |
| | | CCACCTGGGTTCCCAGGGTTAGAGACCATGCTGCCACTACTCCTGACGGCTGTAAGCGAGG |
| | | GCCGGCTCAGCCTGGACGACCTGCTGCAGCGATTGCACCACAATCCTCGGCGCATCTTTCA |
| | | CCTGCCCCCGCAGGAGGACACCTATGTGGAGGTGGATCTGGAGCATGAGTGGACAATTCCC |
| | | AGCCACATGCCCTTCTCCAAGGCCCACTGGACACCTTTTGAAGGGCAGAAAGTGAAGGGCA |
| | | CCGTCCGCCGTGTGGTCCTGCGAGGGGAGGTTGCCTATATCGATGGGCAGGTTCTGGTACC |
| | | CCCGGGCTATGGACAGGATGTACGGAAGTGGCCACAGGGGGCTGTTCCTCAGCTCCCACCC |
| | | TCAGCCCCTGCCACTAGTGAGATGACCACGACACCTGAAAGACCCCGCCGTGGCATCCCAG |
| | | GGCTTCCTGATGGCCGCTTCCATCTGCCGCCCCGAATCCATCGAGCCTCCGACCCAGGTTT |
| | | GCCAGCTGAGGAGCCAAAGGAGAAGTCCTCTCGGAAGGTAGCCGAGCCAGAGCTGATGGG |
| | | AACCCCTGATGGCACCTGCTACCCTCCACCACCAGTACCGAGACAGGCATCTCCCCAGAACC |
| | | TGGGGACCCCTGGCTTGCTGCACCCCCAGACCTCACCCCTGCTGCACTCATTAGTGGGCCA |
| | | ACATATCCTGTCCGTCCAGCAGTTCACCAAGGATCAGATGTCTCACCTGTTCAATGTGGCACA |
| | | CACACTGCGTATGATGGTGCAGAAGGAGCGGAGCCTCGACATCCTGAAGGGGAAGGTCATG |
| | | GCCTCCATGTTCTATGAAGTGAGCACACGGACCAGCAGCTCCTTTGCAGCAGCCATGGCCC |
| | | GGCTGGGAGGTGCTGTGCTCAGCTTCTCGGAAGCCACATCGTCCGTCCAGAAGGGCGAATC |
| | | CCTGGCTGACTCCGTGCAGACCATGAGCTGCTATGCCGACGTCGTCGTGCTCCGGCACCCC |
| | | CAGCCTGGAGCAGTGGAGCTGGCCGCCAAGCACTGCCGGAGGCCAGTGATCAATGCTGGG |
| | | GATGGGGTCGGAGAGCACCCCACCCAGGCCCTGCTGGACATCTTCACCATCCGTGAGGAGC |
| | | TGGGAACTGTCAATGGCATGACGATCACGATGGTGGGTGACCTGAAGCACGGACGCACAGT |
| | | ACATTCCCTGGCCTGCCTGCTCACCCAGTATCGTGTCAGCCTGCGCTACGTGGCACCTCCCA |
| | | GCCTGCGCATGCCACCCACTGTGCGGGCCTTCGTGGCCTCCCGCGGCACCAAGCAGGAGG |
| | | AATTCGAGAGCATTGAGGAGGCGCTGCCTGACACTGATGTGCTCTACATGACTCGAATCCAG |
| | | AAGGAACGATTTGGCTCTACCCAGGAGTACGAAGCTTGCTTTGGTCAGTTCATCCTCACTCC |
| | | CCACATCATGACCCGGGCCAAGAAGAAGATGGTGGTGATGCACCCGATGCCCCGTGTCAAC |
| | | GAGATAAGCGTGGAAGTGGACTCGGATCCCCGCGCAGCCTACTTCCGCCAGGCTGAGAACG |
| | | GCATGTACATCCGCATGGCTCTGTTAGCCACCGTGCTGGGCCGTTTCTAGGCGGCCGCATC |
| | | C |
| 6 | GST-GLNase | GCTAGAATTCGTATGGCGGCCCTAGTGTTGGAGGACGGGTCGGTCCTGCGGGGCCAGCCCT |
| | | TTGGGGCCGCCGTGTCGACTGCCGGGGAAGTGGTGTTTCAAACCGGCATGGTCGGCTACCC |
| | | CGAGGCCCTCACTGATCCCTCCTACAAGGCACAGATCTTAGTGCTCACCTATCCTCTGATCG |
| | | GCAACTATGGCATCCCCCCAGATGAAATGGATGAGTTCGGTCTCTGCAAGTGGTTTGAATCC |

| SEQ ID NO. | Name | Sequence |
|---|---|---|
| | | TCGGGCATCCACGTAGCAGCACTGGTAGTGGGAGAGTGCTGTCCTACTCCCAGCCACTGGA<br>GTGCCACCCGCACCCTGCATGAGTGGCTGCAGCAGCATGGCATCCCTGGCTTGCAAGGAGT<br>AGACACTCGGGAGCTGACCAAGAAGTTGCGGGAACAGGGCGGCCGCATCC |
| 7 | GST-CPSase | GCTAGAATTCGTGGTCTCTGCTGGGGAAGCTGGTCCAGAATGGAACAGAACCTTCATCCCTG<br>CCATTCTTGGACCCCAATGCCCGCCCCTGGTACCAGAGGTCTCCATTAAGACTCCACGGGT<br>ATTCAATACAGGGGGTGCCCCTCGGATCCTTGCTTTGGACTGTGGCCTCAAGTATAATCAGA<br>TCCGATGCCTCTGCCAGCGTGGGGCTGAGGTCACTGTGGTACCCTGGGACCATGCACTAGA<br>CAGCCAAGAGTATGAGGGTCTCTTCTTAAGTAATGGGCCTGGTGACCCTGCCTCCTATCCCA<br>GTGTCGTATCCACACTGAGCCGTGTTTTATCTGAGCCTAATCCCCGACCTGTCTTTGGGATCT<br>GCCTGGGACACCAGCTATTGGCCTTAGCCATTGGGGCAAGACTTACAAGATGAGATATGGG<br>AACCGAGGCCATAACCAGCCCTGCTTGTTGGTGGGCTCTGGGCGCTGCTTTCTGACATCCCA<br>GAACCATGGGTTTGCTGTGGAGACAGACTCACTGCCAGCAGACTGGGCTCCTCTCTTCACCA<br>ACGCCAATGATGGTTCCAATGAAGGCATTGTGCACAACAGCTTGCCTTTCTTCAGTGTCCAGT<br>TTCACCCAGAGCACCAAGCTGGCCCTTCAGATATGGAACTGCTTTTCGATATCTTTCTGGAAA<br>CTGTGAAAGAGGCCACAGCTGGGAACCCTGGGGGCAGACAGTTAGAGAGCGGCTGACTGA<br>GCGCCTCTGTCCCCTGGGATTCCCACTCCCGGCTCTGGACTTCCACCACCACGAAAGGTTC<br>TGATCCTGGGCTCAGGGGGCCTCTCCATTGGCCAAGCTGGAGAATTTGACTACTCGGGCTCT<br>CAGGCAATTAAGGCCCTGAAGGAGGAAAACATCCAGACGTTGCTGATCAACCCCAATATTGC<br>CACAGTGCAGACCTCCCAGGGGCTGGCCGACAAGGTCTATTTTCTTCCCATAACACCTCATT<br>ATGTAACCCAGGTGATACGTAATGAACGCCCCGATGGTGTGTTACTGACTTTTGGGGCCAG<br>ACTGCTCTGAACTGTGGTGGCGGCCGCATCC |
| 8 | GST-DHOase | GCTAGAATTCGTTGGAGCTGACCAAGGCCGGGGTGCTGGCTCGGTATGGGGTCCGGGTCCT<br>GGGCACACCAGTGGAGACCATTGAGCTGACCGAGGATCGACGGGCCTTTGCTGCCAGGGAT<br>GCAGAGATCGGAGAGCATGTGGCCCCGAGCGAGGCAGCAAATTCTCTTGAACAGGCCCAGG<br>CAGCCGCTGAACGGCTGGGGTACCCTGTGCTAGTGCGTGCAGCCTTTGCCCTGGGTGGCCT<br>GGGCTCTGGCTTTGCCTCTAACAGGGAGGAGCTCTCTGCTCTCGTGGCCCCAGCTTTTGCCC<br>ATACCAGCCAAGTGTAGTAGACAAGTCTCTGAAGGGATGGAAGGAGATTGAGTACGAGGTG<br>GTGAGAGACGGCGGCCGCATCC |
| 9 | GST-ATCase | GCTAGAATTCGTCCTATGGCAACTGTGTCACGGTGTGTAACATGGAGAACTTGGACCCACTG<br>GGCATCCACACTGGTGAGTCCATAGTGGTGGCCCCTAGCCAGACACTGAATGACAGGGAGT<br>ATCAGCTCCTGAGGCAGACAGCTATCAAGGTGACCCAGCACCTGGGAATTGTTGGGGAGTG<br>CAATGTGCAGTATGCCTTGAACCCTGAGTCTGAGCAGTATTACATCATTGAAGTGAATGCCAG<br>GCTCTCTCGCAGCTCTGCCCTGGCCAGTAAGGCCACAGGTTATCCACTGGCTTATGTGGCAG<br>CCAAGCTAGCATTGGGCATCCCTTTGCCTGAGCTCAGGAACTCTGTGACAGGGGGTACAGCA<br>GCCTTTGAACCCGTGGATTATTGTGTGGTGAAGATTCCTCGATGGGACCTTAGCAAGTT<br>CCTGCGAGTCAGCACAAAGATTGGGAGCTGCATGAAGAGCGTTGGTGAAGTCATGGGCATT<br>GGGCGTTCATTTGAGGAGGCCTTCCAGAAGGCCCTGCGCATGGTGGATGAGAACTGTGTGG<br>GCTTTGATCACACAGTGAAACCAGTCAGCGATATGGAGTTGGAGACTCCAACAGATAAGCGG<br>ATTTTTGTGGTGGCAGCTGCTTTGTGGGCTGGTTATTCAGTGGACCGCCTGTATGAGCTCAC<br>ACGCATCGACCGCTGGTTCCTGCACCGAATGAAGCGTATCATCGCACATGCCCAGCTGCTAG<br>AACAACACCGTGGACAGCCTTTGCCGCCAGACCTGCTGCAACAGGCCAAGTGTCTTGGCTTC<br>TCAGACAAACAGATTGCCCTTGCAGTTCTGAGCACAGAGCTGGCTGTTCGCAAGCTGCGTCA<br>GGAACTGGGGATCTGTCCAGCAGTGAAACAGATTGACACAGTTGCAGCTGAGTGGCCAGCC<br>CAGACAAATTACCTATACCTAACGTATTGGGGCACCACCCATGACCTCACCTTTCGAACACCT<br>CATGTCCTAGTCCTTGGCTCTGGCGTCTACCGTATTGGCTCTAGCGTTGAATTTGACTGGTGT<br>GCTGTAGGCTGCATCCAGCAGCTCCGAAAGATGGGATATAAGACCATCATGGTGAACTATAA<br>CCCAGAGACAGTCAGCACCGACTATGACATGTGATCGACTCTACTTTGATGAGATCTCTTT<br>TGAGGTGGTGATGGACATCTATGAGCTCGAGAACCCTGAAGGTGTGATCCTATCCATGGGTG<br>GACAGCTGCCCAACAACATGGCCATGGCGTTGCATCGGCAGCAGTGCCGGGTGCTGGGCAC<br>CTCCCCTGAAGCCATTGACTCGGCTGAGAACCGTTTCAAGTTTTCCCGGCTCCTTGACACCA<br>TTGGTATCAGCCAGCCTCAGTGGAGGGAGCTCAGTGACCTCGAGTCTGCTCGCCAATTCTGC<br>CAGACCGTGGGGTACCCCTGTGTGGTGCGCCCCTCCTATGTGCTGAGCGGTGCTGCTATGA<br>ATGTGGCCTACACGGATGGAGACCTGGAGCGCTTCCTGAGCAGCGCAGCAGCCGTCTCCAA<br>AGAGCATCCCGTGGTCATCTCCAAGTTCATCCAGGAGGCTAAGGAGATTGACGTGGATGCCG<br>TGGCCTCTGATGGTGTGGTGGCAGCCATCGCCATCTCTGAGCATGTGGAGAATGCAGGTGT<br>GCATTCAGGTGATGCGACGCTGGTGACCCCCCCACAAGATATCACTGCCAAAACCCTGGAG<br>CGGATCAAAGCCATTGTGCATGCTGTGGGCCAGGAGCTACAGGTCACAGGACCCTTCAATCT<br>GCAGCTCATTGCCAAGGATGACCAGCTGAAAGTTATTGAATGCAACGTACGTGTCTCTCGCT<br>CCTTCCCCTTCGTTTCCAAGACACTGGGTGTGGACCTAGTAGCCTTGGCCACGCGGGTCATC<br>ATGGGGGAAGAAGTGGAACCTGTGGGGTAATGACTGGTTCTGGAGTCGTGGGAGTAAAGG<br>TGCCTCAGTTCTCCTTCTCCCGCTTGGCGGGTGCTGACGTGGTGTTGGGTGTGGAAATGACC<br>AGTACTGGGGAGGTGGCCGGCTTTGGGGAGAGCCGCTGTGAGGCATACCTCAAGGCCATG<br>CTAAGCACTGGCTTTAAGATCCCAAGAAGAATATCCTGCTGACCATTGGCAGCTATAAGAAC<br>AAAAGCGAGCTGCTCCCAACTGTGCGGCTACTGGAGAGCCTGGGCTACAGCCTCTATGCCA<br>GTCTCGGCACAGCTGACTTCTACACTGAGCATGCCGTCAAGGTAACAGCTGTGGACTGGCAC<br>TTTGAGGAGGCTGTGGATGGTGAGTGCCCACCACAGCGGAGCATCCTGGAGCAGCTAGCTG<br>AGAAAAACTTTGAGCTGGTGATTAACCTGTCAATGCGTGGAGCTGGGGCCGGCGTCTCTCT<br>TCCTTTGTCACCAAGGGCTACCGCACCCGACGCTTGGCCGCTGACTTCTCCGTGCCCCTAAT<br>CATCGATATCAAGTGCACCAAACTCTTTGTGGAGGCCCTAGGCCAGATCGGGCCAGCCCCTC<br>CTTTGAAGGTGCATGTTGACTGTATGACCTCCAAAAGCTTGTGCGACTGCCGGGATTGATT<br>GATGTCCATGTGCACCTGCGGGAACCAGGTGGGACACATAAGGAGGACTTTGCTTCAGGCA |

SEQUENCE LISTING

| SEQ ID NO. | Name | Sequence |
|---|---|---|
| | | CAGCCGCTGCCCTGGCTGGGGGTATCACCATGGTGTGTGCCATGCCTAATACCCGGCCCCC |
| | | CATCATTGACGCCCCTGCTCTGGCCCTGGCCCAGAAGCTGGCAGAGGCTGGCGCCCGGTG |
| | | CGACTTTGCGCTATTCCTTGGGGCCTCGTCTGAAAATGCAGGAACCTTGGGCACCGTGGCC |
| | | GGGTCTGCAGCCGGGCTGAAGCTTTACCTCAATGAGACCTTCTCTGAGCTGCGGCTGGACA |
| | | GCGTGGTCCAGTGGATGGAGCATTTCGAGACATGGCCCTCCCACCTCCCCATTGTGGCTCA |
| | | CGCAGAGCAGCAAACCGTGGCTGCTGTCCTCATGGTGGCTCAGCTCACTCAGCGCTCAGTG |
| | | CACATATGTCACGTGGCACGGAAGGAGGAGATCCTGCTAATTAAAGCTGCAAAGGCACGGG |
| | | GCTTGCCAGTGACCTGCGAGGTGGCTCCCCACCACCTGTTCCTAAGCCATGATGACCTGGA |
| | | GCGCCTGGGGCCTGGGAAGGGGGAGGTCCGGCCTGAGCTTGGCTCCCGCCAGGATGTGGA |
| | | AGCCCTGTGGGAGAACATGGCTGTCATCGACTGCTTTGCCTCAGACCATGCTCCCCATACCT |
| | | TGGAGGAGAAGTGTGGGTCCAGGCCCCCACCTGGGTTCCCAGGGTTAGAGACCATGCTGCC |
| | | ACTACTCCTGACGGCTGTAAGCGAGGGCCGGCTCAGCCTGGACGACCTGCTGCAGCGATTG |
| | | CACCACAATCCTCGGCGCATCTTTCACCTGCCCCCGCAGGAGGACACCTATGTGGAGGTGG |
| | | ATCTGGAGCATGAGTGGACAATTCCCAGCCACATGCCCTTCTCCAAGGCCCACTGGACACCT |
| | | TTTGAAGGGCAGAAAGTGAAGGGCACCGTCCGCCGTGTGGTCCTGCGAGGGGAGGTTGCCT |
| | | ATATCGATGGGCAGGTTCTGGTACCCCGGGCTATGGACAGGATGTACGGAAGTGGCCACA |
| | | GGGGGCTGTTCCTCAGCTCCCACCCTCAGCCCCTGCCACTAGTGAGATGACCACGACACCT |
| | | GAAAGACCCCGCCGTGGCATCCCAGGGCTTCCTGATGGCCGCTTCCATCTGCCGCCCCGAA |
| | | TCCATCGAGCCTCCGACCCAGGTTTGCCAGCTGAGGAGCAAAGGAGAAGTCCTCTCGGAA |
| | | GGTAGCCGAGCCAGAGCTGATGGGAACCCCTGATGGCACCTGCTACCCTCCACCACCAGTA |
| | | CCGAGACAGGCATCTCCCCAGAACCTGGGGACCCCTGGCTTGCTGCACCCCCCAGACCTCAC |
| | | CCCTGCTGCACTCATTAGTGGGCCAACATATCCTGTCCGTCCAGCAGTTCACCAAGGATCAG |
| | | ATGTCTCACCTGTTCAATGTGGCACACACACTGCGTATGATGGTGCAGAAGGAGCGGAGCCT |
| | | CGACATCCTGAAGGGGAAGGTCATGGCCTCCATGTTCTATGAAGTGAGCACACGGACCAGC |
| | | AGCTCCTTTGCAGCAGCCATGGCCCGGCTGGGAAGGTGCTGTGCTCAGCTTCTCGGAAGCCA |
| | | CATCGTCCGTCCAGAAGGGCGAATCCCTGGCTGACTCCGTGCAGACCATGAGCTGCTATGC |
| | | CGACGTCGTCGTGCTCCGGCACCCCCAGCCTGGAGCAGTGGAGCTGGCCGCAAGCACTG |
| | | CCGGAGGCCAGTGATCAATGCTGGGGATGGGGTCGGAGAGCACCCCACCCAGGCCCTGCT |
| | | GGACATCTTCACCATCCGTGAGGAGCTGGGAACTGTCAATGGCATGACGATCACGATGGTG |
| | | GGTGACCTGAAGCACGGACGCACAGTACATTCCCTGGCCTGCCTGCTCACCCAGTATCGTGT |
| | | CAGCCTGCGCTACGTGGCACCTCCCAGCCTGCGCATGCCACCCACTGTGCGGGCCTTCGTG |
| | | GCCTCCCGCGGCACCAAGCAGGAGGAATTCGAGAGCATTGAGGAGGCGCTGCCTGACACTG |
| | | ATGTGCTCTACATGACTCGAATCCAGAAGGAACGATTTGGCTCTACCCAGGAGTACGAAGCT |
| | | TGCTTTGGTCAGTTCATCCTCACTCCCCACATCATGACCCGGGCCAAGAAGAAGATGGTGGT |
| | | GATGCACCCGATGCCCCGTGTCAACGAGATAAGCGTGGAAGTGGACTCGGATCCCCGCGCA |
| | | GCCTACTTCCGCCAGGCTGAGAACGGCATGTACATCCGCATGGCTCTGTTAGCCACCGTGCT |
| | | GGGCCGTTTCTAGCAATTG |
| 10 | ARID1A (1-2285)-V5 (full length) | GACGGATCGGGAGATCTCCCGATCCCCTATGGTGCACTCTCAGTACAATCTGCTCTGATGCC |
| | | GCATAGTTAAGCCAGTATCTGCTCCCTGCTTGTGTGTTGGAGGTCGCTGAGTAGTGCGCGAG |
| | | CAAAATTTAAGCTACAACAAGGCAAGGCTTGACCGACAATTGCATGAAGAATCTGCTTAGGGT |
| | | TAGGCGTTTTGCGCTGCTTCGCGATGTACGGGCCAGATATACGCGTTGACATTGATTATTGA |
| | | CTAGTTATTAATAGTAATCAATTACGGGGTCATTAGTTCATAGCCCATATATGGAGTTCCGCGT |
| | | TACATAACTTACGGTAAATGGCCCGCCTGGCTGACCGCCCAACGACCCCCGCCCATTGACGT |
| | | CAATAATGACGTATGTTCCCATAGTAACGCCAATAGGGACTTTCCATTGACGTCAATGGGTGG |
| | | AGTATTTACGGTAAACTGCCCACTTGGCAGTACATCAAGTGTATCATATGCCAAGTACGCCCC |
| | | CTATTGACGTCAATGACGGTAAATGGCCCGCCTGGCATTATGCCCAGTACATGACCTTATGG |
| | | GACTTTCCTACTTGGCAGTACATCTACGTATTAGTCATCGCTATTACCATGGTGATGCGGTTTT |
| | | GGCAGTACATCAATGGGCGTGGATAGCGGTTTGACTCACGGGGATTTCCAAGTCTCCACCCC |
| | | ATTGACGTCAATGGGAGTTTGTTTTGGCACCAAAATCAACGGGACTTTCCAAAATGTCGTAAC |
| | | AACTCCGCCCCATTGACGCAAATGGGCGGTAGGCGTGTACGGTGGGAGGTCTATATAAGCA |
| | | GAGCTCTCTGGCTAACTAGAGAACCCACTGCTTACTGGCTTATCGAAATTAATACGACTCACT |
| | | ATAGGGAGACCCAAGCTGgctagcctcgagccaccATGGCCGCGCAGGTCGCCCCCGCCGCCGCC |
| | | AGCAGCCTGGGCAACCCGCCGCCGCCGCCCTCGGAGCTGAAGAAAGCCGAGCAGCAG |
| | | CAGCGGGAGGAGGCGGGGGGCGAGGCGGCGGCGGCGGCAGCGGCCGAGCGCGGGGAAA |
| | | TGAAGGCAGCCGCCGGGCAGGAAAGCGAGGGCCCCGCCGTGGGGCCGCCGCAGCCGCTG |
| | | GGAAAGGAGCTGCAGGACGGGGCCGAGAGCAATGGGGGTGGCGGCGGCGGCGGAGCCGG |
| | | CAGCGGCGGCGGGCCCGGCGCGGAGCCGGACCTGAAGAACTCGAACGGGAACGCGGGCC |
| | | CTAGGCCCGCCCTGAACAATAACCTCACGGAGCCGCCCGGCGGCGGCGGTGGCGGCAGCA |
| | | GCGATGGGTGGGGCGCCTCCTCACTCAGCCGCGGCCGCCTTGCCGCCCCCAGCCTACG |
| | | GCTTCGGGCAACCCTACGGCCGGAGCCCGTCTGCCGTCGCCGCCGCCGCGGCCGCCGTCT |
| | | TCCACCAACAACATGGCGGACAACAAAGCCCTGGCCTGGCAGCGCTGCAGAGCGGCGGCG |
| | | GCGGGGCCTGGAGCCCTACGCGGGGCCCAGCAGAACTCTCACGACCACGGCTTCCCCA |
| | | ACCACCAGTACAACTCCTACTACCCCAACCGCAGCGCCTACCCCCCGCCCGCCCCGGCCTA |
| | | CGCGCTGAGCTCCCCGAGAGGTGGCACTCCGGGCTCCGGCGCGGCGGCGGCTGCCGGCT |
| | | CCAAGCCGCCTCCCTCCTCCAGCGCCTCCGCCTCCTCGTCGTCTTCGTCCTTCGCTCAGCAG |
| | | CGCTTCGGGGCCATGGGGGGAGGCGGCCCCTTCCGCGCCGGCGGGGGAACTCCCCAGCC |
| | | CACCGCCACCCCACCCTCAACCAACTGCTCACGTCGCCCAGCCTCGGCCCCGGGGCTACCAG |
| | | GGCTACCCCGGGGGCGACTACAGTGGCGGGCCCCAGGACGGGGGCGCCGGCAAGGGCCC |
| | | GGCGGACATGGCCTCGCAGTGTTGGGGGGCTGCGGCGGCGGCAGCTGCGGCGGCGGCCG |
| | | CCTCGGGAGGGCCCAACAAAGGAGCCACCACGCGCCCATGAGCCCGGGAGCAGCGGC |
| | | GGCGGGGGCAGCCGCTCGCCCGGACCCCTCAGCCATCCAGTCCAATGGATCAGATGGGC |
| | | AAGATGAGACCTCAGCCATATGCGGGACTAACCCATACTCGCAGCAACAGGGACCTCCGT |
| | | CAGGACCGCAGCAAGGACATGGGTACCCAGGGCAGCCATACGGGTCCCAGACCCCGCAGC |

SEQUENCE LISTING

| SEQ ID NO. | Name | Sequence |
|---|---|---|
| | | GGTACCCGATGACCATGCAGGGCCGGGCGCAGAGTGCCATGGGCGGCCTCTCTTATACACA |
| | | GCAGATTCCTCCTTATGGACAACAAGGCCCCAGCGGGTATGGTCAACAGGGCCAGACTCCAT |
| | | ATTACAACCAGCAAAGTCCTCACCCTCAGCAGCAGCAGCCACCCTACTCCCAGCAACCACCG |
| | | TCCCAGACCCCTCATGCCCAACCTTCGTATCAGCAGCAGCCACAGTCTCAACCACCACAGCT |
| | | CCAGTCCTCTCAGCCTCCATACTCCCAGCAGCCATCCCAGCCTCCACATCAGCAGTCCCCGG |
| | | CTCCATACCCCTCCCAGCAGTCGACGACACAGCAGCACCCCAGAGCCAGCCCCCCTACTC |
| | | ACAGCCACAGGCTCAGTCTCCTTACCAGCAGCAGCAACCTCAGCAGCCAGCACCCTCGACG |
| | | CTCTCCCAGCAGGCTGCGTATCCTCAGCCCCAGTCTCAGCAGTCCCAGCAAACTGCCTATTC |
| | | CCAGCAGCGCTTCCCTCCACCGCAGGAGCTATCTCAAGATTCATTTGGGTCTCAGGCATCCT |
| | | CAGCCCCCTCAATGACCTCCAGTAAGGGAGGGCAAGAAGATATGAACCTGAGCCTTCAGTCA |
| | | AGACCCTCCAGCTTGCCTGATCTATCTGGTTCAATAGATGACCTCCCCATGGGGACAGAAGG |
| | | AGCTCTGAGTCCTGGAGTGAGCACATCAGGGATTTCCAGCAGCCAAGGAGAGCAGAGTAAT |
| | | CCAGCTCAGTCTCCTTTCTCCTCATACCTCCCCTCACCTGCCTGGCATCCGAGGCCCTTC |
| | | CCCGTCCCCTGTTGGCTCTCCCGCCAGTGTTGCTCAGTCTCGCTCAGGACCACTCTCGCCTG |
| | | CTGCAGTGCCAGGCAACCAGATGCCACCTCGGCCACCCAGTGGCCAGTCGGACAGCATCAT |
| | | GCATCCTTCCATGAACCAATCAAGCATTGCCCAAGATCGAGGTTATATGCAGAGGAACCCCC |
| | | AGATGCCCCAGTACAGTTCCCCCCAGCCCGGCTCAGCCTTATCTCCGCGTCAGCCTTCCGG |
| | | AGGACAGATACACACAGGCATGGGCTCCTACCAGCAGAACTCCATGGGGAGCTATGGTCCC |
| | | CAGGGGGGTCAGTATGGCCCACAAGGTGGCTACCCCAGGCAGCCAAACTATAATGCCTTGC |
| | | CCAATGCCAACTACCCCAGTGCAGGCATGGCTGGAGGCATAAACCCCATGGGTGCCGGAGG |
| | | TCAAATGCATGGACAGCCTGGCATCCCACCTTATGGCACACTCCCTCCAGGGAGGATGAGTC |
| | | ACGCCTCCATGGGCAACCGGCCTTATGGCCCTAACATGGCCAATATGCCACCTCAGGTTGG |
| | | GTCAGGGATGTGTCCCCCACCAGGGGGCATGAACCGGAAAACCCAAGAAACTGCTGTCGCC |
| | | ATGCATGTTGCTGCCAACTCTATCCAAACAGGCCGCCAGGCTACCCCAATATGAATCAAGG |
| | | GGGCATGATGGGAACTGGACCTCCTTATGGACAAGGGATTAATAGTATGGCTGGCATGATCA |
| | | ACCCTCAGGGACCCCCATATTCCATGGGTGGAACCATGGCCAACAATTCTGCAGGGATGGCA |
| | | GCCAGCCCAGAGATGATGGGCCTTGGGGATGTAAAGTTAACTCCAGCCACCAAATGAACAA |
| | | CAAGGCAGATGGGACACCCAAGACAGAATCCAAATCCAAGAAATCCAGTTCTTCTACTACAAC |
| | | CAATGAGAAGATCACCAAGTTGTATGAGCTGGGTGGTGAGCCTGAGAGGAAGATGTGGGTG |
| | | GACCGTTATCTGGCCTTCACTGAGGAGAAGGCCATGGGCATGACAAATCTGCCTGCTGTGG |
| | | GTAGGAAACCTCTGGACCTCTATCGCCTCTATGTGTCTGTGAAGGAGATTGGTGGATTGACT |
| | | CAGGTCAACAAGAACAAAAAATGGCGGGAACTTGCAACCAACCTCAATGTGGGCACATCAAG |
| | | CAGTGCTGCCAGCTCCTTGAAAAAGCAGTATATCCAGTGTCTCTATGCCTTTGAATGCAAGAT |
| | | TGAACGGGAGAAGACCCTCCCCCAGACATCTTTGCAGCTGCTGATTCCAAGAAGTCCCAGC |
| | | CCAAGATCCAGCCTCCCTCTCCTGCGGGATCAGGATCTATGCAGGGGCCCCAGACTCCCA |
| | | GTCAACCAGCAGTTCCATGGCAGAAGGAGGAGACTTAAAGCCACCAACTCCAGCATCCACAC |
| | | CACACAGTCAGATCCCCCCATTGCCAGGCATGAGCAGGAGCAATTCAGTTGGGATCCAGGAT |
| | | GCCTTTAATGATGGAAGTGACTCCACATTCCAGAAGCGGAATTCCATGACTCCAAACCCTGG |
| | | GTATCAGCCCAGTATGAATACCTCTGACATGATGGGGCGCATGTCCTATGAGCCAAATAAGG |
| | | ATCCTTATGGCAGCATGAGGAAAGCTCCAGGGAGTGATCCCTTCATGTCCTCAGGGCAGGG |
| | | CCCCAACGGCGGGATGGGTGACCCCTACAGTCGTGCTGCCGGCCCTGGGCTAGGAAATGT |
| | | GGCGATGGGACCACGACAGCACTATCCCTATGGAGGTCCTTATGACAGAGTGAGGACGGAG |
| | | CCTGGAATAGGGCCTGAGGGAAACATGAGCACTGGGGCCCCACAGCCGAATCTCATGCCTT |
| | | CCAACCCAGACTCGGGGATGTATTCTCCTAGCCGCTACCCCCGCAGCAGCAGCAGCAGCA |
| | | GCAGCAACGACATGATTCCTATGGCAATCAGTTCTCCACCCAAGGCACCCCTTCTGGCAGCC |
| | | CCTTCCCCAGCCAGCAGACTACAATGTATCAACAGCAACAGCAGAATTACAAGCGGCCAATG |
| | | GATGGCACATATGCCCTCCTGCCAAGCGGCACGAAGGGGAGATGTACAGCGTGCCATACA |
| | | GCACTGGGCAGGGCAGCCTCAGCAGCAGCAGTTGCCCCAGCCCAGCCCCAGCCTGCCA |
| | | GCCAGCAACAAGCTGCCCAGCCTTCCCCTCAGCAAGATGTATACAACCAGTATGGCAATGCC |
| | | TATCCTGCCACTGCCACAGCTGCTACTGAGCGCCGACCAGCAGGCGGCCCCCAGAACCAAT |
| | | TTCCATTCCAGTTTGGCCGAGACCGTGTCTCTGCACCCCCTGGCACCAATGCCCAGCAAAAC |
| | | ATGCCACCACAAATGATGGGCGGCCCCATACAGGCATCAGCTGAGGTTGCTCAGCAAGGCA |
| | | CCATGTGGCAGGGGCGTAATGACATGACCTATAATTATGCCAACAGGCAGAGCACGGGCTCT |
| | | GCCCCCCAGGGCCCGCCTATCATGGCGTGAACCGAACAGATGAAATGCTGCACACAGATC |
| | | AGAGGGCCAACCACGAAGGCTCGTGGCCTTCCCATGGCACACGCCAGCCCCCATATGGTCC |
| | | CTCTGCCCCTGTGCCCCCCATGACAAGGCCCCCTCCATCTAACTACCAGCCCCCACCAAGCA |
| | | TGCAGAATCACATTCCTCAGGTATCCAGCCCTGCTCCCCTGCCCCGGCCAATGGAGAACCGC |
| | | ACCTCTCCTAGCAAGTCTCCATTCCTGCACTCTGGGATGAAAATGCAGAAGGCAGGTCCCCC |
| | | AGTACCTGCCTCGCACATAGCACCTGCCCCTGTGCAGCCCCCCATGATTCGGCGGGATATCA |
| | | CCTTCCCACCTGGCTCTGTTGAAGCCACACAGCCTGTGTTGAAGCAGAGGAGGCGGCTCAC |
| | | AATGAAAGACATTGGAACCCCGGAGGCATGGCGGGTAATGATGTCCCTCAAGTCTGGTCTCC |
| | | TGGCAGAGAGCACATGGGCATTAGATACCATCAACATCCTGCTGTATGATGACAACAGCATC |
| | | ATGACCTTCAACCTCAGTCAGCTCCCAGGGTTGCTAGAGCTCCTTGTAGAATATTTCCGACGA |
| | | TGCCTGATTGAGATCTTTGGCATTTTAAAGGAGTATGAGGTGGGTGACCCAGGACAGGAAAC |
| | | GCTACTGGATCCTGGGAGGTTCAGCAAGGTGTCTAGTCCAGCTCCCATGGAGGGTGGGGAA |
| | | GAAGAAGAAGAACTTCTAGGTCCTAAACTAGAAGAGGAAGAAGAAGAGGAAGTAGTTGAAAA |
| | | TGATGAGGAGATAGCCTTTTCAGGCAAGGACAAGCCAGCTTCAGAGAATAGTGAGGAGAAGC |
| | | TGATCAGTAAGTTTGACAAGCTTCCAGTAAAGATCGTACAGAAGAATGATCCATTTGTGGTGG |
| | | ACTGCTCAGATAAGCTTGGGCGTGTGCAGGAGTTTGACAGTGGCCTGCTGCACTGGCGGAT |
| | | TGGTGGGGGGACACCACTGAGCATATCCAGACCCACTTCGAGAGCAAGACAGAGCTGCTG |
| | | CCTTCCCGGCCTCACGCACCCTGCCCACCAGCCCCTCGGAAGCATGTGACAACAGCAGAGG |
| | | GTACACCAGGGACAACAGACCAGGAGGGGCCCCCACCTGATGGACCTCCAGAAAAACGGAT |
| | | CACAGCCACTATGGATGACATGTTGTCTACTCGGTCTAGCACCTTGACCGAGGATGGAGCTA |
| | | AGAGTTCAGAGGCCATCAAGGAGAGCAGCAAGTTTCCATTTGGCATTAGCCCAGCACAGAGC |

SEQUENCE LISTING

| SEQ ID NO. | Name | Sequence |
|---|---|---|
| | | CACCGGAACATCAAGATCCTAGAGGACGAACCCCACAGTAAGGATGAGACCCCACTGTGTAC
CCTTCTGGACTGGCAGGATTCTCTTGCCAAGCGCTGCGTCTGTGTGTCCAATACCATTCGAA
GCCTGTCATTTGTGCCAGGCAATGACTTTGAGATGTCCAAACACCCAGGGCTGCTGCTCATC
CTGGGCAAGCTGATCCTGCTGCACCACAAGCACCCAGAACGGAAGCAGGCACCACTAACTT
ATGAAAAGGAGGAGGAACAGGACCAAGGGGTGAGCTGCAACAAAGTGGAGTGGTGGTGGG
ACTGCTTGGAGATGCTCCGGGAAAACACCTTGGTTACACTCGCCAACATCTCGGGGCAGTTG
GACCTATCTCCATACCCCGAGAGCATTTGCCTGCCTGTCCTGGACGGACTCCTACACTGGGC
AGTTTGCCCTTCAGCTGAAGCCCAGGACCCCTTTTCCACCCTGGGCCCCAATGCCGTCCTTT
CCCCGCAGAGACTGGTCTTGGAAACCCTCAGCAAACTCAGCATCCAGGACAACAATGTGGAC
CTGATTCTGGCCACACCCCCCTTCAGCCGCCTGGAGAAGTTGTATAGCACTATGGTGCGCTT
CCTCAGTGACCGAAAGAACCCGGTGTGCCGGGAGATGGCTGTGGTACTGCTGGCCAACCTG
GCTCAGGGGACAGCCTGGCAGCTCGTGCCATTGCAGTGCAGAAGGGCAGTATCGGCAACC
TCCTGGGCTTCCTAGAGGACAGCCTTGCCGCCACACAGTTCCAGCAGAGCCAGGCCAGCCT
CCTCCACATGCAGAACCCACCCTTTGAGCCAACTAGTGTGGACATGATGCGGCGGGCTGCC
CGCGCGCTGCTTGCCTTGGCCAAGGTGGACGAGAACCACTCAGAGTTTACTCTGTACGAATC
ACGGCTGTTGGACATCTCGGTATCACCGTTGATGAACTCATTGGTTTCACAAGTCATTTGTGA
TGTACTGTTTTTGATTGGCCAGTCCTCGAGTCTAGAGGGCCCGCGGTTCGAAGGTAAGCCTA
TCCCTAACCCTCTCCTCGGTCTCGATTCTACGCGTACCGGTCATCATCACCATCACCATTGAgt
ttaaacCCGCTGATCAGCCTCGACTGTGCCTTCTAGTTGCCAGCCATCTGTTGTTTGCCCCTCC
CCCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTCTATGG
CTTCTGAGGCGGAAAGAACCAGCTGGGGCTCTAGGGGGTATCCCCACGCGCCCTGTAGCGG
CGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGT
CAAGCTCTAAATCGGGGGCTCCCTTTAGGGTTCCGATTTAGTGCTTTACGGCACCTCGACCC
CAAAAAACTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAACAACAC
TCAACCCTATCTCGGTCTATTCTTTTGATTTATAAGGGATTTTGCCGATTTCGGCCTATTGTT
AAAAAAATGAGCTGATTTAACAAAAATTTAACGCGAATTAATTCTGTGGAATGTGTGTCAGTTAG
GGTGTGGAAAGTCCCCAGGCTCCCCAGCAGGCAGAAGTATGCAAAGCATGCATCTCAATTAG
TCAGCAACCAGGTGTGGAAAGTCCCCAGGCTCCCCAGCAGGCAGAAGTATGCAAAGCATGC
ATCTCAATTAGTCAGCAACCATAGTCCCGCCCCTAACTCCGCCCATCCCGCCCCTAACTCCG
CCCAGTTCCGCCCATTCTCCGCCCCATGGCTGACTAATTTTTTTTATTTATGCAGAGGCCGAG
GCCGCCTCTGCCTCTGAGCTATTCCAGAAGTAGTGAGGAGGCTTTTTTGGAGGCCTAGGCTT
TTGCAAAAAGCTCCCGGGAGCTTGTATATCCATTTTCGGATCTGATCAGCACGTGTTGACAAT
TAATCATCGGCATAGTATATCGGCATAGTATAATACGACAAGGTGAGGAACTAAACCATGGCC
AAGCCTTTGTCTCAAGAAGAATCCACCCTCATTGAAAGAGCAACGGCTACAATCAACAGCATC
CCCATCTCTGAAGACTACAGCGTCGCCAGCGCAGCTCTCTCTAGCGACGGCCGCATCTTCAC
TGGTGTCAATGTATATCATTTTACTGGGGGACCTTGTGCAGAACTCGTGGTGCTGGGCACTG
CTGCTGCTGCGGCAGCTGGCAACCTGACTTGTATCGTCGCGATCGGAAATGAGAACAGGGG
CATCTTGAGCCCCTGCGGACGGTGCCGACAGGTGCTTCTCGATCTGCATCCTGGGATCAAA
GCCATAGTGAAGGACAGTGATGGACAGCCGACGGCAGTTGGGATTCGTGAATTGCTGCCCT
CTGGTTATGTGTGGGAGGGCTAAGCACTTCGTGGCCGAGGAGCAGGACTGACACGTGCTAC
GAGATTTCGATTCCACCGCCGCCTTCTATGAAAGGTTGGGCTTCGGAATCGTTTTCCGGGAC
GCCGGCTGGATGATCCTCAGCGCGGGGATCTCATGCTGGAGTTCTTCGCCCACCCCAACT
TGTTTATTGCAGCTTATAATGGTTACAAATAAAGCAATAGCATCACAAATTTCACAAATAAAGC
ATTTTTTTCACTGCATTCTAGTTGTGGTTTGTCCAAACTCATCAATGTATCTTATCATGTCTGTA
TACCGTCGACCTCTAGCTAGAGCTTGGCGTAATCATGGTCATAGCTGTTTCCTGTGTGAAATT
GTTATCCGCTCACAATTCCACACAACATACGAGCCGGAAGCATAAAGTGTAAAGCCTGGGGT
GCCTAATGAGTGAGCTAACTCACATTAATTGCGTTGCGCTCACTGCCCGCTTTCCAGTCGGG
AAACCTGTCGTGCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCAGGGGATAACGCA
GGAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGGCCTAACTA
CGGCTACACTAGAAGAACAGTATTTGGTATCTGCGCTCTGCTGAAGCCAGTTACCTTCGGAA
AAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGG
GGTCTGACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTA
CCATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAG |

SEQUENCE LISTING

| SEQ ID NO. | Name | Sequence |
|---|---|---|
| | | CGGTTAGCTCCTTCGGTCCTCCGATCGTTGTCAGAAGTAAGTTGGCCGCAGTGTTATCACTC |
| | | ATGGTTATGGCAGCACTGCATAATTCTCTTACTGTCATGCCATCCGTAAGATGCTTTTCTGTG |
| | | ACTGGTGAGTACTCAACCAAGTCATTCTGAGAATAGTGTATGCGGCGACCGAGTTGCTCTTG |
| | | CCCGGCGTCAATACGGGATAATACCGCGCCACATAGCAGAACTTTAAAAGTGCTCATCATTG |
| | | GAAAACGTTCTTCGGGGCGAAAACTCTCAAGGATCTTACCGCTGTTGAGATCCAGTTCGATG |
| | | TAACCCACTCGTGCACCCAACTGATCTTCAGCATCTTTTACTTTCACCAGCGTTTCTGGGTGA |
| | | GCAAAAACAGGAAGGCAAATGCCGCAAAAAAGGGAATAAGGGCGACACGGAAATGTTGAAT |
| | | ACTCATACTCTTCCTTTTTCAATATTATTGAAGCATTTATCAGGGTTATTGTCTCATGAGCGGA |
| | | TACATATTTGAATGTATTTAGAAAAATAAACAAATAGGGGTTCCGCGCACATTTCCCCGAAAAG |
| | | TGCCACCTGACGTC |
| 11 | ARID1A (1-1758)-V5 (N-terminal) | GACGGATCGGGAGATCTCCCGATCCCCTATGGTGCACTCTCAGTACAATCTGCTCTGATGCC |
| | | GCATAGTTAAGCCAGTATCTGCTCCCTGCTTGTGTGTTGGAGGTCGCTGAGTAGTGCGCGAG |
| | | CAAAATTTAAGCTACAACAAGGCAAGGCTTGACCGACAATTGCATGAAGAATCTGCTTAGGGT |
| | | TAGGCGTTTTGCGCTGCTTCGCGATGTACGGGCCAGATATACGCGTTGACATTGATTATTGA |
| | | CTAGTTATTAATAGTAATCAATTACGGGGTCATTAGTTCATAGCCCATATATGGAGTTCCGCGT |
| | | TACATAACTTACGGTAAATGGCCCGCCTGGCTGACCGCCAACGACCCCCGCCCATTGACGT |
| | | CAATAATGACGTATGTTCCCATAGTAACGCCAATAGGGACTTTCCATTGACGTCAATGGGTGG |
| | | AGTATTTACGGTAAACTGCCCACTTGGCAGTACATCAAGTGTATCATATGCCAAGTACGCCCC |
| | | CTATTGACGTCAATGACGGTAAATGGCCCGCCTGGCATTATGCCCAGTACATGACCTTATGG |
| | | GACTTTCCTACTTGGCAGTACATCTACGTATTAGTCATCGCTATTACCATGGTGATGCGGTTTT |
| | | GGCAGTACATCAATGGGCGTGGATAGCGGTTTGACTCACGGGGATTTCCAAGTCTCCACCCC |
| | | ATTGACGTCAATGGGAGTTTGTTTTGGCACCAAAATCAACGGGACTTTCCAAAATGTCGTAAC |
| | | AACTCCGCCCCATTGACGCAAATGGGCGGTAGGCGTGTACGGTGGGAGGTCTATATAAGCA |
| | | GAGCTCTCTGGCTAACTAGAGAACCCACTGCTTACTGGCTTATCGAAATTAATACGACTCACT |
| | | ATAGGGAGACCCAAGCTGgctagcctcgagccaccATGGCCGCGCAGGTCGCCCCCGCCGCCGCC |
| | | AGCAGCCTGGGCAACCCGCCGCCGCCGCCCTCGAGCTGAAGAAAGCCGAGCAGCAG |
| | | CAGCGGGAGGAGCGGGGGGCGAGGCGGCGGCGGCGGCAGCGGCCGAGCGCGGGGAAA |
| | | TGAAGGCAGCCGCCGGGCAGGAAAGCGAGGGCCCCGCCGTGGGGCGCCGCAGCCGCTG |
| | | GGAAAGGAGCTGCAGGACGGGGCCGAGAGCAATGGGGGTGGCGGCGGCGGCGGAGCCGG |
| | | CAGCGGCGGCGGGCCCGGCGCGGAGCCGGACCTGAAGAACTCGAACGGGAACGCGGGCC |
| | | CTAGGCCCGCCCTGAACAATAACCTCACGGAGCCGCCCGGCGGCGGCGGTGGCGGCAGCA |
| | | GCGATGGGGTGGGGGCGCCTCCTCACTCAGCCGCGGCCGCCTTGCCGCCCCCAGCCTACG |
| | | GCTTCGGGCAACCCTACGGCCGGAGCCCGTCTGCCGTCGCCGCCGCCGCGGCCGCCGTCT |
| | | TCCACCAACAACATGGCGGACAACAAAGCCCTGGCCTGGCAGCGCTGCAGAGCGGCGGCG |
| | | GCGGGGGCCTGGAGCCCTACGGGGGCCCAGCAGAACTCTCACGACCACGGCTTCCCCA |
| | | ACCACCAGTACAACTCCTACTACCCCAACCGCAGCGCCTACCCCCCGCCCGCCCCCGGCCTA |
| | | CGCGCTGAGCTCCCCGAGAGGTGGCACTCCGGGCTCCGGCGCGGCGGCGGCTGCCGGCT |
| | | CCAAGCCGCCTCCTCCTCCAGCGCCTCCGCCTCCTCGTCGTCTTCGTCCTTCGCTCAGCAG |
| | | CGCTTCGGGGCATGGGGGGAGGCGGCCCCTCCGCGGCCGGCGGGGGAACTCCCCAGCC |
| | | CACCGCCACCCCCACCCTCAACCAACTGCTCACGTCGCCCAGCTCGGCCCGGGGCTACCAG |
| | | GGCTACCCCGGGGGCGACTACAGTGGCGGGCCCCAGGACGGGGGCGCCGGCAAGGGCCC |
| | | GGCGGACATGGCCTCGCAGTGTTGGGGGGCTGCGGCGGCGGCAGCTGCGGCGGCGGCCG |
| | | CCTCGGGAGGGGCCCAACAAAGGAGCCACCACGCGCCCATGAGCCCCGGGAGCAGCGGC |
| | | GGCGGGGGGCAGCCGCTCGCCCGGACCCCTCAGCCATCCAGTCCAATGGATCAGATGGGC |
| | | AAGATGAGACCTCAGCCATATGCGGGACTAACCCATACTCGCAGCAACAGGGACCTCCGT |
| | | CAGGACCGCAGCAAGGACATGGGTACCCAGGGCAGCCATACGGGTCCCAGACCCCGCAGC |
| | | GGTACCCGATGACCATGCAGGGCCGGGCGCAGAGTGCCATGGGCGGCCTCTCTTATACACA |
| | | GCAGATTCCTCCTTATGGACAACAAGGCCCCAGCGGGTATGGTCAACAGGGCCAGACTCCAT |
| | | ATTACAACCAGCAAAGTCCTCACCCTCAGCAGCAGCAGCCCCACCCTACTCCCAGCAACCACCG |
| | | TCCCAGACCCCTCATGCCCAACCTTCGTATCAGCAGCAGCCACAGTCTCAACCACCACAGCT |
| | | CCAGTCCTCTCAGCCTCCATACTCCCAGCAGCCATCCCAGCCTCCACATCAGCAGTCCCCGG |
| | | CTCCATACCCCTCCCAGCAGTCGACGACACAGCAGCACCCCCAGAGCCAGCCCCCCTACTC |
| | | ACAGCCACAGGCTCAGTCTCCTTACCAGCAGCAGCAACCTCAGCAGCCAGCACCCCTCGACG |
| | | CTCTCCCAGCAGGCTGCGTATCCTCAGCCCCAGTCTCAGCAGAGTCTAGAGGGCCCGCGGT |
| | | TCGAAGGTAAGCCTATCCCTAACCCTCTCCTCGGTCTCGATTCTACGCGTACCGGTCATCATC |
| | | ACCATCACCATTGAgtttaaacCCGCTGATCAGCCTCGACTGTGCCTTCTAGTTGCCAGCCATCT |
| | | GTTGTTTGCCCCTCCCCCGTGCCTTCCTTGACCCTGGAAGGTGCCACTCCCACTGTCCTTTC |
| | | CTAATAAAATGAGGAAATTGCATCGCATTGTCTGAGTAGGTGTCATTCTATTCTGGGGGGTGG |
| | | GGTGGGGCAGGACAGCAAGGGGGAGGATTGGGAAGACAATAGCAGGCATGCTGGGGATGC |
| | | GGTGGGCTCTATGGCTTCTGAGGCGGAAAGAACCAGCTGGGGCTCTAGGGGGTATCCCCAC |
| | | GCGCCCTGTAGCGGCGCATTAAGCGCGGCGGGTGTGGTGGTTACGCGCAGCGTGACCGCT |
| | | ACACTTGCCAGCGCCCTAGCGCCCGCTCCTTTCGCTTTCTTCCCTTCCTTTCTCGCCACGTTC |
| | | GCCGGCTTTCCCCGTCAAGCTCTAAATCGGGGCTCCCTTTAGGGTTCCGATTTAGTGCTTT |
| | | ACGGCACCTCGACCCCAAAAAACTTGATTAGGGTGATGGTTCACGTAGTGGGCCATCGCCCT |
| | | GATAGACGGTTTTTCGCCCTTTGACGTTGGAGTCCACGTTCTTTAATAGTGGACTCTTGTTCC |
| | | AAACTGGAACAACACTCAACCCTATCTCGGTCTATTCTTTTGATTTATAAGGGATTTTGCCGAT |
| | | TTCGGCCTATTGGTTAAAAAATGAGCTGATTTAACAAAAATTTAACGCGAATTAATTCTGTGGA |
| | | ATGTGTGTCAGTTAGGGTGTGGAAAGTCCCCAGGCTCCCCAGCAGGCAGAAGTATGCAAAG |
| | | CATGCATCTCAATTAGTCAGCAACCAGGTGTGGAAAGTCCCCAGGCTCCCCAGCAGGCAGAA |
| | | GTATGCAAAGCATGCATCTCAATTAGTCAGCAACCATAGTCCCGCCCCTAACTCCGCCCATC |
| | | CCGCCCCTAACTCCGCCCAGTTCCGCCCATTCTCCGCCCCATGGCTGACTAATTTTTTTATT |
| | | TATGCAGAGGCCGAGGCCGCCTCTGCCTCTGAGCTATTCCAGAAGTAGTGAGGAGGCTTTTT |
| | | TGGAGGCCTAGGCTTTTGCAAAAAGCTCCCGGGAGCTTGTATATCCATTTTCGGATCTGATCA |

SEQUENCE LISTING

| SEQ ID NO. | Name | Sequence |
|---|---|---|
| | | GCACGTGTTGACAATTAATCATCGGCATAGTATATCGGCATAGTATAATACGACAAGGTGAGG<br>AACTAAACCATGGCCAAGCCTTTGTCTCAAGAAGAATCCACCCTCATTGAAAGAGCAACGGCT<br>ACAATCAACAGCATCCCCATCTCTGAAGACTACAGCGTCGCCAGCGCAGCTCTCTCTAGCGA<br>CGGCCGCATCTTCACTGGTGTCAATGTATATCATTTTACTGGGGGACCTTGTGCAGAACTCGT<br>GGTGCTGGGCACTGCTGCTGCTGCGGCAGCTGGCAACCTGACTTGTATCGTCGCGATCGGA<br>AATGAGAACAGGGGCATCTTGAGCCCCTGCGGACGGTGCCGACAGGTGCTTCTCGATCTGC<br>ATCCTGGGATCAAAGCCATAGTGAAGGACAGTGATGGACAGCCGACGGCAGTTGGGATTCG<br>TGAATTGCTGCCCTCTGGTTATGTGTGGGAGGGCTAAGCACTTCGTGGCCGAGGAGCAGGA<br>CTGACACGTGCTACGAGATTTCGATTCCACCGCCGCCTTCTATGAAAGGTTGGGCTTCGGAA<br>TCGTTTTCCGGGACGCCGGCTGGATGATCCTCCAGCGCGGGGATCTCATGCTGGAGTTCTT<br>CGCCCACCCCAACTTGTTTATTGCAGCTTATAATGGTTACAAATAAAGCAATAGCATCACAAAT<br>TTCACAAATAAAGCATTTTTTTCACTGCATTCTAGTTGTGGTTTGTCCAAACTCATCAATGTATC<br>TTATCATGTCTGTATACCGTCGACCTCTAGCTAGAGCTTGGCGTAATCATGGTCATAGCTGTT<br>TCCTGTGTGAAATTGTTATCCGCTCACAATTCCACACAACATACGAGCCGGAAGCATAAAGTG<br>TAAAGCCTGGGGTGCCTAATGAGTGAGCTAACTCACATTAATTGCGTTGCGCTCACTGCCCG<br>CTTTCCAGTCGGGAAACCTGTCGTGCCAGCTGCATTAATGAATCGGCCAACGCGCGGGGAG<br>AGGCGGTTTGCGTATTGGGCGCTCTTCCGCTTCCTCGCTCACTGACTCGCTGCGCTCGGTC<br>GTTCGGCTGCGGCGAGCGGTATCAGCTCACTCAAAGGCGGTAATACGGTTATCCACAGAATC<br>AGGGGATAACGCAGGAAAGAACATGTGAGCAAAAGGCCAGCAAAAGGCCAGGAACCGTAAA<br>AAGGCCGCGTTGCTGGCGTTTTTCCATAGGCTCCGCCCCCTGACGAGCATCACAAAAATCG<br>ACGCTCAAGTCAGAGGTGGCGAAACCCGACAGGACTATAAAGATACCAGGCGTTTCCCCCTG<br>GAAGCTCCCTCGTGCGCTCTCCTGTTCCGACCCTGCCGCTTACCGGATACCTGTCCGCCTTT<br>CTCCCTTCGGGAAGCGTGGCGCTTTCTCATAGCTCACGCTGTAGGTATCTCAGTTCGGTGTA<br>GGTCGTTCGCTCCAAGCTGGGCTGTGTGCACGAACCCCCCGTTCAGCCCGACCGCTGCGCC<br>TTATCCGGTAACTATCGTCTTGAGTCCAACCCGGTAAGACACGACTTATCGCCACTGGCAGC<br>AGCCACTGGTAACAGGATTAGCAGAGCGAGGTATGTAGGCGGTGCTACAGAGTTCTTGAAGT<br>GGTGGCCTAACTACGGCTACACTAGAAGAACAGTATTTGGTATCTGCGCTCTGCTGAAGCCA<br>GTTACCTTCGGAAAAAGAGTTGGTAGCTCTTGATCCGGCAAACAAACCACCGCTGGTAGCGG<br>TGGTTTTTTTGTTTGCAAGCAGCAGATTACGCGCAGAAAAAAAGGATCTCAAGAAGATCCTTT<br>GATCTTTTCTACGGGGTCTGACGCTCAGTGGAACGAAAACTCACGTTAAGGGATTTTGGTCAT<br>GAGATTATCAAAAAGGATCTTCACCTAGATCCTTTTAAATTAAAAATGAAGTTTTAAATCAATCT<br>AAAGTATATATGAGTAAACTTGGTCTGACAGTTACCAATGCTTAATCAGTGAGGCACCTATCT<br>CAGCGATCTGTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCACGCTCACC<br>GGCTCCAGATTTATCAGCAATAAACCAGCCAGCCGGAAGGGCCGAGCGCAGAAGTGGTCCT<br>GCAACTTTATCCGCCTCCATCCAGTCTATTAATTGTTGCCGGGAAGCTAGAGTAAGTAGTTCG<br>CCAGTTAATAGTTTGCGCAACGTTGTTGCCATTGCTACAGGCATCGTGGTGTCACGCTCGTC<br>GTTTGGTATGGCTTCATTCAGCTCCGGTTCCCAACGATCAAGGCGAGTTACATGATCCCCCAT<br>GTTGTGCAAAAAAGCGGTTAGCTCCTTCGGTCCTCCGATCGTTGTCAGAAGTAAGTTGGCCG<br>CAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGAC<br>CGAGTTGCTCTTGCCCGGCGTCAATACGGGATAATACCGCGCCACATAGCAGAACTTTAAA<br>GTGCTCATCATTGGAAAACGTTCTTCGGGGCGAAAACTCTCAAGGATCTTACCGCTGTTGAG<br>ATCCAGTTCGATGTAACCCACTCGTGCACCCAACTGATCTTCAGCATCTTTTACTTTCACCAG<br>CGTTTCTGGGTGAGCAAAAACAGGAAGGCAAAATGCCGCAAAAAAGGGAATAAGGGCGACA<br>CGGAAATGTTGAATACTCATACTCTTCCTTTTTCAATATTATTGAAGCATTTATCAGGGTTATTG<br>TCTCATGAGCGGATACATATTTGAATGTATTTAGAAAAATAAACAAATAGGGGTTCCGCGCAC<br>ATTTCCCCGAAAAGTGCCACCTGACGTC |
| 12 | ARID1A (1759-2285)-V5 (C-terminal) | GACGGATCGGGAGATCTCCCGATCCCCTATGGTGCACTCTCAGTACAATCTGCTCTGATGCC<br>GCATAGTTAAGCCAGTATCTGCTCCCTGCTTGTGTGTTGGAGGTCGCTGAGTAGTGCGCGAG<br>CAAAATTTAAGCTACAACAAGGCAAGGCTTGACCGACAATTGCATGAAGAATCTGCTTAGGGT<br>TAGGCGTTTTGCGCTGCTTCGCGATGTACGGGCCAGATATACGCGTTGACATTGATTATTGA<br>CTAGTTATTAATAGTAATCAATTACGGGGTCATTAGTTCATAGCCCATATATGGAGTTCCGCGT<br>TACATAACTTACGGTAAATGGCCCGCCTGGCTGACCGCCCAACGACCCCCGCCCATTGACGT<br>CAATAATGACGTATGTTCCCATAGTAACGCCAATAGGGACTTTCCATTGACGTCAATGGGTGG<br>AGTATTTACGGTAAACTGCCCACTTGGCAGTACATCAAGTGTATCATATGCCAAGTACGCCCC<br>CTATTGACGTCAATGACGGTAAATGGCCCGCCTGGCATTATGCCCAGTACATGACCTTATGG<br>GACTTTCCTACTTGGCAGTACATCTACGTATTAGTCATCGCTATTACCATGGTGATGCGGTTTT<br>GGCAGTACATCAATGGGCGTGGATAGCGGTTTGACTCACGGGGATTTCCAAGTCTCCACCCC<br>ATTGACGTCAATGGGAGTTTGTTTTGGCACCAAAATCAACGGGACTTTCCAAAATGTCGTAAC<br>AACTCCGCCCCATTGACGCAAATGGGCGGTAGGCGTGTACGGTGGGAGGTCTATATAAGCA<br>GAGCTCTCTGGCTAACTAGAGAACCCACTGCTTACTGGCTTATCGAAATTAATACGACTCACT<br>ATAGGGAGACCCAAGCTGgctagcctcgagccaccATGTCCCAGCAAACTGCCTATTCCCAGCAGCG<br>CTTCCCTCCACCGCAGGAGCTATCTCAAGATTCATTTGGGTCTCAGGCATCCTCAGCCCCCT<br>CAATGACCTCCAGTAAGGGAGGGCAAGAAGATATGAACCTGAGCCTTCAGTCAAGACCCTCC<br>AGCTTGCCTGATCTATCTGGTTCAATAGATGACCTCCCCATGGGGACAGAAGGAGCTCTGAG<br>TCCTGGAGTGAGCACATCAGGGATTTCCAGCAGCCAAGGAGAGCAGAGTAATCCAGCTCAGT<br>CTCCCTTTCTCTCCTCATACCTCCCCTCACCTGCCTGGCATCCGAGGCCCTTCCCCGTCCCCT<br>GTTGGCTCTCCCGCCAGTGTTGCTCAGTCTCGCTCAGGACCACTCTCGCCTGCTGCAGTGCC<br>AGGCAACCAGATGCCACCTCGGCCACCCAGTGGCCAGTCGGACAGCATCATGCATCCTTCC<br>ATGAACCAATCAAGCATTGCCCAAGATCGAGGTTATATGCAGAGGAACCCCCAGATGCCCCA<br>GTACAGTTCCCCCCAGCCCGGCTCAGCCTTATCTCCGCGTCAGCCTTCCGGAGGACAGATA<br>CACACAGGCATGGGCTCCTACCAGCAGAACTCCATGGGGAGCTATGGTCCCCAGGGGGGTC |

-continued

SEQUENCE LISTING

| SEQ ID NO. | Name | Sequence |
|---|---|---|
| | | AGTATGGCCCACAAGGTGGCTACCCCAGGCAGCCAAACTATAATGCCTTGCCCAATGCCAAC |
| | | TACCCCAGTGCAGGCATGGCTGGAGGCATAAACCCCATGGGTGCCGGAGGTCAAATGCATG |
| | | GACAGCCTGGCATCCCACCTTATGGCACACTCCCTCCAGGGAGGATGAGTCACGCCTCCAT |
| | | GGGCAACCGGCCTTATGGCCCTAACATGGCCAATATGCCACCTCAGGTTGGGTCAGGGATG |
| | | TGTCCCCCACCAGGGGGCATGAACCGGAAAACCCAAGAAACTGCTGTCGCCATGCATGTTG |
| | | CTGCCAACTCTATCCAAAACAGGCCGCCAGGCTACCCCAATATGAATCAAGGGGCATGATG |
| | | GGAACTGGACCTCCTTATGGACAAGGGATTAATAGTATGGCTGGCATGATCAACCCTCAGGG |
| | | ACCCCCATATTCCATGGGTGGAACCATGGCCAACAATTCTGCAGGGATGGCAGCCAGCCCA |
| | | GAGATGATGGGCCTTGGGGATGTAAAGTTAACTCCAGCCACCAAAATGAACAACAAGGCAGA |
| | | TGGGACACCCAAGACAGAATCCAAATCCAAGAAATCCAGTTCTTCTACTACAACCAATGAGAA |
| | | GATCACCAAGTTGTATGAGCTGGGTGGTGAGCCTGAGAGGAAGATGTGGGTGGACCGTTAT |
| | | CTGGCCTTCACTGAGGAGAAGGCCATGGGCATGACAAATCTGCCTGCTGTGGGTAGGAAAC |
| | | CTCTGGACCTCTATCGCCTCTATGTGTCTGTGAAGGAGATTGGTGGATTGACTCAGGTCAAC |
| | | AAGAACAAAAAATGGCGGGAACTTGCAACCAACCTCAATGTGGGCACATCAAGCAGTGCTGC |
| | | CAGCTCCTTGAAAAAGCAGTATATCCAGTGTCTCTATGCCTTTGAATGCAAGATTGAACGGGG |
| | | AGAAGACCCTCCCCCAGACATCTTTGCAGCTGCTGATTCCAAGAAGTCCCAGCCCAAGATCC |
| | | AGCCTCCCTCTCCTGCGGGATCAGGATCTATGCAGGGGCCCCAGACTCCCCAGTCAACCAG |
| | | CAGTTCCATGGCAGAAGGAGGAGACTTAAAGCCACCAACTCCCAGCATCCACACCACACAGTC |
| | | AGATCCCCCCATTGCCAGGCATGAGCAGGAGCAATTCAGTTGGGATCCAGGATGCCTTTAAT |
| | | GATGGAAGTGACTCCACATTCCAGAAGCGGAATTCCATGACTCCAAACCCTGGGTATCAGCC |
| | | CAGTATGAATACCTCTGACATGATGGGGCGCATGTCCTATGAGCCAAATAAGGATCCTTATG |
| | | GCAGCATGAGGAAAGCTCCAGGGAGTGATCCCTTCATGTCCTCAGGGCAGGGCCCCAACGG |
| | | CGGGATGGGTGACCCCTACAGTCGTGCTGCCGGCCCTGGGCTAGGAAATGTGGCGATGGG |
| | | ACCACGACAGCACTATCCCTATGGAGGTCCTTATGACAGAGTGAGGACGGAGCCTGGAATAG |
| | | GGCCTGAGGGAAACATGAGCACTGGGGCCCCACAGCCGAATCTCATGCCTTCCAACCCAGA |
| | | CTCGGGGATGTATTCTCCTAGCCGCTACCCCCGCAGCAGCAGCAGCAGCAGCAACGA |
| | | CATGATTCCTATGGCAATCAGTTCTCCACCCAAGGCACCCCTTCTGGCAGCCCCTTCCCCAG |
| | | CCAGCAGACTACAATGTATCAACAGCAACAGCAGAATTACAAGCGGCCAATGGATGGCACAT |
| | | ATGGCCCTCCTGCCAAGCGGCACGAAGGGGAGATGTACAGCGTGCCATACAGCACTGGGCA |
| | | GGGGCAGCCTCAGCAGCAGCAGTTGCCCCCAGCCCAGCCCCAGCCTGCCAGCCAGCAACA |
| | | AGCTGCCCAGCCTTCCCCTCAGCAAGATGTATACAACCAGTATGGCAATGCCTATCCTGCCA |
| | | CTGCCACAGCTGCTACTGAGCGCCGACCAGCAGGCGGCCCCCAGAACCAATTTCCATTCCA |
| | | GTTTGGCCGAGACCGTGTCTCTGCACCCCCTGGCACCAATGCCCAGCAAAACATGCCACCA |
| | | CAAATGATGGGCGGCCCCATACAGGCATCAGCTGAGGTTGCTCAGCAAGGCACCATGTGGC |
| | | AGGGGCGTAATGACATGACCTATAATTATGCCAACAGGCAGAGCACGGGCTCTGCCCCCCA |
| | | GGGCCCCGCCTATCATGGCGTGAACCGAACAGATGAAATGCTGCACACAGATCAGAGGGCC |
| | | AACCACGAAGGCTCGTGGCCTTCCCATGGCACACGCCAGCCCCCATATGGTCCCTCTGCCC |
| | | CTGTGCCCCCCATGACAAGGCCCCCTCCATCTAACTACCAGCCCCCACCAAGCATGCAGAAT |
| | | CACATTCCTCAGGTATCCAGCCCTGCTCCCCTGCCCCGGCCAATGGAGAACCGCACCTCTCC |
| | | TAGCAAGTCTCCATTCCTGCACTCTGGGATGAAAATGCAGAAGGCAGGTCCCCCAGTACCTG |
| | | CCTCGCACATAGCACCTGCCCCTGTGCAGCCCCCCATGATTCGGCGGGATATCACCTTCCCA |
| | | CCTGGCTCTGTTGAAGCCACACAGCCTGTGTTGAAGCAGAGGAGGCGGCTCACAATGAAAG |
| | | ACATTGGAACCCCGGAGGCATGGCGGGTAATGATGTCCCTCAAGTCTGGTCTCCTGGCAGA |
| | | GAGCACATGGGCATTAGATACCATCAACATCCTGCTGTATGATGACAACAGCATCATGACCTT |
| | | CAACCTCAGTCAGCTCCCAGGGTTGCTAGAGCTCCTTGTAGAATATTTCCGACGATGCCTGA |
| | | TTGAGATCTTTGGCATTTTAAAGGAGTATGAGGTGGGTGACCCAGGACAGAGAACGCTACTG |
| | | GATCCTGGGAGGTTCAGCAAGGTGTCTAGTCCAGCTCCCATGGAGGGTGGGGAAGAAGAAG |
| | | AAGAACTTCTAGGTCCTAAACTAGAAGAGGAAGAAGAAGAGGAAGTAGTTGAAAATGATGAG |
| | | GAGATAGCCTTTTCAGGCAAGGACAAGCCAGCTTCAGAGAATAGTGAGGAGAAGCTGATCAG |
| | | TAAGTTTGACAAGCTTCCAGTAAAGATCGTACAGAAGAATGATCCATTTGTGGTGGACTGCTC |
| | | AGATAAGCTTGGGCGTGTGCAGGAGTTTGACAGTGGCCTGCTGCACTGGCGGATTGGTGGG |
| | | GGGGACACCACTGAGCATATCCAGACCCACTTCGAGAGCAAGACAGAGCTGCTGCCTTCCC |
| | | GGCCTCACGCACCCTGCCCACCAGCCCCTCGGAAGCATGTGACAACAGCAGAGGGTACACC |
| | | AGGGACAACAGACCAGGAGGGGCCCCCACCTGATGGACCTCCAGAAAAACGGATCACGACC |
| | | ACTATGGATGACATGTTGTCTACTCGGTCTAGCACCTTGACCGAGGATGGAGCTAAGAGTTC |
| | | AGAGGCCATCAAGGAGAGCAGCAAGTTTCCATTTGGCATTAGCCCAGCACAGAGCCACCGG |
| | | AACATCAAGATCCTAGAGGACGAACCCACAGTAAGGATGAGACCCCACTGTGTACCCTTCT |
| | | GGACTGGCAGGATTCTCTTGCCAAGCGCTGCGTCTGTGTGTCCAATACCATTCGAAGCCTGT |
| | | CATTTGTGCCAGGCAATGACTTTGAGATGTCCAAACACCCAGGGCTGCTGCTCATCCTGGGC |
| | | AAGCTGATCCTGCTGCACCACAAGCACCCAGAACGGAAGCAGGCACCACTAACTTATGAAAA |
| | | GGAGGAGGAACAGGACCAAGGGGTGAGCTGCAACAAAGTGGAGTGGTGGTGGGACTGCTT |
| | | GGAGATGCTCCGGGAAAACACCTTGGTTACACTCGCCAACATCTCGGGGCAGTTGGACCTAT |
| | | CTCCATACCCCGAGAGCATTTGCCTGCCTGTCCTGGACGGACTCCTACACTGGGCAGTTTGC |
| | | CCTTCAGCTGAAGCCCAGGACCCCTTTTCCACCCTGGGCCCAATGCCGTCCTTTCCCCGCA |
| | | GAGACTGGTCTTGGAAACCCTCAGCAAACTCAGCATCCAGGACAACAATGTGGACCTGATTC |
| | | TGGCCACACCCCCTTCAGCCGCCTGGAGAAGTTGTATAGCACTATGGTGCGCTTCCTCAGT |
| | | GACCGAAAGAACCCGGTGTGCCGGGAGATGGCTGTGGTACTGCTGGCCAACCTGGCTCAGG |
| | | GGGACAGCCTGGCAGCTCGTGCCATTGCAGTGCAGAAGGGCAGTATCGGCAACCTCCTGGG |
| | | CTTCCTAGAGGACAGCCTTGCCGCCACACAGTTCCAGCAGAGCCAGGCCAGCCTCCTCCAC |
| | | ATGCAGAACCCACCCTTTGAGCCAACTAGTGTGGACATGATGCGGCGGGCTGCCCGCGCGC |
| | | TGCTTGCCTTGGCCAAGGTGGACGAGAACCACTCAGAGTTTACTCTGTACGAATCACGGCTG |
| | | TTGGACATCTCGGTATCACCGTTGATGAACTCATTGGTTTCACAAGTCATTTGTGATGTACTGT |
| | | TTTTGATTGGCCAGTCCTCGAGTCTAGAGGGCCCGCGGTTCGAAGGTAAGCCTATCCCTAAC |
| | | CCTCTCCTCGGTCTCGATTCTACGCGTACCGGTCATCATCACCATCACCATTGAgtttaaacCCG |

SEQUENCE LISTING

| SEQ ID NO. | Name | Sequence |
|---|---|---|
| | | CTGATCAGCCTCGACTGTGCCTTCTAGTTGCCAGCCATCTGTTGTTTGCCCCTCCCCCGTGC |
| | | CTTCCTTGACCCTGGAAGGTGCCACTCCCACTGTCCTTTCCTAATAAAATGAGGAAATTGCAT |
| | | CGCATTGTCTGAGTAGGTGTCATTCTATTCTGGGGGGTGGGGTGGGGCAGGACAGCAAGGG |
| | | GGAGGATTGGGAAGACAATAGCAGGCATGCTGGGGATGCGGTGGGCTCTATGGCTTCTGAG |
| | | GCGGAAAGAACCAGCTGGGGCTCTAGGGGGTATCCCCACGCGCCCTGTAGCGGCGCATTAA |
| | | GCGCGGCGGGTGTGGTGGTTACGCGCAGCGTGACCGCTACACTTGCCAGCGCCCTAGCGC |
| | | CCGCTCCTTTCGCTTTCTTCCCTTCCTTTCTCGCCACGTTCGCCGGCTTTCCCCGTCAAGCTC |
| | | TAAATCGGGGGCTCCCTTTAGGGTTCCGATTTAGTGCTTTACGGCACCTCGACCCCAAAAAA |
| | | CTTGATTAGGGTGATGGTTCACGTAGTGGGCCATCGCCCTGATAGACGGTTTTTCGCCCTTT |
| | | GACGTTGGAGTCCACGTTCTTTAATAGTGGACTCTTGTTCCAAACTGGAACAACACTCAACCC |
| | | TATCTCGGTCTATTCTTTTGATTTATAAGGGATTTTGCCGATTTCGGCCTATTGGTTAAAAAAT |
| | | GAGCTGATTTAACAAAAATTTAACGCGAATTAATTCTGTGGAATGTGTGTCAGTTAGGGTGTG |
| | | GAAAGTCCCCAGGCTCCCCAGCAGGCAGAAGTATGCAAAGCATGCATCTCAATTAGTCAGCA |
| | | ACCAGGTGTGGAAAGTCCCCAGGCTCCCCAGCAGGCAGAAGTATGCAAAGCATGCATCTCA |
| | | ATTAGTCAGCAACCATAGTCCCGCCCCTAACTCCGCCCATCCCGCCCCTAACTCCGCCCAGT |
| | | TCCGCCCATTCTCCGCCCCATGGCTGACTAATTTTTTTATTTATGCAGAGGCCGAGGCCGCC |
| | | TCTGCCTCTGAGCTATTCCAGAAGTAGTGAGGAGGCTTTTTGGAGGCCTAGGCTTTTGCAAA |
| | | AAGCTCCCGGGAGCTTGTATATCCATTTTCGGATCTGATCAGCACGTGTTGACAATTAATCAT |
| | | CGGCATAGTATATCGGCATAGTATAATACGACAAGGTGAGGAACTAAACCATGGCCAAGCCT |
| | | TTGTCTCAAGAAGAATCCACCCTCATTGAAAGAGCAACGGCTACAATCAACAGCATCCCCATC |
| | | TCTGAAGACTACAGCGTCGCCAGCGCAGCTCTCTAGCGACGGCCGCATCTTCACTGGTGT |
| | | CAATGTATATCATTTTACTGGGGGACCTTGTGCAGAACTCGTGGTGCTGGGCACTGCTGCTG |
| | | CTGCGGCAGCTGGCAACCTGACTTGTATCGTCGCGATCGGAAATGAGAACAGGGGCATCTT |
| | | GAGCCCCTGCGGACGGTGCCGACAGGTGCTTCTCGATCTGCATCCTGGGATCAAAGCCATA |
| | | GTGAAGGACAGTGATGGACAGCCGACGGCAGTTGGGATTCGTGAATTGCTGCCCTCTGGTT |
| | | ATGTGTGGGAGGGCTAAGCACTTCGTGGCCGAGGAGCAGGACTGACACGTGCTACGAGATT |
| | | TCGATTCCACCGCCGCCTTCTATGAAAGGTTGGGCTTCGGAATCGTTTTCCGGGACGCCGGC |
| | | TGGATGATCCTCCAGCGCGGGGATCTCATGCTGGAGTTCTTCGCCCACCCCAACTTGTTTAT |
| | | TGCAGCTTATAATGGTTACAAATAAAGCAATAGCATCACAAATTTCACAAATAAAGCATTTTTT |
| | | CACTGCATTCTAGTTGTGGTTTGTCCAAACTCATCAATGTATCTTATCATGTCTGTATACCGTC |
| | | GACCTCTAGCTAGAGCTTGGCGTAATCATGGTCATAGCTGTTTCCTGTGTGAAATTGTTATCC |
| | | GCTCACAATTCCACACAACATACGAGCCGAAGCATAAAGTGTAAAGCCTGGGGTGCCTAAT |
| | | GAGTGAGCTAACTCACATTAATTGCGTTGCGCTCACTGCCCGCTTTCCAGTCGGGAAACCTG |
| | | TCGTGCCAGCTGCATTAATGAATCGGCCAACGCGCGGGGAGAGGCGGTTTGCGTATTGGGC |
| | | GCTCTTCCGCTTCCTCGCTCACTGACTCGCTGCGCTCGGTCGTTCGGCTGCGGCGAGCGGT |
| | | ATCAGCTCACTCAAAGGCGGTAATACGGTTATCCACAGAATCAGGGGATAACGCAGGAAAGA |
| | | ACATGTGAGCAAAAGGCCAGCAAAAGGCCAGGAACCGTAAAAAGGCCGCGTTGCTGGCGTT |
| | | TTTCCATAGGCTCCGCCCCCTGACGAGCATCACAAAAATCGACGCTCAAGTCAGAGGTGGC |
| | | GAAACCCGACAGGACTATAAAGATACCAGGCGTTTCCCCCTGGAAGCTCCCTCGTGCGCTCT |
| | | CCTGTTCCGACCCTGCCGCTTACCGGATACCTGTCCGCCTTTCTCCCTTCGGGAAGCGTGGC |
| | | GCTTTCTCATAGCTCACGCTGTAGGTATCTCAGTTCGGTGTAGGTCGTTCGCTCCAAGCTGG |
| | | GCTGTGTGCACGAACCCCCCGTTCAGCCCGACCGCTGCGCCTTATCCGGTAACTATCGTCTT |
| | | GAGTCCAACCCGGTAAGACACGACTTATCGCCACTGGCAGCAGCCACTGGTAACAGGATTAG |
| | | CAGAGCGAGGTATGTAGGCGGTGCTACAGAGTTCTTGAAGTGGTGGCCTAACTACGGCTACA |
| | | CTAGAAGAACAGTATTTGGTATCTGCGCTCTGCTGAAGCCAGTTACCTTCGGAAAAAGAGTTG |
| | | GTAGCTCTTGATCCGGCAAACAAACCACCGCTGGTAGCGGTGGTTTTTTTGTTTGCAAGCAG |
| | | CAGATTACGCGCAGAAAAAAAGGATCTCAAGAAGATCCTTTGATCTTTTCTACGGGGTCTGAC |
| | | GCTCAGTGGAACGAAAACTCACGTTAAGGGATTTTGGTCATGAGATTATCAAAAGGATCTTC |
| | | ACCTAGATCCTTTTAAATTAAAAATGAAGTTTTAAATCAATCTAAAGTATATATGAGTAAACTTG |
| | | GTCTGACAGTTACCAATGCTTAATCAGTGAGGCACCTATCTCAGCGATCTGTCTATTTCGTTC |
| | | ATCCATAGTTGCCTGACTCCCCGTCGTGTAGATAACTACGATACGGGAGGGCTTACCATCTG |
| | | GCCCCAGTGCTGCAATGATACCGCGAGACCCACGCTCACCGGCTCCAGATTTATCAGCAATA |
| | | AACCAGCCAGCCGGAAGGGCCGAGCGCAGAAGTGGTCCTGCAACTTTATCCGCCTCCATCC |
| | | AGTCTATTAATTGTTGCCGGGAAGCTAGAGTAAGTAGTTCGCCAGTTAATAGTTTGCGCAACG |
| | | TTGTTGCCATTGCTACAGGCATCGTGGTGTCACGCTCGTCGTTTGGTATGGCTTCATTCAGCT |
| | | CCGGTTCCCAACGATCAAGGCGAGTTACATGATCCCCCATGTTGTGCAAAAAAGCGGTTAGC |
| | | TCCTTCGGTCCTCCGATCGTTGTCAGAAGTAAGTTGGCCGCAGTGTTATCACTCATGGTTATG |
| | | GCAGCACTGCATAATTCTCTTACTGTCATGCCATCCGTAAGATGCTTTTCTGTGACTGGTGAG |
| | | TACTCAACCAAGTCATTCTGAGAATAGTGTATGCGGCGACCGAGTTGCTCTTGCCCGGCGTC |
| | | AATACGGGATAATACCGCGCCACATAGCAGAACTTTAAAAGTGCTCATCATTGGAAAACGTTC |
| | | TTCGGGGCGAAAACTCTCAAGGATCTTACCGCTGTTGAGATCCAGTTCGATGTAACCCACTC |
| | | GTGCACCCAACTGATCTTCAGCATCTTTTACTTTCACCAGCGTTTCTGGGTGAGCAAAAACAG |
| | | GAAGGCAAAATGCCGCAAAAAAGGGAATAAGGGCGACACGGAAATGTTGAATACTCATACTC |
| | | TTCCTTTTTCAATATTATTGAAGCATTTATCAGGGTTATTGTCTCATGAGCGGATACATATTTGA |
| | | ATGTATTTAGAAAAATAAACAAATAGGGGTTCCGCGCACATTTCCCCGAAAAGTGCCACCTGA |
| | | CGTC |
| 13 | CAD peptide 1 | LLDTIGISQPQWR |
| 14 | CAD peptide 2 | MAEIGEHVAPSEAANSLEQAQAAAER |

The invention claimed is:

1. A method for treating an ARID1A-mutant tumor or cancer in a subject in need thereof comprising:
   (i) administering to the subject an effective amount of a pyrimidine synthesis inhibitor and
   (ii) administering to the subject an effective amount of a DNA repair inhibitor.

2. The method of claim 1, wherein the pyrimidine synthesis inhibitor and DNA repair inhibitors are individually a small molecule, protein, fusion protein, peptide, nucleic acid, aptamer, avimer, or derivatives or fragments thereof.

3. The method of claim 1, wherein the pyrimidine synthesis inhibitor is an inhibitor of DHODH, an inhibitor of orotate phosphoribosyl transferase, an inhibitor of orotidylate decarboxylase, a direct inhibitor of CAD, a S6K1 inhibitor, an mTORC1 inhibitor, an inhibitor of mTORC1 signaling, or a combination thereof.

4. The method of claim 1, wherein the pyrimidine synthesis inhibitor is a DHODH inhibitor.

5. The method of claim 4, wherein the DHODH inhibitor is teriflunomide, leflunomide, or a combination thereof.

6. The method of claim 5, wherein the DHODH inhibitor is teriflunomide.

7. The method of claim 5, wherein teriflunomide is administered at a dose from about 2.5 mg to about 25 mg and/or leflunomide is administered at a dose from about 4 mg to about 40 mg.

8. The method of claim 1, wherein the pyrimidine synthesis inhibitor is a S6K1 inhibitor.

9. The method of claim 8, wherein the S6K1 inhibitor is PF-4708671.

10. The method of claim 9, wherein PF-4708671 is administered at a dose from about 0.5 mg to about 50 mg.

11. The method of claim 1, wherein the DNA repair inhibitor is an ATR inhibitor, a CHK1 inhibitor, or a Parp inhibitor.

12. The method of claim 11, wherein the ATR inhibitor is AZD6738, VX-970, or a combination thereof.

13. The method of claim 12, wherein VX-970 is administered at a dose from about 1 mg to about 100 mg and/or AZD6738 is administered at a dose from about 20 mg to about 240 mg.

14. The method of claim 1, wherein the ARID1A-mutant tumor or cancer is in a brain, breast, bladder, bone, cartilage, cervix, colon, cornea, eye, neural tissue, glia, esophagus, fallopian tube, heart, pancreas, intestines, gallbladder, kidney, liver, lung, ovary, pancreas, parathyroid, pineal gland, pituitary gland, prostate, spinal cord, spleen, skeletal muscle, skin, muscle, stomach, testis, thymus, thyroid, trachea, urogenital tract, ureter, urethra, uterus, endometrium, vagina, or combination thereof.

15. The method of claim 1, wherein the ARID1A-mutant cancer is clear cell ovarian cancer, endometrioid ovarian cancer, endometrial cancer, or uterine carcinosarcoma.

16. The method of claim 1, further comprising determining the presence of an ARID1A mutation in tumor or cancer cells of the subject prior to administering the pyrimidine synthesis inhibitor and DNA repair inhibitor.

17. The method of claim 1, wherein the ARID1A-mutant tumor or cancer is not a PTEN-mutant tumor or cancer.

18. A method for treating an ARID1A-mutant tumor or cancer in a subject in need thereof comprising administering to the subject a) an effective amount of a composition comprising a pyrimidine synthesis inhibitor and b) an effective amount of a composition comprising a DNA repair inhibitor.

19. A method for decreasing proliferation of an aberrantly proliferating cell comprising an ARID1A mutation in a subject in need thereof, said method comprising:
   (i) administering to the subject an effective amount of a pyrimidine synthesis inhibitor and
   (ii) administering to the subject an effective amount of a DNA repair inhibitor.

* * * * *